US008114871B2

(12) United States Patent
Botrous et al.

(10) Patent No.: US 8,114,871 B2
(45) Date of Patent: Feb. 14, 2012

(54) 3-AMIDO-PYRROLO[3,4-C]PYRAZOLE-5(1H,4H,6H)6) CARBALDEHYDE DERIVATIVES

(75) Inventors: Iriny Botrous, San Diego, CA (US); Yufeng Hong, San Diego, CA (US); Hui Li, Carlsbad, CA (US); Kevin Kun-Chin Liu, San Marcos, CA (US); Seiji Nukui, San Diego, CA (US); Min Teng, San Diego, CA (US); Eileen Valenzuela Tompkins, Escondido, CA (US); Chunfeng Yin, San Diego, CA (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 12/532,051

(22) PCT Filed: Apr. 10, 2008

(86) PCT No.: PCT/IB2008/000862
§ 371 (c)(1),
(2), (4) Date: Feb. 1, 2010

(87) PCT Pub. No.: WO2008/125945
PCT Pub. Date: Oct. 23, 2008

(65) Prior Publication Data
US 2010/0249128 A1 Sep. 30, 2010

Related U.S. Application Data

(60) Provisional application No. 60/911,462, filed on Apr. 12, 2007, provisional application No. 61/035,519, filed on Mar. 11, 2008, provisional application No. 61/040,115, filed on Mar. 27, 2008.

(51) Int. Cl.
A61K 31/535 (2006.01)
A61K 31/495 (2006.01)
A61K 31/497 (2006.01)
A61K 31/4965 (2006.01)
C07D 413/14 (2006.01)
C07D 237/00 (2006.01)
C07D 239/00 (2006.01)
C07D 403/14 (2006.01)
C07D 241/36 (2006.01)
C07D 401/14 (2006.01)

(52) U.S. Cl. ............... 514/234.2; 514/249; 514/253.09; 514/254.06; 514/250; 514/255.06; 544/121; 544/230; 544/231; 544/282; 544/295; 544/344; 544/349; 544/363; 544/371

(58) Field of Classification Search ............... 514/234.2, 514/249, 253.09, 254.06, 250, 255.06; 544/121, 544/230, 231, 282, 295, 344, 349, 363, 371
See application file for complete search history.

(56) References Cited

U.S. PATENT DOCUMENTS
2003/0171357 A1 9/2003 Fancelli et al.

FOREIGN PATENT DOCUMENTS
| WO | WO-02-12242 A2 | 2/2002 | |
| WO | WO 0212242 | 2/2002 | |
| WO | WO 2004/056827 | * 7/2004 | ............... 548/360.5 |
| WO | WO-2004-080457 A1 | 9/2004 | |
| WO | WO-2005-030776 A1 | 4/2005 | |
| WO | WO-2006-072831 A1 | 7/2006 | |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Golub et al. Science (1999), vol. 286 531-537.*
Lala et al. Cancer and Metastasis Reviews (1998), 17(1), 91-106.*
Ahmad, S., et al., "Expression of the Antisense cDNA for Protein Kinase Cα Attenuates Resistance in Doxorubicin-Resistant MCF-7 Breast Carcinoma Cells", Molecular Pharmacology, 1993, 858-862, vol. 43.
Akinaga, S., et al., "Antitumor Activity of UCN-01, a Selective Inhibitor of Protein Kinase C, in Murine and Human Tumor Models", Cancer Research, 1991, 4888-4892, vol. 51.
Bastyr, E., III, et al., "Increased Platelet Protein Kinase C-β(PKC-β) in IDDM", Diabetes, 1993, 304, (Suppl. 1), vol. 42.
Tesfamariam, B., et al., "Elevated Glucose Impairs Endothelium-dependent Relaxation by Activating Protein Kinase C", The American Journal of Clinical Investigation, 1991, 1643-1648, vol. 87.
Bilder, G., et al., "Phorbol-12, 13-Dibutyrate-Induced Vasoconstriction in Vivo: Characterization of Response in Genetic Hypertension", The Journal of Pharmacology and Experimental Therapeutics, 1990, 526-530, vol. 252, No. 2.

(Continued)

Primary Examiner — Rebecca Anderson
Assistant Examiner — Samantha Shterengarts
(74) Attorney, Agent, or Firm — Wilson, Sonsini, Goodrich & Rosati

(57) ABSTRACT

The present invention relates to compounds and pharmaceutically acceptable salts of Formula (I): wherein X, $R^1$, $R^2$, $R^3$, $R^4$, $R^5$, $R^6$, $R^7$, and $R^8$ are as defined above. The invention further relates to pharmaceutical compositions comprising the compounds and pharmaceutically acceptable salts and to methods of treating diabetes mellitus and its complications (including in particular diabetic retinopathy, nephropathy or neuropathy), cancer, ischemia, inflammation, central nervous system disorders, cardiovascular disease, Alzheimer's disease and dermatological disease pression, viral diseases, inflammatory disorders, or diseases in which the liver is a target organ.

(I)

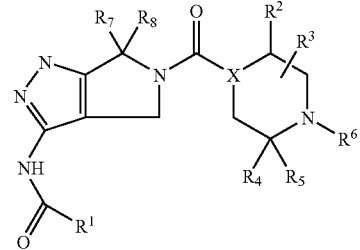

14 Claims, No Drawings

OTHER PUBLICATIONS

Bollag, W., et al., "Effects of the Selective Protein Kinase C Inhibitor, Ro 31-7549, on the Proliferation of Cultured Mouse Epidermal Keratinocytes", The Journal of Investigative Dermatology, 1993, 240-246, vol. 100, No. 3.

Braz, J., et al., "PKC-α Regulates Cardiac Contractility and Propensity Toward Heart Failure", Nature Medicine, 2004, 248-254, vol. 10, No. 3.

Chen, K., et al., "Diacylglycerol-Protein Kinase C Signalling in Skeletal Muscle: A Possible Link to Insulin Resistance", Transactions of the Association of American Physicians, 1991, 206-212, vol. 104.

Chin, J., et al., "Overexpression of Protein Kinase C Isoenzymes α, βI, γ, and ε in Cells Overexpressing the Insulin Receptor", The Journal of Biological Chemistry, 1993, 6338-6347, vol. 268, No. 9.

Craven, P., et al., "Protein Kinase C Is Activated in Glomeruli from Streptozotocin Diabetic Rats", The Journal of Clinical Investigation, Inc., 1989, 1667-1675, vol. 83.

Graff, J., et al., "The Protein Kinase Cβ-Selective Inhibitor, Enzastaurin (LY317615.HCl), Suppresses Signaling Through the AKT Pathway, Induces Apoptosis, and Suppresses Growth of Human Colon Cancer and Glioblastoma Xenografts", Cancer Research, 2005, 7462-7469, vol. 65, No. 16.

Hara, H., et al., "Staurosporine, a Novel Protein Kinase C Inhibitor, Prevents Postischemic Neuronal Damage in the Gerbil and Rat", Journal of Cerebral Blood Flow and Metabolism, 1990, 646-653, vol. 10.

Hegemann, L., et al., "Effects of Tiflucarbine as a Dual Protein Kinase C/calmodulin Antagonist on Proliferation of Human Keratinocytes and Release of Reactive Oxygen Species from Human Leukocytes", Archives of Dermatological Research, 1991, 456-460, vol. 283.

Horn, F., et al., "Decreased Protein Kinase C Activity in Psoriatic Versus Normal Epidermis", The Society for Investigative Dermatology, Inc., 1987, 220-222, vol. 88, No. 2.

Hsieh, J., et al., "Human Vitamin D Receptor is Selectively Phosphorylated by Protein Kinase C on Serine 51, a Residue Crucial to its Trans-Activation Function", Proc. Natl. Acad. Sci. USA, 1991, 9315-9319, vol. 88.

Hsieh, J., et al., "Phosphorylation of the Human Vitamin D Receptor by Protein Kinase C", The Journal of Biological Chemistry, 1993, 15118-15126, vol. 268, No. 20.

Huang, K., "The Mechanism of Protein Kinase C Activation", Trends in Neurosciences, 1989, 425-432, vol. 12, No. 11.

Inoguchi, T., et al., "Preferential Elevation of Protein Kinase C Isoform βII and Diacylglycerol Levels in the Aorta and Heart of Diabetic Rats: Differential Reversibility to Glycemic Control by Islet Cell Transplantation", Proc. Nat. Acad. Sci. USA, 1992, 11059-11063, vol. 89.

Karasik, A., et al. "Increased Protein Kinase C Activity is Linked to Reduced Insulin Receptor Autophosphorylation in Liver of Starved Rats", The Journal of Biological Chemistry, 1990, 10226-10231, vol. 265, No. 18.

Kobayashi, I., et al., "Platelet-Activating Factor Modulates Microvascular Transport by Stimulation of Protein Kinase C", The American Physiological Society, 1994, H1214-H1220.

Lee, T., et al., "Differential Regulation of Protein Kinase C and (Na,K)-Adenosine Triphosphatase Activities by Elevated Glucose Levels in Retinal Capillary Endothelial Cells", The Journal of Clinical Investigation, 1989, 90-94, vol. 83.

Lee, T., et al., "Activation of Protein Kinase C by Elevation of Glucose Concentration: Proposal for a Mechanism in the Development of Diabetic Vascular Complications", Proc. Nat'l. Acad. Sci. USA, 1989, 5141-5145, vol. 86.

Matsumoto, H., et al., "Staurosporine, a Protein Kinase C Inhibitor Interferes with Proliferation of Arterial Smooth Muscle Cells", Biochemical and Biophysical Research Communications, 1989, 105-109, vol. 158, No. 1.

Menne, J., et al., "Diminished Loss of Proteoglycans and Lack of Albuminuria in Protein Kinase C-α-Deficient Diabetic Mice", Diabetes, 2004, 2101-2109, vol. 53.

Meyer, T., et al., "A Derivative of Staurosporine (CGP 41 251) Shows Selectivity for Protein Kinase C Inhibition and in Vitro Anti-Proliferative As Well As in Vivo Anti-Tumor Activity", International Journal of Cancer, 1989, 851-856, vol. 43.

Morrison, J., "Kinetics of the Reversible Inhibition of Enzyme-Catalysed Reactions by Tight-Binding Inhibitors", Biochimica et Biophysica Acta, 1969, 269-286, vol. 185.

Muid, R., et al., "A Novel Conformationally Restricted Protein Kinase C Inhibitor, Ro 31/8425, Inhibits Human Neutrophil Superoxide Generation by Soluble, Particulate and Post-receptor Stimuli", Federation of European Biochemical Societies, 1991, 169-172, vol. 293, No. 1, 2.

Mulqueen, M., et al., "Oral, Anti-inflammatory Activity of a Potent, Selective, Protein Kinase C Inhibitor", Agents Actions, 1992, 85-89, vol. 37.

Murray, N., et al., "Protein Kinase C Isotypes in Human Erythroleukemia (K562) Cell Proliferation and Differentiation", The Journal of Biological Chemistry, 1993, 15847-15853, vol. 268, No. 21.

Partovian, C., et al., "Regulation of Protein Kinase B/Akt Activity and Ser 473 Phosphorylation by Protein Kinase Cα in Endothelial Cells", Cellular Signalling, 2004, 951-957, vol. 16.

Patani, G., et al., "Bioisosterism: A Rational Approach in Drug Design", Chemical Reviews, 1996, 3147-3176, vol. 96.

Raynaud, F., et al., "Protein Kinase C Activity in Normal and Psoriatic Cells: Cultures of Fibroblasts and Lymphocytes", British Journal of Dermatology, 1991, 542-546, vol. 124.

Rotenberg, S., et al., "Protein Kinase C in Neoplastic Cells", Biochemical and Molecular Aspects of Selected Cancers, 1991, 25-73, vol. 1.

Shibata, S., et al., "Neuroprotective Effect of Protein Kinase C Inhibitors on Oxygen/Glucose Free-Induced Decreases in 2-Deoxyglucose Uptake and CA1 Field Potentials in Rat Hippocampal Slices", Brain Research, 1992, 290-294, vol. 594.

Shimohama, S., et al., "Assessment of Protein Kinase C Isozymes by Two-site Enzyme Immunoassay in Human Brains and Changes in Alzheimer's Disease", Neurology, 1993, 1407-1413, vol. 43.

Sonoki, H., et al., "Protein at the Time in the Left Cardiac Ventricle Relaxation Obstacle, The Role of Kinase C*," Kokyu to Jukan, 1989, 668-674, vol. 137, No. 6.

Toullec, D., et al., "The Bisindolylmaleimide GF 109203X Is a Potent and Selective Inhibitor of Protein Kinase C*", The Journal of Biological Chemistry, 1991, 15771-15781, vol. 266, No. 24.

Twomey, B., et al., "The Effect of New Potent Selective Inhibitors of Protein Kinase C on the Neutrophil Respiratory Burst", Biochemical and Biophysical Research Communications, 1990, 1087-1092, vol. 171, No. 3.

Vinik, A., "The Protein Kinase C-β Inhibitor, Ruboxistaurin, for the Treatment of Diabetic Microvascular Complications", Expert Opinion Investigative Drugs, 2005, 1547-1559, vol. 14, No. 12.

Way, K.., et al., "Protein Kinase C and the Development of Diabetic Vascular Complications", Diabetic Medicine, 2001, 945-959, vol. 18.

Intellectual Property Office of Singapore Application No. 200906416-3 Search Report and Written Opinion mailed Apr. 20, 2011.

* cited by examiner

3-AMIDO-PYRROLO[3,4-C]PYRAZOLE-5(1H,4H,6H) CARBALDEHYDE DERIVATIVES

This application is the National Stage of International Application No. PCT/IB2008/000862, filed Apr. 10, 2008, and claims the benefit of U.S. Provisional Application No. 60/911,462, filed Apr. 12, 2007, U.S. Provisional Application No. filed 61/035,519, filed Mar. 11, 2008, and U.S. Provisional Application No. 61/040,115, filed Mar. 27, 2008, the contents of which are hereby incorporated by reference in their entireties.

FIELD OF THE INVENTION

The present invention relates to novel compounds, to pharmaceutical compositions comprising the compounds, as well as to the use of the compounds in medicine and for the preparation of a medicament which acts on the human protein kinase C enzyme, and in particular the beta II isoform (pkcβII).

BACKGROUND OF THE INVENTION

Protein kinase C (PKC) is a superfamily of lipid-activated Ser/Thr kinases involved in multiple signal transduction pathways. There are thirteen PKC-isoforms that have been identified and are classified according to their regulation by cellular signaling molecules such as diacylglycerol, phospholipids, and calcium. The protein kinase C isozymes, alpha, beta (two splice variants PKCβI and PKCβII) and gamma, require membrane phospholipids, calcium and diacylglycerolphorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipids for their activation.

The tissue-specific expression and activation of PKC-isoforms suggests that individual PKC-isoforms might be potential therapeutic targets. For diabetes, activation of PKC-beta has been demonstrated in tissues of diabetic animals and has been implicated in the development of microvascular abnormalities related to the hyperglycemic state. Genetic polymorphisms have been identified in the 5'-flanking upstream region of the PKCβ gene in Japanese patients with type II diabetes. This PKCβ genetic variation was associated with a significant increase in the susceptibility to develop diabetic vascular complications and macrovascular diseases such as coronary heart disease.

In a large case-control study at the Joslin Diabetes Center, additional polymorphisms were identified in the PKCβ promoter region that had an association with type I diabetes mellitus (duration<24 years) and a greater risk for development of diabetic nephropathy. Administration of PKCβ inhibitors such as ruboxistaurin mesylate (LY333531, Lilly) in diabetic animal models, was shown to prevent or ameliorate the hemodynamic changes and vascular damage associated with diabetic nephropathy, diabetic peripheral neuropathy, and diabetic retinopathy. Way, K. J. et al, *Diabet. Med.* 18: 945-959 (2001); Vinik, A., *Expert Opin. Investig. Drugs* 14: 1547-1559 (2005). Together with additional data from phase II and phase III clinical studies of ruboxistaurin mesylate for treatment of diabetes and diabetic microvascular complications, there is a building body of evidence to support the rationale that PKCβ can function as a molecular target for diabetic complications and for the development of selective-PKCβ inhibitors as potential therapeutic agents.

The compounds of the present invention are protein kinase C beta II inhibitors, and are therefore believed to be useful in the treatment of conditions associated with diabetes mellitus and its complications, cancer, ischemia, inflammation, central nervous system disorders, cardiovascular disease and dermatological disease.

SUMMARY OF THE INVENTION

The present invention is directed to compounds or pharmaceutically acceptable salts or solvates of Formula (I),

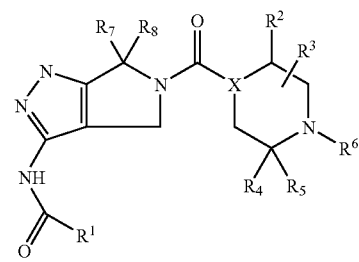

(I)

wherein:
X is C or N;
$R^1$ is selected from an aryl or

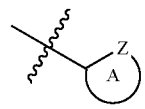

wherein ring A is a 5 to 6 membered heterocyclyl containing Z, wherein Z is an O, S or N heteroatom which is adjacent to the point of attachment, and wherein $R^1$ is optionally further substituted with 0 to 3 $R^9$ groups and wherein two of the $R^9$ groups may optionally cyclize to form an aryl or a 5-6 membered heterocyclyl ring containing N or S fused to the aryl or heterocyclyl to which it is attached;

$R^2$ is H or $C_1$-$C_6$ alkyl optionally further substituted with 0 to 3 $R^9$ groups;

$R^3$ may be attached to any carbon on the ring and is selected from H, $C_1$-$C_6$alkyl or halide, or perfluoroalkyl;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-aryl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)$R^a$, —$(R^d)_m$C(O)O$R^a$, —$(R^d)_m$C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$ OS(O)NR$^a$R$^b$, —$(R^d)_m$—NO$_2$, —$(R^d)_m$—NR$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$ NR$^a$R$^b$, —$(R^d)_m$—O—$(R^e)_m$—NR$^a$R$^b$ or —$(R^d)_m$—NR$^a$—$(R^e)$—OR$^b$, or $R^4$ and $R^5$ may together cyclize to form a 3-to-5-membered spiro-cycloalkyl; wherein any of the said $C_3$-$C_{12}$ cycloalkyl, aryl, heterocyclyl, or heteroaryl are independently optionally further substituted by 0 to 3 $R_9$ groups;

$R^6$ is selected from H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-aryl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$C(O)O$R^a$, —$(R^d)_m$—C(O)N$R^a R^b$, —$(R^d)_m$—O$R^a$, —$(R^d)_m$—OC(O)$R^a$, —$(R^d)_m$—OC(O)N$R^a R^b$, —$(R^d)_m$—O—S(O)$R^a$, OS(O)$_2 R^a$, —$(R^d)_m$—OS(O)$_2$N$R^a R^b$, —$(R^d)_m$—OS(O)N$R^a R^b$, —$(R^d)_m$—NO$_2$, —$(R^d)_m$—N$R^a R^b$, —$(R^d)_m$—N($R^a$)C(O)$R^b$, —$(R^d)_m$—N($R^a$)C(O)O$R^b$, —$(R^d)_m$—N($R^c$)C(O)N$R^a R^b$, —$(R^d)_m$—N($R^a$)S(O)$_2 R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2 R^a$, —$(R^d)_m$—S(O)N$R^a R^b$, —$(R^d)_m$—S(O)$_2$N$R^a R^b$, —$(R^d)_m$—O—$(R^e)_m$—N$R^a R^b$ or —$(R^d)_m$—N$R^a$—$(R^e)$—O$R^b$; or $R^6$ may together with $R^4$ cyclize to form a 4- to 7-membered heterocyclyl ring fused to the piperazine or piperadine to which they are attached; and wherein any of the said alkyl, alkenyl, alkynyl, cycloalkyl, aryl, heterocyclyl, and heteroaryl may independently be further substituted with 0 to 3 $R^9$ groups;

each $R^7$ and $R^8$ are each independently $C_1$-$C_2$ alkyl or can together cyclize to form a cyclopropyl or cyclobutyl;

each $R^9$ is independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)_m$—CN, —$(R^d)_m$—($C_1$-$C_8$ perfluoroalkyl), —$(R^d)_m$—CN, —$(R^d)_m$—C(O)$R^a$, —$(R^d)_m$C(O)O$R^a$, —$(R^d)_m$C(O)N$R^a R^b$, —$(R^d)_m$—O$R^a$, —$(R^d)_m$—OC(O)$R^a$, —$(R^d)_m$—OC(O)N$R^a R^b$, —$(R^d)_m$—O—S(O)$R^a$, —$(R^d)_m$—OS(O)$_2 R^a$, —$(R^d)_m$—OS(O)$_2$N$R^a R^b$, —$(R^d)_m$—OS(O)N$R^a R^b$, —$(R^d)_m$—NO$_2$, —$(R^d)_m$—N$R^a R^b$, —$(R^d)_m$—N($R^a$)C(O)$R^b$, —$(R^d)_m$—N($R^a$)C(O)O$R^b$, —$(R^d)_m$—N($R^c$)C(O)N$R^a R^b$, —$(R^d)_m$—N($R^a$)S(O)$_2 R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2 R^a$, —$(R^d)_m$—S(O)N$R^a R^b$, —$(R^d)_m$—S(O)$_2$N$R^a R^b$, —$(R^d)_m$—O—$(R^e)_m$—N$R^a R^b$ or —$(R^d)_m$—N$R^a$—$(R^e)$—O$R^b$; and wherein any of the said alkyl, alkenyl, alkynyl, $R^d$, $R^e$, $C_3$-$C_{12}$ cycloalkyl, aryl or 3-15 membered heterocyclyl are independently optionally further substituted by 1-3 groups selected from halide, $C_1$-$C_6$ alkyl, $C_1$-$C_6$ perfluoroalkyl, $C_1$-$C_6$alkoxyl, $C_1$-$C_6$alkylamino, CN or oxo;

each $R^a$, $R^b$ and $R^c$ is independently selected from H, $C_1$-$C_6$ perfluoroalkyl, $C_1$-$C_8$ alkyl, $C_2$-$C_8$ alkenyl, —($C_1$-$C_3$ alkylene)$_m$-($C_3$-$C_8$ cycloalkyl), —($C_1$-$C_3$ alkylene)$_m$-($C_3$-$C_8$ cycloalkenyl), $C_2$-$C_8$ alkynyl, —($C_1$-$C_3$ alkylene)$_m$-aryl, or —($C_1$-$C_3$ alkylene)$_m$-(3-8 member heterocyclyl), and each $R^a$, $R^b$ and $R^c$ is independently optionally further substituted by 0 to 3 groups selected from halide, hydroxyl, —CN, $C_1$-$C_8$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may optionally form a -(3-8 membered heterocyclyl), and the said ring is optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently —($C_1$-$C_3$ alkylene)-, —($C_2$-$C_6$ alkenylene)-, or —($C_2$-$C_5$ alkynylene)-;

each m is independently 0 or 1; and with the proviso that $R^2$, $R^3$, $R^4$ and $R^5$ are not all H In one embodiment of the invention, $R^7$ and $R^8$ are both methyl.

In another embodiment of the invention, X is N. In an alternative embodiment of the invention, X is C and is attached to $R^3$.

In one embodiment of the invention, Z is N.

In still another embodiment of the invention, $R^3$ is fluoro. In an alternative embodiment of the invention, $R^3$ is H, and at least one of $R^2$, $R^4$ or $R^5$ is a $C_1$-$C_6$alkyl.

In yet another embodiment of the invention, $R^1$ is an aryl. In an alternative embodiment of the invention, $R^1$ is a pyridine.

In one embodiment of the invention, $R^2$ or $R^4$ is methyl.

In another embodiment of the invention, $R^6$ together with $R^4$ cyclizes to form a 4- to 7-membered heterocyclyl ring fused to the piperazine to which they are attached and wherein the said heterocyclyl may independently be further substituted.

Xxx

In another embodiment, wherein $R^1$ is a 6-membered heterocyclyl. In a further aspect of this embodiment, $R^1$ is a pyridine or a piperazine.

In another embodiment, $R^1$ is a 5-membered heterocyclyl. In a further aspect of this embodiment, $R^1$ is selected from the group consisting of oxazole, isoxazole, thiazole or imidazole.

In another embodiment, $R^2$ or $R^4$ is methyl.

In another embodiment, $R^6$ is —$(R^d)_m$-(3-15 membered heterocyclyl). In a further aspect of this embodiment, $R^6$ is —$(R^d)_m$tetrahydropyran. In a still further aspect of this embodiment, $R^6$ is tetrahydro-2H-pyran-4-ylmethyl.

In an alternative embodiment, $R^6$ is —$(R^d)_m$—O$R^a$.

In another embodiment, $R^2$ is —$CH_3$ in (S) configuration. In a further aspect of this embodiment, $R^d$ is a —($C_1$-$C_3$alkylene)- and $R^a$ is either H or methyl.

The invention includes the following compounds or pharmaceutically acceptable salts thereof:

N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;

1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide; and N-(5-{[2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyl)pyridine-2-carboxamide.

The invention is further directed to a pharmaceutical composition comprising an effective amount of a compound according to any of the preceding claims, or a pharmaceutically acceptable salt thereof, and a pharmaceutically acceptable carrier.

The present invention further includes methods of treating diabetes mellitus and its complications, cancer, ischemia, inflammation, central nervous system disorders, cardiovascular disease, Alzheimer's disease and dermatological disease pression, viral diseases, inflammatory disorders, or diseases in which the liver is a target organ, the method comprising administering to a mammal an effective amount of a compound having Formula I above, or a pharmaceutically acceptable salt thereof. In another aspect of the invention, the method of treating is directed to ophthalmic complications. In a still further aspect of the invention, the diabetic complications comprise diabetic retinopathy (including diabetic macular edema), nephropathy and neuropathy.

DEFINITIONS

As used herein, the terms "comprising" and "including" are used in their open, non-limiting sense.

The term "alkyl", as used herein, unless otherwise indicated, includes saturated monovalent hydrocarbon radicals having straight or branched moieties.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "amino", as used herein, unless otherwise indicated, is intended to include the
—NH₂ radical, and any substitutions of the N atom.

The terms "halogen" and "halo", as used herein, unless otherwise indicated, represent chlorine, fluorine, bromine or iodine.

The term "trifluoromethyl", as used herein, unless otherwise indicated, is meant to represent a —CF₃ group.

The term "perfluoroalkyl", as used herein, is meant to represent an alkyl group in which all hydrogens attached to the carbons have been replaced by fluorine, such as CF₃, CF₂—CF₃, C(CF₂)(CF₂) and so on.

The term "trifluoromethoxy", as used herein, unless otherwise indicated, is meant to represent a —OCF₃ group.

The term "cyano", as used herein, unless otherwise indicated, is meant to represent a —CN group.

The term "CH₂Cl₂", as used herein, unless otherwise indicated, is meant to represent dichloromethane.

The term "$C_3$-$C_{12}$ cycloalkyl" or "$C_5$-$C_8$ cycloalkyl", as used herein, unless otherwise indicated, refers to a non-aromatic, saturated or partially saturated, monocyclic or fused, spiro or unfused bicyclic or tricyclic hydrocarbon referred to herein containing a total of from 3 to 12 carbon atoms, or 5-8 ring carbon atoms, respectively. Exemplary cycloalkyls include rings having from 3-10 carbon atoms, such as cyclopropyl, cyclobutyl, cyclopentyl, cyclohexyl, cycloheptyl, and adamantyl. Illustrative examples of cycloalkyl are derived from, but not limited to, the following:

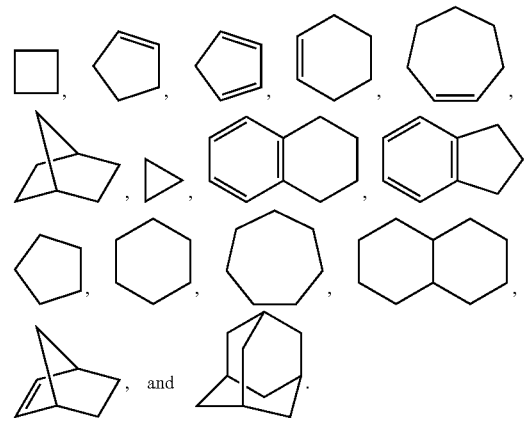

The term "aryl", as used herein, unless otherwise indicated, includes an organic radical derived from an aromatic hydrocarbon by removal of one hydrogen, such as phenyl or naphthyl.

The term "(3-15)-membered heterocycyl", "(3-8)-membered heterocyclyl", "(6-10)-membered heterocyclyl", or "(4 to 10)-membered heterocyclyl", as used herein, unless otherwise indicated, includes aromatic and non-aromatic heterocyclic groups containing one to four heteroatoms each selected from O, S and N, wherein each heterocyclic group has from 3-15, 3-8, 6-10, or 4 to 10 atoms, respectively, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Heterocycles include monocyclic and polycyclic aromatic ring structures, with "(5-12)-membered heteroaryls" referring to those that are heterocycles having 5 to 12 atoms in their ring system(s). Examples of "(5-12)-membered heteroaryls" are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The above-mentioned heterocyclic groups may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other Illustrative examples of 4 to 10 membered heterocyclic are derived from, but not limited to, the following:

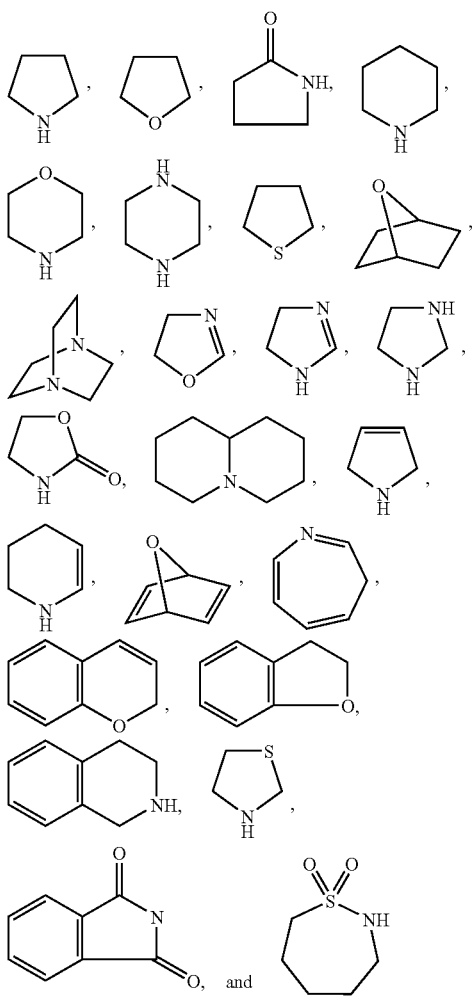

The term "(12-15)-membered heterocyclyl", as used herein, unless otherwise indicated, includes aromatic and non-aromatic heterocyclic groups that are in a partially fused or spirocyclic configuration and which contain at least one N and optionally additional 1 to heteroatoms each selected from O, S and N, wherein the heterocyclic group has from 12 to 15 atoms, respectively, in its system, and with the proviso that any ring of said group does not contain two adjacent O or S atoms. The heterocyclic groups include tricyclic fused ring and spirocyclic systems. An example of a 13-membered tricyclic heterocyclic group is 3,4-dihydropyrazino[1,2-a]benzimidazole and an example of a 15-membered spirocyclic heterocyclic group is 3,4-dihydro-1'H-spirochromene.

Unless otherwise indicated, the term "oxo" refers to =O.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

The phrase "pharmaceutically acceptable salt(s)", as used herein, unless otherwise indicated, includes salts of acidic or basic groups which may be present in the compounds of Formula I. The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "therapeutically effective amount", as used herein, refers to that amount of drug or pharmaceutical agent that will elicit the biological or medical response of a tissue, system, animal, or human that is being sought by a researcher, veterinarian, medical doctor or other.

The term "substituted" means that the specified group or moiety bears one or more substituents. The term "unsubstituted" means that the specified group bears no substituents. The term "optionally substituted" means that the specified group is unsubstituted or substituted by one or more substituents.

In accordance with convention, in some structural formula herein, the carbon atoms and their bound hydrogen atoms are not explicitly depicted e.g., represents a methyl group,

represents an ethyl group,

represents a cyclopentyl group, etc. The convention

denoted the point of attachment to the remainder of the compound, and the convention

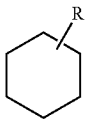

denotes that the R substituent may be attached at any of the available atoms on the given structure, here shown as a cyclohexyl, unless otherwise indicated. In the particular embodiment,

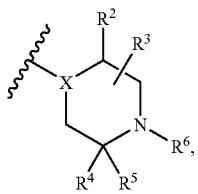

$R^3$ may be attached at any of the heteroatoms of the heterocycle, including X if X is C. In the particular pyrazolo intermediate embodiment,

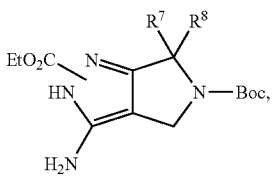

the acyl group may be attached to either of the two nitrogens of the fused pyrazole ring.

Certain compounds of Formula I may have asymmetric centers and therefore exist in different enantiomeric forms. All optical isomers and stereoisomers of the compounds of Formula I and mixtures thereof, are considered to be within the scope of the invention. With respect to the compounds of Formula I, the invention includes the use of a racemate, one or more enantiomeric forms, one or more diastereomeric forms, or mixtures thereof. The compounds of Formula I may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to, moieties described in Patini et al., Chem. Rev, 1996, 96, 3147-3176 and references cited therein.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention and pharmaceutically acceptable salts or solvates of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this invention thereof can generally be prepared by carrying out the procedures disclosed in the Schemes and/or in the Examples below, by substituting a readily available isotopically labeled reagent for a non-isotopically labeled reagent.

The term "mmol", as used herein, unless otherwise indicated, is intended to mean millimole. The term "equiv", as used herein, unless otherwise indicated, is intended to mean equivalent. The term "mL", as used herein, unless otherwise indicated, is intended to mean milliliter. The term "U", as used herein, unless otherwise indicated, is intended to mean units. The term "mm" as used herein, unless otherwise indicated, is intended to mean millimeter. The term "g", as used herein, unless otherwise indicated, is intended to mean gram. The term "kg", as used herein, unless otherwise indicated, is intended to mean kilogram. The term "h", as used herein, unless otherwise indicated, is intended to mean hour. The term "min", as used herein, unless otherwise indicated, is intended to mean minute. The term "µL", as used herein, unless otherwise indicated, is intended to mean microliter. The term "µM", as used herein, unless otherwise indicated, is intended to mean micromolar. The term "µm", as used herein, unless otherwise indicated, is intended to mean micrometer. The term "M", as used herein, unless otherwise indicated, is intended to mean molar. The term "N", as used herein, unless otherwise indicated, is intended to mean normal. The term "nm", as used herein, unless otherwise indicated, is intended to mean nanometer. The term "nM", as used herein, unless otherwise indicated, is intended to mean nanoMolar. The term "amu", as used herein, unless otherwise indicated, is intended to mean atomic mass unit. The term "C", as used herein, unless otherwise indicated, is intended to mean Celsius. The term "m/z", as used herein, unless otherwise indicated, is intended to mean, mass/charge ratio. The term "wt/wt", as used herein, unless otherwise indicated, is intended to mean weight/weight. The term "v/v", as used herein, unless otherwise indicated, is intended to mean volume/volume. The term "mL/min", as used herein, unless otherwise indicated, is intended to mean milliliter/minute. The term "UV", as used herein, unless otherwise indicated, is intended to mean ultraviolet. The term "APCI-MS", as used herein, unless otherwise indicated, is intended to mean atmospheric pressure chemical ionization mass spectroscopy. The term "HPLC", as used herein, unless otherwise indicated, is intended to mean high performance liquid chromatograph. The chromatography was performed at a temperature of about 20° C., unless otherwise indicated. The term "LC", as used herein, unless otherwise indicated, is intended to mean liquid chromatograph. The term "LCMS", as used herein, unless otherwise indicated, is intended to mean liquid chromatography mass spectroscopy. The term "TLC", as used herein, unless otherwise indicated, is intended to mean thin layer chromatography. The term "SFC", as used herein, unless otherwise indicated, is intended to mean supercritical fluid chromatography. The term "sat" as used herein, unless otherwise indicated, is intended to mean saturated. The term "aq" as used herein, is intended to mean aqueous. The term "ELSD" as used herein, unless otherwise indicated, is intended to mean evaporative light scattering detection. The term "MS", as used herein, unless otherwise indicated, is intended to mean mass spectroscopy. The term "HRMS (ESI)", as used herein, unless otherwise indicated, is intended to mean high-resolution mass spectrometry (electrospray ionization). The term "Anal.", as used herein, unless otherwise indicated, is intended to mean analytical. The term "Calcd", as used herein, unless otherwise indicated, is intended to mean calculated. The term "N/A", as used herein, unless otherwise indicated, is intended to mean not tested. The term "RT" or "rt" as used herein, unless otherwise indicated, is intended to mean room temperature. The term "Mth.", as used herein, unless otherwise indicated, is intended to mean Method. The term Celite®, as used herein, unless otherwise indicated, is intended to mean a white solid diatomite filter agent commercially available from World Minerals located in Los Angeles, Calif. USA. The term "Eg.", as used herein, unless otherwise indicated, is intended to mean example.

The term "$K_i$", as used herein, unless otherwise indicated, is intended to mean values of enzyme inhibition constant. The term "$K_i$ app", as used herein, unless otherwise indicated, is intended to mean $K_i$ apparent. The term "$IC_{50}$", as used herein, unless otherwise indicated, is intended to mean concentrations required for at least 50% enzyme inhibition.

Other aspects, advantages, and features of the invention will become apparent from the detailed description below.

DETAILED DESCRIPTION AND EMBODIMENTS OF THE INVENTION

The following reaction Schemes illustrate the preparation of the compounds of the present invention. Unless otherwise indicated, $R^1$ through $R^{12}$ and $R^a$ through $R^e$ in the reaction schemes and the discussion that follows are as defined above.

DETAILED DESCRIPTION

Compounds of Formulas I can be made following the synthetic routes in Scheme 1 through Scheme 5. In the following schemes and examples, the terms, "BOC", "Boc" or "boc" means N-tert-butoxycarbonyl, "BOP" means benzotriazol-1-yloxytris(dimethylamino)phosphonium hexafluorophosphate, "DCM" means $CH_2Cl_2$, DIPEA (also known as Hunig's base) means diisopropyl ethyl amine, "DMA" means dimethyl amine, "DMF" means dimethyl formamide, "DMSO" means dimethylsulfoxide, "Me" means methyl —$CH_3$, "Et" means —$CH_2CH_3$, "MTBE" means methyl t-butyl ether, TEA means triethyl amine, TFA means trifluoro acetic acid, THF means tetrahydrofuran and "SEM" means 2-(trimethylsilyl)ethoxymethyl, "HATU" means 2-(7-Aza-1H-benzotriazole-1-yl)-1,1,3,3-tetramethyluronium hexafluorophosphate.

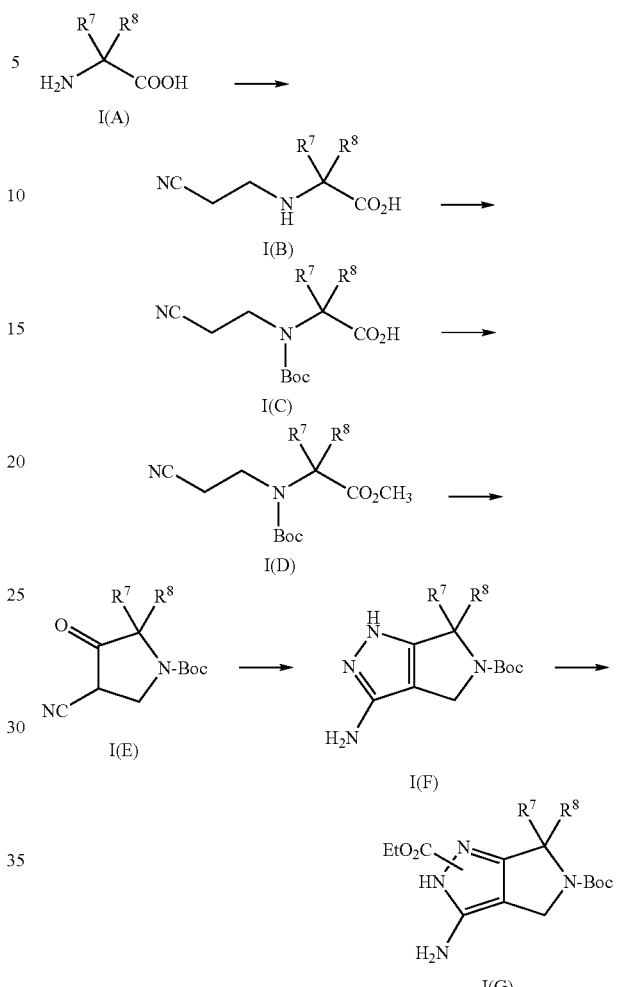

Scheme 1 illustrates the synthesis of the intermediates I(A) through I(G), which are useful in preparation of compounds of Formula I. The amino group of the substituted amino acid I(A) is alkylated to give compound I(B). This can typically be done by treating compound I(A) with an alkylating agent in the presence of a base. An activated electrophilic double bond moiety is a commonly used alkylating reagent. A typical reaction condition of alkylating I(A) with an activated electrophilic double bond moiety is to treat I(A) with the activated double bond moiety in the presence of a strong base. Subsequent aqueous work up affords compound I(B). The amino group of compound I(B) is then protected with a boc group to give compound I(C). This can typically be done by treating compound I(B) with Boc agent in the presence of a base. A typical condition is to treat compound I(B) with $(Boc)_2O$ in the presence of $Me_4NOH$ in MeCN as a solvent. The carboxylic acid group of compound I(C) is then converted into a methyl ester of compound I(D). A typical condition of converting the carboxylic acid group into the methyl ester group is to treat I(C) with methyl iodide in DMF in the presence of a base. Compound I(D) then undergoes an intramolecular aldol condensation to give compound I(E). This can typically be done by treating compound I(D) with a strong base in an aprotic solvent. A typical condition is to treat compound I(O) with t-BuOK in toluene. Subsequent aqueous workup gives compound I(E). Compound I(E) then undergoes a 2+3 cyclization with a hydrazine moiety to form compound I(F). A typical condition of the cyclization is to reflux compound I(E) with hydrazine and acetic acid in EtOH. The free base pyrazole nitrogen of compound I(F) is then acylated to give compound I(G). A typical condition of the acylation is to treat compound I(F) with chloro ethyl carbonate in THF. As indicated in the above structure for I(G), the acyl group can be attached to either of the nitrogens of the pyrazole.

More detailed synthetic conditions to intermediate I(G) of Scheme 1 can be found in U.S. Patent Application Publication No. 2003/0171357 and PCT Publication WO 02/12242, the disclosures of which are incorporated herein by reference.

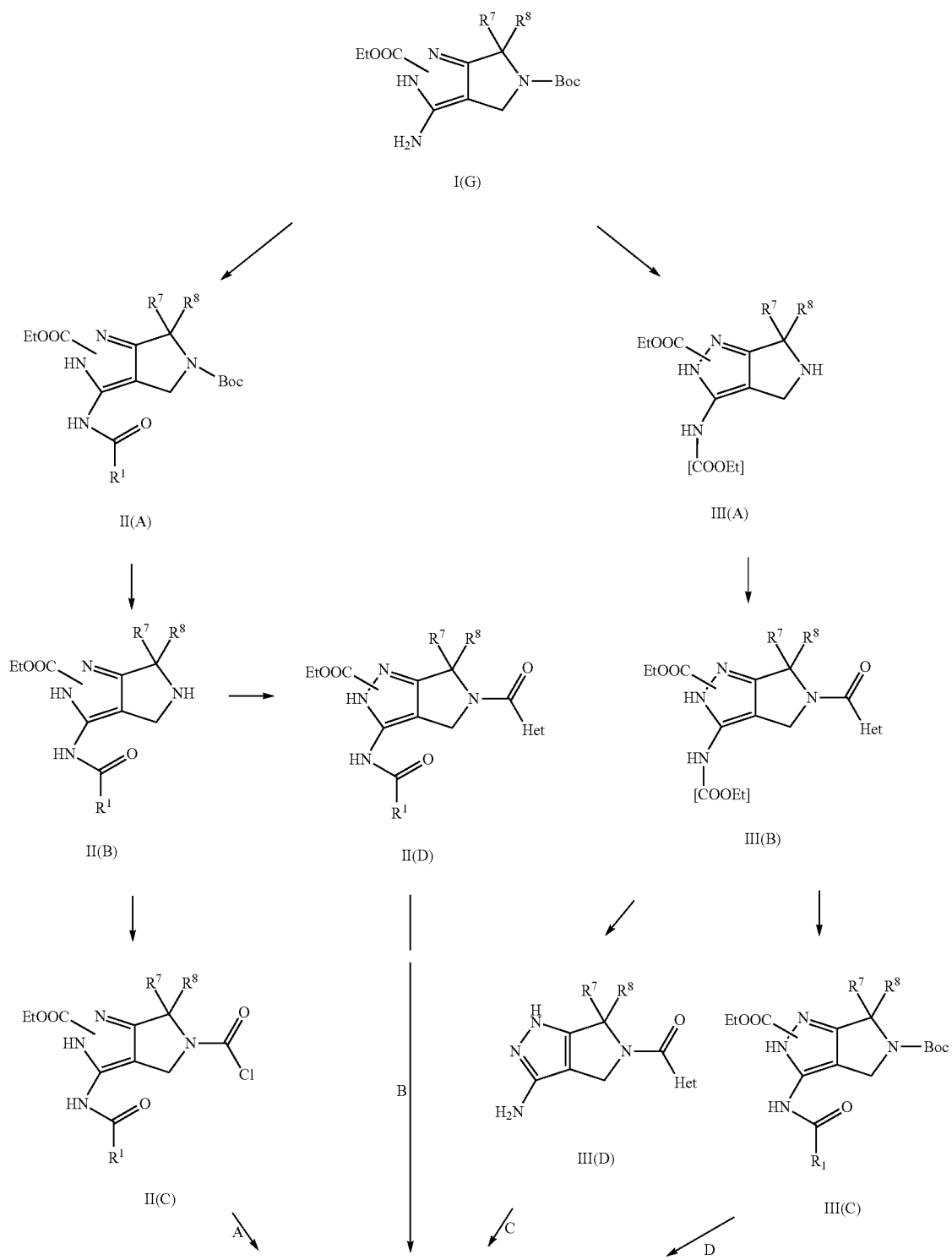

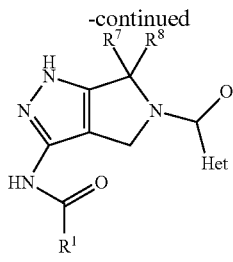

I

Scheme 2 illustrates several routes through which compounds of Formula I can be made from intermediate I(G). The substituents $R^1$, $R^7$ and $R^8$ are as defined in Formula I above. The term "Het" is the piperazine or piperidine heterocyclic group as defined by

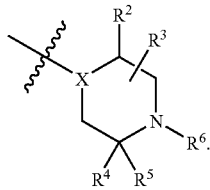

In one route of Scheme 2, compound I(G) undergoes a nucleophilic reaction with an $R^1$ electrophile moiety. This nucleophilic reaction can be any acylation carried out by an amine functionality. A typical acylation reaction condition is to treat compound I(G) with an acylating agent such as $R^1$—COCl, in the presence of a base such as 2 equivalents of DIPEA, in a solvent such as dichloromethane. The reaction mixture is stirred at a temperature between 0° C. and room temperature for about 12 hours. Subsequent aqueous workup gives compound II(A). The Boc group on the pyrrole nitrogen of compound II(A) is then removed to give compound II(B). This can typically be done by treating II(A) with a strong acid. A typical reaction condition is to treat compound II(A) with 4N HCl in dioxane and DCM. Subsequent aqueous workup affords compound II(B). The pyrrole NH of compound II(B) is then converted to the chloroformate II(C). This can typically be done by using phosgene, triphosgene, or some other equivalent. A typical reaction condition is to treat II(B) with 2 equivalents of triphosgene in DCM at 0° C. for four hours. Subsequent mild basic workup with saturated $NaHCO_3$ and purification gives compound II(C). Compound II(C) is then treated with a nucleophile moiety. The nucleophile can be any amine that can react with the electrophile II(C). A typical reaction involves treating II(C) with a nucleophile such as 1.5 equivalents of an amine in the presence of 1 equivalent of base such as DIPEA in a solvent such as THF. Subsequent deprotection of ethoxy carbonyl group in a protic solvent, such as methanol, in the presence of base, such as TEA, followed by purification gives a compound of Formula I.

Alternatively, compound II(B) can then undergo a nucleophilic reaction with a Het electrophile to give compound II(D). The nucleophilic reaction carried out for this transformation can be an acylationn. An acylation reaction of II(B) to give II(D) is carried out by treating compound II(B) with an acylating reagent in the presence of base. A typical reaction condition is to mix compound II(B) with an excess of base, such as DIPEA in DCM, followed by addition of the resulting solution to an acylchloride at 0° C. The reaction is stirred for about 2 hours at room temperature and subsequent aqueous workup gives compound II(D). The ethoxycarbonyl protecting group on the pyrazole nitrogen of compound II(D) is removed to give a compound of Formula I. This can typically be done by treating a compound II(D) with a base. A typical reaction condition is to treat compound III(B) in a protic solvent, such as methanol, in the presence of base, such as TEA, or to treat a compound II(D) in MeOH in the presence of 2-3 equivalents of NaOH at room temperature. Subsequent aqueous workup affords a compound of Formula I.

In an alternate route of Scheme 2, the Boc group on the pyrrole nitrogen is removed to give compound III(A). The reaction can typically be carried out by treating compound I(G) with a strong acid. A typical reaction condition is to treat compound I(G) with 4N HCl in dioxane and DCM. Subsequent aqueous workup affords compound III(A). Compound III(A) can then undergo a nucleophilic reaction with a Het electrophile to give compound III(B). Because the —$NH_2$ group attached to the pyrazole in compound III(A) is less reactive than the pyrrole nitrogen of III(A), the transformation of III(A) to III(B) can be carried out without protecting the pyrazole —$NH_2$ group of compound III(A). The nucleophilic reaction carried out for this transformation can be an acylation, Relative mild reaction conditions are preferred to achieve reaction selectivity. An acylation reaction of III(A) to give III(B) is carried out by treating III(A) with an acylating reagent in the presence of base. A typical reaction condition is to mix compound III(A) with an excess of base, such as DIPEA in DCM, and adding the resulting solution to an acyl chloride at 0° C. The reaction mixture is held at 0° C. for about two hours and subsequent aqueous workup gives compound III(B).

Compound III(B) then undergoes a nucleophilic reaction with an $R^1$ electrophile moiety. This nucleophilic reaction can be an acylation that an amine functionality carries out. A typical acylation reaction condition is to treat compound III(B) with an acylating agent, such as RCOCl in the presence of a base, such as 2 equivalents of DIPEA, in a solvent, such as 1,2-dichloroethane. Subsequent aqueous workup gives compound III(C). The ethoxycarbonyl protecting group on the pyrazole nitrogen of compound III(C) is removed, typically with a base, to give the free base of compounds of Formula I. A typical reaction condition is to mix compound III(C) with TEA in a protic solvent, such as methanol, followed by purification to give a compound of Formula I.

Alternatively, the ethoxycarbonyl protecting group on the pyrazole nitrogen of compound III(B) is removed to give the free base compound III(D). This can typically be done by treating compound III(B) with a base. A typical reaction condition is to reflux compound III(B) in dioxane and DCM in the presence of 2-3 equivalents of LiOH. Subsequent aqueous workup affords compound III(D). Compound III(D) then undergoes a nucleophilic reaction with an $R^1$ electrophile moiety. This nucleophilic reaction can be an acylation that an amine functionality carries out. A typical acylation reaction condition is to treat compound III(D) with an acylating agent, such as $R^1$—COCl, in the presence of a base, such as 2 equivalents of DIPEA, in a solvent such as dichloromethane. The reaction mixture is stirred for four hours and subsequent aqueous workup and purification gives a compound of Formula I.

In a method similar to Route B described above, compounds of Formula I can also be synthesized by the following method in Scheme 3.

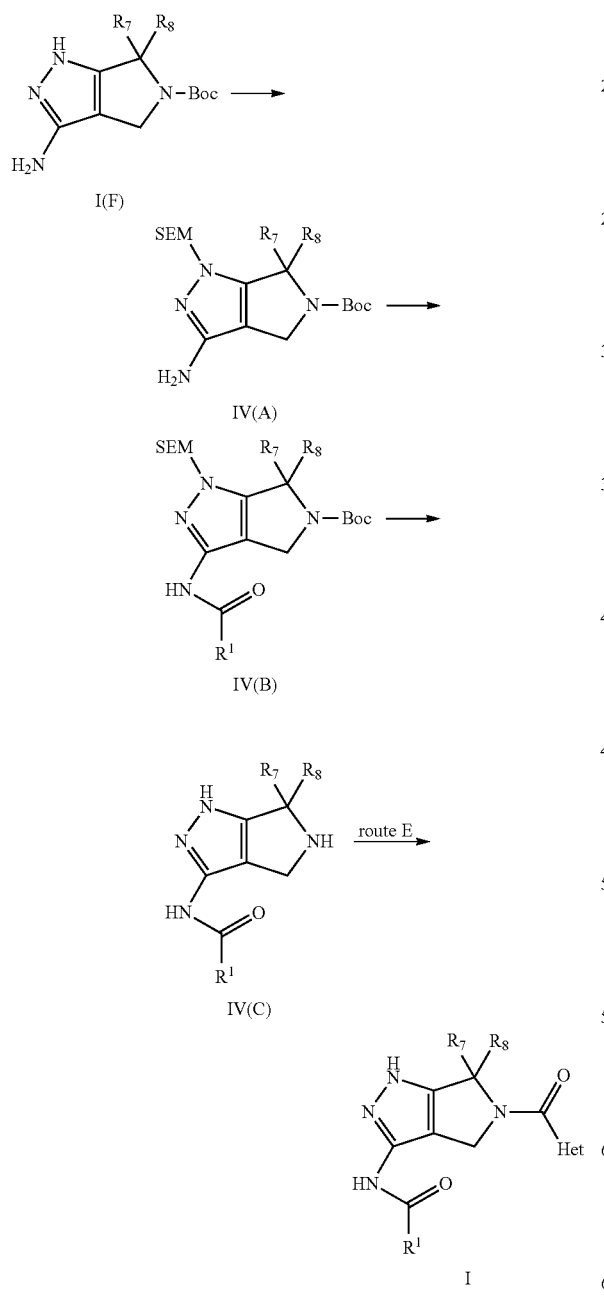

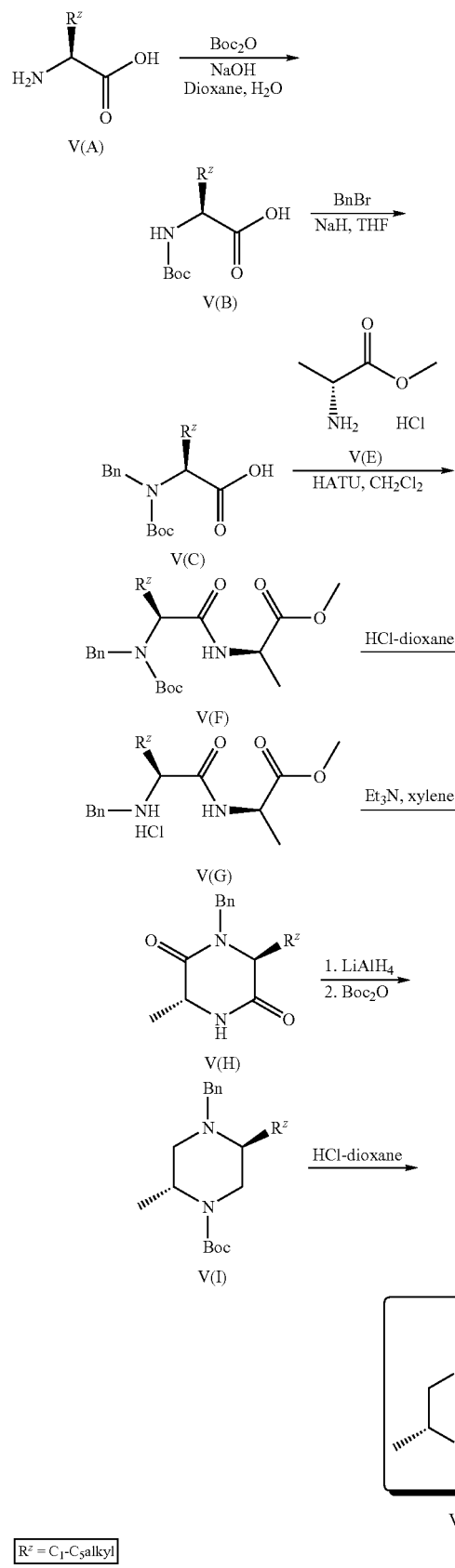

-continued

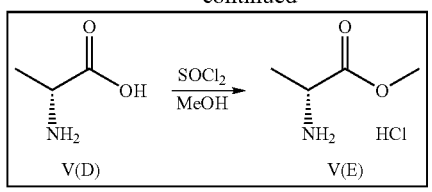

Intermediate V(B) was prepared by mixing a solution of V(A) (267 g, 3 mol) in dioxane (6 L), H$_2$O (3 L) and 1 M NaOH (3 L) and cooling in an ice-water bath. Boc$_2$O (720 g, 3 mol) was added at 0-10° C. and stirring was continued at room temperature overnight. The solvent was removed in vacuum. 3 L of H$_2$O was added to dissolve the residue. The resulting solution was cooled to 0-5° C. and acidified with 1 N HCl to pH=3. The resulting solution was extracted with ethyl acetate (1.5 L×3). The organic phases were combined, dried over Na$_2$SO$_4$ and concentrated to give compound V(B) (465 g, 82%) as a white solid. (R$^a$=CH$_3$: $^1$H NMR (400 MHz, CDCl$_3$) δ 11.30(br, 1H), 6.90(br, 0.5H), 5.10(br, 0.5H), 4.50-4.00(m, 1H), 1.40(m, 12H))

In the next step, the intermediate V(C) was subsequently prepared by suspending NaH (200 g, 5 mol) in 2.5 L of dry THF and cooling the mixture to ±10-0° C. A solution of V(B) (94.5 g, 0.5 mol) in 800 mL of dry THF was added dropwise at ±10-0° C. After the addition, the mixture was stirred at −10-0° C. for 30 minutes. Then BnBr (478 mL, 4 mol) was added dropwise at −10-0° C. The reaction mixture was stirred at rt for 60 hours. The mixture was poured into 3 L of ice water carefully. The resulting solution was washed with 1.5 L of diethyl ether. The aqueous phase was acidified with 2 N aq. HCl to pH=3-4 at 0-5° C. and extracted with diethyl ether (1.5 L×2). The combined organic layers were dried over Na$_2$SO$_4$ and evaporated in vacuum to give compound V(C) (115 g, 84%) as a yellow solid. (R$^a$=CH$_3$: $^1$H NMR (400 MHz, CDCl3) δ 9.50(br, 1H), 7.38(m, 5H), 4.63-3.95(m, 3H), 1.51 (m, 12H)).

In a separate reaction, the intermediate reagent V(E) was prepared by suspending V(D) (100 g, 1.12 mol) in 1 L of MeOH. The mixture was cooled to 0-5° C. 50 mL of SOCl$_2$ was added dropwise at 0-5° C. The reaction mixture was then stirred at rt for 24 hours. The mixture was evaporated in vacuum to give compound V(E) (141 g, 90%) as a white solid.

Intermediate V(F) was prepared from V(C) and V(E). Compound V(C) (100 g, 0.358 mol) and DIPEA (138 g, 1.07 mol) were dissolved in 900 mL of DMF. The mixture was cooled to 0-10° C. Then HATU (150 g, 0.394 mol) was added to the mixture portionwise at 0-10° C. The resulting mixture was stirred at 0-10° C. for 10 minutes.

Compound V(E) (55 g, 0.394 mol) was added portionwise at 0-10□. The reaction mixture was stirred at rt overnight. The solvent was removed in vacuum and the residue was dissolved in 500 mL of water. The resulting mixture was extracted with ethyl acetate (300 mL×3). The organic phases were combined, dried over Na$_2$SO$_4$ and concentrated in vacuum. The residue was purified by chromatography via silica gel eluted with petroleum ether/ethyl acetate (50:1~10:1) to give compound V(F) (100 g, 76%) as a yellow oil.

Compound V(F) (100 g, 0.274 mol) was dissolved in 2 L of 4 N HCl (g)/dioxane at 0-5° C. The mixture was stirred at rt overnight and concentrated in vacuum to give compound V(G) (85 g, 100%) as a colorless syrup. (R$^z$=CH$_3$: $^1$H NMR (400 MHz, D2O) δ 7.41(m, 5H), 4.38(m, 1H), 4.14(m, 2H), 3.93(m, 1H), 3.69(s, 3H), 1.44(d, J=6.8 Hz, 3H), 1.35(d, J=7.2 Hz, 3H)).

In the next step, V(G) (75 g, 0.25 mol) and Et$_3$N (41.7 mL, 0.3 mol) were suspended in 1500 mL of xylene. The mixture was stirred at it for 30 minutes. Then DMAP was added as catalyst and the mixture was heated to reflux for 48 hours. The solvent was removed in vacuum and the residue was purified by chromatography on silica gel eluted with petroleum ether/ethyl acetate (50:1~10:1) to give compound V(H) (47 g, 81%) as a brown oil. (R$^z$=CH$_3$: $^1$H NMR (400 MHz, CDCl3) δ 7.71(br, 1H), 7.33(m, 5H), 5.16(d, J=14.8 Hz, 1H), 4.13(m, 2H), 3.86(m, 1H), 1.59(d, J=12.8 Hz, 3H), 1.38(d, J=8.8 Hz, 3H)).

LiAlH$_4$ (31 g, 0.82 mol) was suspended in 200 mL of dry THF. A solution of compound V(H) (47 g, 0.203 mol) in 600 mL of dry THF was added dropwise. After the addition, the mixture was heated to reflux overnight. The reaction mixture was cooled to 0-5° C. and diluted with 300 mL of THF. 190 mL of 20% aqueous NaOH was added dropwise to the reaction mixture. After the addition, the mixture was stirred at room temperature for 30 minutes. (Boc)$_2$O (66.5 g, 0.31 mol) was added to the mixture. The mixture was stirred at rt overnight. The solvent was removed in vacuum and the residue was purified by chromatography via silica gel eluted with petroleum ether/ethyl acetate (100:1) to give compound V(J) (48 g, 77%) as a pale yellow liquid. (R$^z$=CH$_3$: $^1$H NMR (400 MHz, CDCl3) δ 7.36(m, 5H), 4.19(m, 1H), 3.67 (m, 2H), 3.47 (m, 1H), 3.33(m, 1H), 2.97(m, 1H), 2.72(m, 1H), 2.27(d, J=25.6 Hz, 1H), 1.48(s, 9H), 1.36(d, J=6.4 Hz, 3H), 0.99(d, J=7.2 Hz, 3H)).

In the final step, V(I) (48 g, 0.158 mol) was dissolved in 1500 mL of 4 N HCl (g)/dioxane and the resulting solution was stirred at rt overnight. The solvent was removed in vacuum and the residue was triturated with 500 mL of diethyl ether. The solid formed was filtered and the filter cake was washed with 50 mL of diethyl ether, then dried in vacuum to give V(J) (37 g, 100%) as a white solid. (R$^z$=CH$_3$: $^1$H NMR (400 MHz, CDCl3) δ 7.42(s, 5H), 4.82(d, J=17.6 Hz, 1H), 4.10(d, J=17.6 Hz, 1H), 3.71-2.98(m, 6H), 1.56(d, J=8.0 Hz, 3H), 1.20(d, J=8.8 Hz, 3H).)

Spirocyclic piperazine derivatives such as in Example A2, can be prepared using analogous methods to the above scheme, wherein R$^z$ is a C$_2$-C$_5$alkyl.

Scheme 5 (Bicyclic Piperazine Intermediates)

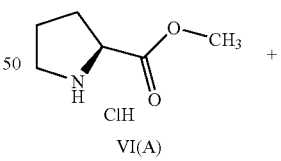

VI(A)

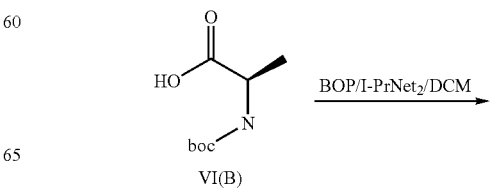

VI(B)

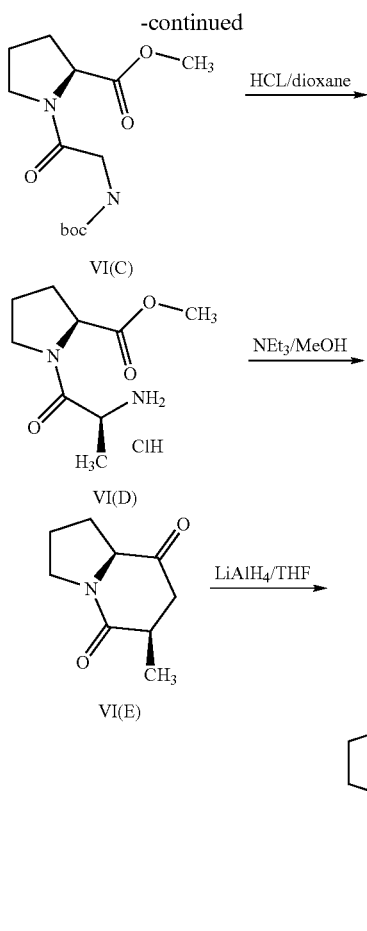

The intermediate VI(C) was prepared by mixing N-(tert-Butoxycarbonyl)-D-alanine VI(B) (114.23 g, 0.0.603 mol), methyl L-prolinate VI(A) (100 g, 0.603 mol), BOP (291.72 g, 0.66 mol), and dichloromethane (1.5 L) in a 2 L flask. DIPEA (193 g, 1.5 mol) was added dropwise under stirring and cooling on a water bath. The reaction mixture was stirred overnight at room temperature and evaporated. Water (1 L), ethyl acetate (400 mL), and ether (400 mL) were added. After extraction, the organic layer was separated. The aqueous one was washed with ether (300 mL). The combined extracts were washed with 1 M HCl (1 L), water (1 L), 10% $K_2CO_3$ (2×1 L), dried with anhydrous $Na_2SO_4$, and evaporated. A viscous oil VI(C) (110 g, 61%) was obtained.

The intermediate VI(C) (110 g, 0.366 mol) was treated with 4 M HCl in dioxane (~400 mL). The solution was kept for 16 h at room temperature and evaporated. The oily residue was washed with ether (2×500 mL). The ether was decanted, and the oil VI(D) was dried in vacuum.

Intermediate VI(D) was dissolved in absolute methanol (700 mL). Triethylamine (105 mL, 0.75 mol) was added to pH ~8-9. The reaction mixture was stirred overnight at room temperature. The solution was evaporated. The solid residue was stirred in dichloromethane/ethyl acetate mixture (1:1, 600 mL), and the obtained mixture was washed with 40% aqueous potash (500 mL). The aqueous layer was subjected to extraction with dichloromethane/ethyl acetate mixture (1:1, 2×300 mL). The combined extracts were dried with potash and evaporated. The solid residue was treated with ether (400 mL). The resulting mixture was kept for 2 h at room temperature, then overnight at 4° C. The formed crystals were washed with cold ether (100 mL) and vacuum-dried to afford VI(E) (48.1 g, 78.08%). $^1$H NMR spectrum is attached (see LJMT0165-07_Additional_WC_Data folder).

Intermediate VI(E) (48.1 g, 0.286 mol) was suspended in THF (600 mL). This suspension was added to a solution of $LiAlH_4$ (27.2 g, 0.715 mol) in THF (300 mL) in a flow of argon under stirring and heating at such a rate that the solvent simmer. After this, the reaction mixture was refluxed for 15 h, cooled to room temperature, and treated with 5 M NaOH (200 mL). The organic layer was separated, and the curds-like residue was washed with ether (3×100 mL.). The combined extracts were dried with anhydrous $K_2CO_3$ and evaporated. The liquid residue was distilled in vacuum (72-75° C./10 mmHg). Yield: 75.2% (30.1 g). Satisfactory C, H, N-analysis was obtained.

EXAMPLES

The invention will now be described in reference to the following examples. These examples are not to be regarded as limiting the scope of the present invention, but shall only serve in an illustrative manner. The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The structures of the compounds are confirmed by either elemental analysis or NMR, where peaks assigned to the characteristic protons in the title compound are presented where appropriate. $^1$H NMR shift ($\delta_H$) are given in parts per million (ppm) down field from an internal reference standard. Unless otherwise shown, NMR data is provided in Table 1 below.

Example A1

N-(6,6-Dimethyl-5((3S,8aS)-3-methyl-octahydropyrrolo[1,2-a]pyrazine-2-carbonyl)-1,4,5,6-tetrahydropyrrolo[3,4-c]pyrazol-3-yl)picolinamide

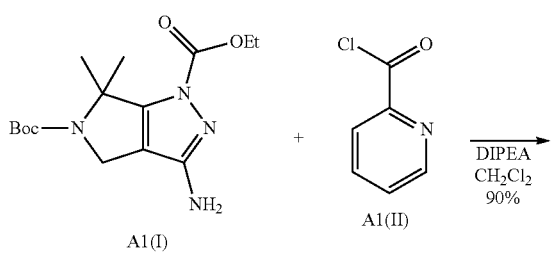

23

-continued

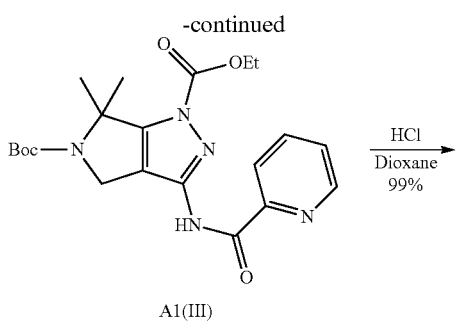

A1(III)

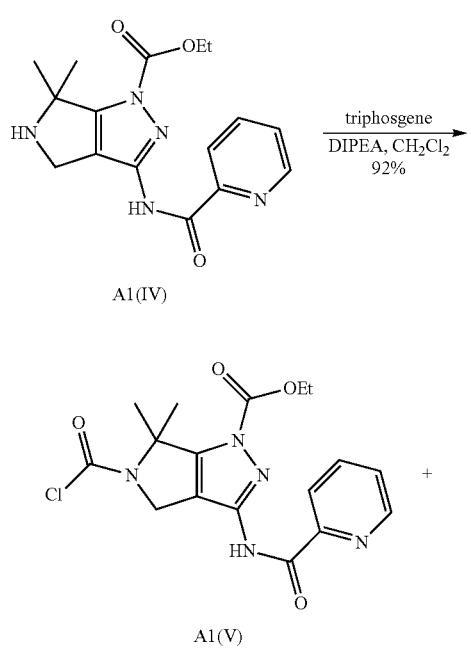

A1(IV)

A1(V)

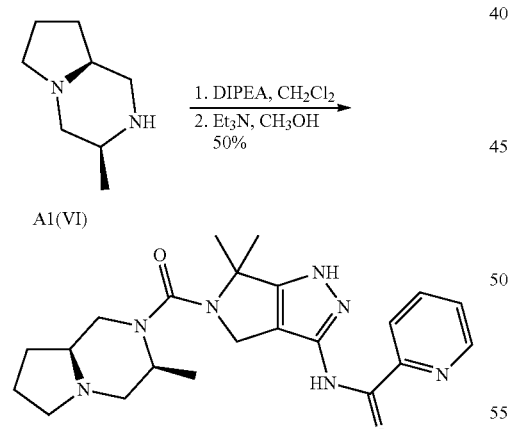

A1(VI)

A1

Intermediate A1(III)

5-tert-Butyl 1-ethyl 6,6-dimethyl-3-(picolinamido) pyrrolo[3,4-c]pyrazole-1,5(4H,6H)-dicarboxylate To a solution of 5-tert-butyl 1-ethyl 3-amino-6,6-dimethyl-4,6-dihydropyrrolo[3,4-c]pyrazole-1,5-dicarboxylate, A1(I), (7.32 g, 22.56 mmol) and DIPEA (12 mL) in $CH_2Cl_2$ (60 mL), picolinoyl chloride hydrochloride, A1(II), (4.82 g, 27.07 mmol) was added slowly. The reaction was stirred at room temperature for 2 hrs. The reaction mixture was diluted with $CH_2Cl_2$ (50 mL), washed with water (2×30 mL), sat. NaCl (brine), and dried over $MgSO_4$, filtered and concentrated to give A1(III) (9.12 g, 94% yield). $^1H$ NMR (400 MHz, $CDCl_3$-d) δ ppm 1.39-1.50 (m, 2 H) 1.49-1.58 (m, 10 H) 1.72 (s, 3 H) 1.78 (s, 3 H) 4.63 (q, J=7.07 Hz, 2 H) 4.81 (d, J=19.45 Hz, 2 H) 7.46-7.58 (m, 1 H) 7.82-7.97 (m, 1 H) 8.25 (dd, J=7.71, 3.41 Hz, 1 H) 8.73 (dd, J=9.60, 4.55 Hz, 1 H).

Intermediate A1(IV)

Ethyl 6,6-dimethyl-3-(picolinamido)-5,6-dihydropyrrolo[3,4-c]pyrazole-1(4H)-carboxylate dihydrochloride Intermediate A1(III) was dissolved in 4N HCl in 1,4-dioxane (80 mL). The reaction was stirred at room temperature for 16 hr. The solvent was concentrated to give A1(IV) (8.97 g, 99% yield). $^1H$ NMR (400 MHz, $CD_3OD$) ppm 1.52 (t, J=7.20 Hz, 3 H) 1.78 (s, 6 H) 4.60 (q, J=7.24 Hz, 2 H) 4.85 (s, 2 H) 7.60-7.74 (m, 1 H) 8.00-8.12 (m, 1 H) 8.23 (d, J=7.83 Hz, 1 H) 8.69-8.84 (m, 1 H).

Intermediate A1(V)

Ethyl 5-(chlorocarbonyl)-6,6-dimethyl-3-(picolinamido)-5,6-dihydropyrrolo[3,4-c]pyrazole-1(4H)-carboxylate To a cooling bath (0° C.) of A1(IV) (5.0 g, 12.43 mmol) and DIPEA (11 mL) in $CH_2Cl_2$ (50 mL), triphosgene (9.22 g, 31.08 mmol) in $CH_2Cl_2$ (20 mL) was added slowly. The reaction was stirred at room temperature for 2 hrs. The reaction mixture was diluted with $CH_2Cl_2$ (50 mL), washed with water (2×50 mL), sat. NaCl (brine) dried over $MgSO_4$ and concentrated. The residue was dissolved in minimal amount of acetone and water was added to precipitate. The compound was filtered and washed with water to give A1(V) (4.48 g, 92% yield). $^1H$ NMR (400 MHz, DMSO-$d_6$) δ ppm 1.40 (t, J=7.07 Hz, 3 H) 1.69 (s, 6 H) 4.51 (q, J=7.07 Hz, 2 H) 5.03 (s, 2 H) 7.76 (dd, J=7.45, 4.93 Hz, 1 H) 8.04-8.17 (m, 1 H) 8.18-8.32 (m, 1 H) 8.78 (d, J=4.80 Hz, 1 H) 12.15 (s, 1 H).

Compound A1

N-(6,6-Dimethyl-5-((4(3S,8aS)-3-methyl-octahydropyrrolo[1,2-a]pyrazine-2-carbonyl)-1,4,5,6-tetrahydropyrrolo[3,4-c]pyrazol-3-yl)picolinamide A solution of A1(IV) (4.48 g, 11.4 mmol), (3S,8aS)-3-methyl-octahydropyrrolo[1,2-a]pyrazine (2.40 g, 17.1 mmol), and DIPEA (7 mL) in THF (50 mL) was heated to 80° C. for 2 hrs. THF was concentrated. The reaction mixture was dissolved in $CH_3OH$ (30 mL) and $Et_3N$ (30 mL) then stirred at room temperature for 16 hrs. The residue was purified by HPLC (10% ACN(0.1% AcOH)-30% ACN(0.1% AcOH)) to give the title compound A1(3.01 g, 62% yield).

Example A2

N-(5-{[(8S)-6,8-dimethyl-6,9-diazaspiro[4.5]dec-9-yl]carbonyl}-6,6-dimethyl-1,4,5,6-tetrahydropyrrolo[3,4-c]pyrazol-3-yl)pyridine-2-carboxamide

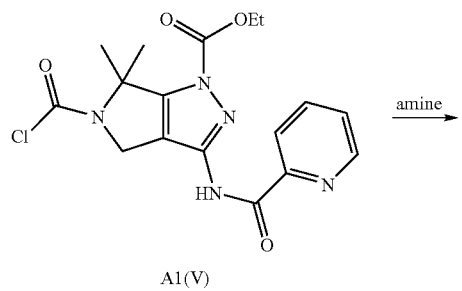

A1(V)

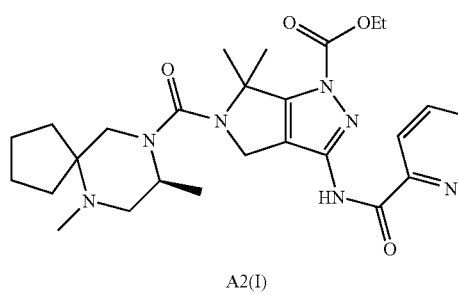

A2(I)

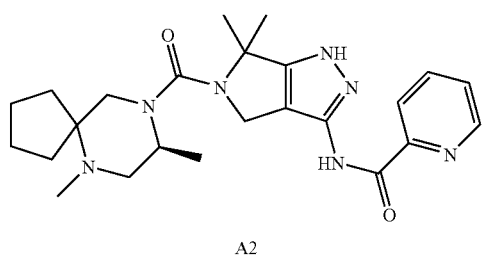

A2

The intermediate of A2(I), was prepared from A1(V) in a manner analogous to the preparation of A1 above, except (8S)-6,8-dimethyl-6,9-diazaspiro[4,5]decane was substituted in place of A1(VI). To the resulting suspension of A2(I) (668 mg, 1.28 mmol) in 30 mL methanol was added sodium hydroxide (3 mL of 10% solution in methanol). After stirring at room temperature for 30 minutes, the solvent was removed in vacuo. Purification as in example A1 afforded the title compound A2 as a white solid (254 mg, 29%).

Examples A3-A141

Examples A3 through A141 were prepared using methods analogous to Examples A1 and A2 above.

Example A142

N-((5-(((2R,5S)-1-(3-fluoropropyl)-2,5-dimethylpiperazine-4-carbonyl)-6,6-dimethyl-1,4,5,6-tetrahydropyrrolo[3,4-c]pyrazol-3-yl)picolinamide

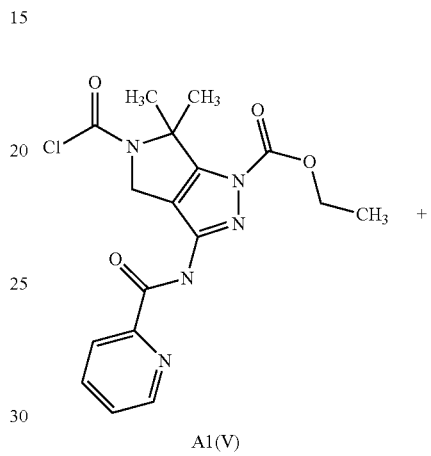

A1(V)

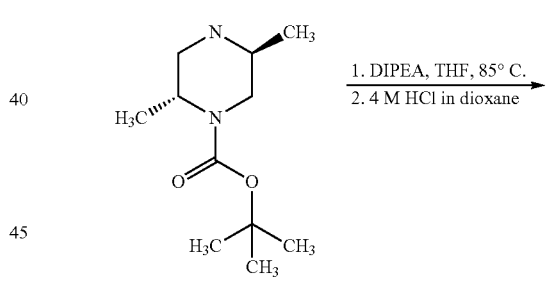

A142(I)

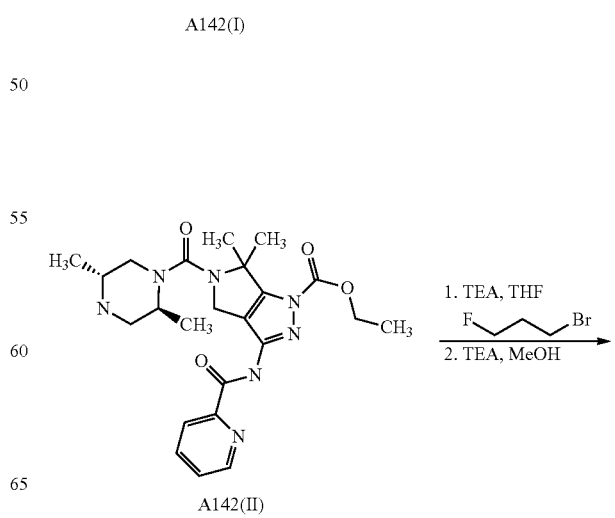

A142(II)

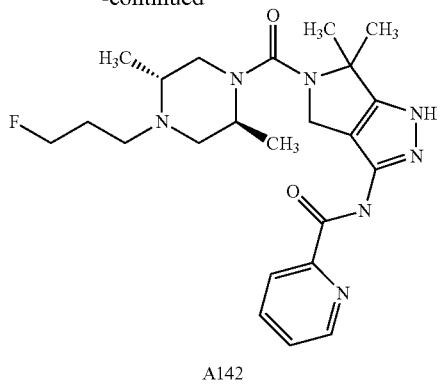

A142

Intermediate A142(II)

Ethyl 5-((2S,5R)-2,5-dimethylpiperazine-1-carbonyl)-6,6-dimethyl-3-(picolinamido)-5,6-dihydropyrrolo[3,4-c]pyrazole-1(4H)-carboxylate To a sealed tube was added the piperazine A142(I) (1.0 g, 2.4 mmol, 1.0 equiv), tetrahydrofuran (50.0 mL), the A1(V) (0.627 g, 2.93 mmol, 1.2 equiv) and DIPEA (1.27 mL, 7.32 mmol, 3.0 equiv). The tube was heated to 85° C. overnight. The reaction was allowed to cool tort and then concentrated. The resulting residue was then redissolved in dichloromethane (50 mL) and washed with saturated aqueous sodium bicarbonate (2×20 mL). The collected organic was dried over sodium sulfate, filtered and concentrated to afford a light orange solid. This material (1.1 g, 1.9 mmol, 1 equiv) was then taken up in dioxane (5 mL) and 4 M HCl in dioxane (4.83 mL, 19.3 mmol, 10 equiv) was added. The resulting solution was allowed to stir at room temperature for 15 minutes. The dioxane removed in vacuo and the residue was redissolved in dichloromethane (20 mL) and washed with saturated sodium bicarbonate (10 mL). The collected organic was dried over sodium sulfate, filtered and concentrated to afford the desired product, A142(II). The crude product was subjected to the next step without further purification (see next step for overall reaction yield). MS (ESI+) m/z 465.4 $^1$H NMR (300 MHz, DMSO-d$_6$) δ ppm 0.97 (dd, J=11.68, 6.03 Hz, 6 H) 1.40 (t, J=7.06 Hz, 3 H) 1.61 (s, 3 H) 1.69 (s, 3 H) 2.25 (d, J=10.93 Hz, 1 H) 2.85 (m, 3 H) 3.01-3.14 (m, 1 H) 3.56 (s, 2 H) 4.49 (q, J=7.03 Hz, 2 H) 4.82 (d, J=4.33 Hz, 2 H) 7.71-7.79 (m, 1 H) 8.05-8.16 (m, 1 H) 8.18-8.26 (m, 1 H) 8.77 (d, J=3.96 Hz, 1 H) 12.15 (s, 1 H)

Compound A142

N-(5-((2R,5S)-1-(3-fluoropropyl)-2,5-dimethylpiperazine-4-carbonyl)-6,6-dimethyl-1,4,5,6-tetrahydropyrrolo[3,4-c]pyrazol-3-yl)picolinamide To a microwave vial was added A142(II) (0.200 g, 0.426 mmol, 1.0 equiv), triethylamine (0.148 mL, 1.06 mmol, 2.5 equiv), 1-bromo-3-fluoropropane (0.090 g, 0.639 mmol, 1.5 equiv) and tetrahydrofuran (1.5 mL). The resulting reaction mixture was heated in the MW at 150° C. for 1 hour. The crude reaction was concentrated in vacuo and taken up in methanol and trimethylamine (6 mL-6 mL) and stirred at rt for 16 hours. The reaction mixture was then concentrated again and the resulting residue dissolved in dichloromethane (50 mL) and washed with saturated aqueous sodium bicarbonate. The collected organic was dried over sodium sulfate, filtered and concentrated to give the crude product. The crude product was purified by flash chromatography. Eluted with methanol in dichloromethane (0→1% methanol) to afford the desired product A142 in 23% yield as an off white solid over two steps.

Examples A143-A144

Examples A143 and A144 were prepared using methods analogous to Example A142 above.

Example A145

N-(5-((2R,5S)-2,5-dimethyl-1-(2(tetradhydro-2H-pyran-4-yl)ethyl)piperazine-4-carbonyl)-6,6-dimethyl-1,4,5,6-tetrahydropyrrolo[3,4-c]pyrazol-3-yl)picolinamide

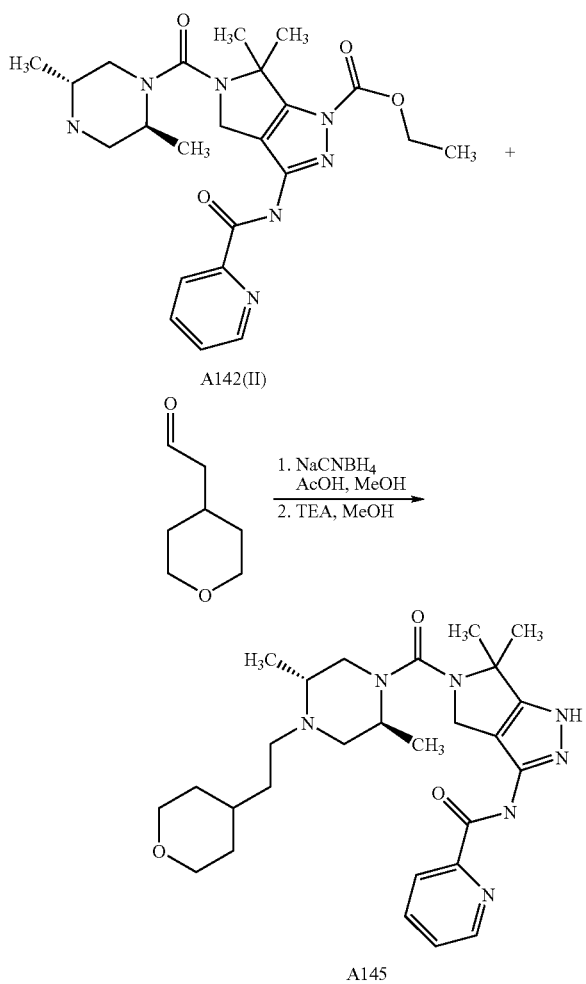

To a 100 mL round bottom flask was added A142(II) (0.100 g, 0.213 mmol, 1.0 equiv), methanol (3.0 mL), tetrahydropyranyl-4-acetaldehyde (0.041 g, 0.319 mmol, 1.5 equiv) and acetic acid (0.013 mL, 0.213 mmol, 1.0 equiv). After 1 hour, sodium cyanoborohydride (0.022 g, 0.341 mmol, 1.6 equiv) was added and the reaction was allowed to stir at rt for 16 hours. Triethylamine (3 mL) was added to the reaction and it was allowed to stir at rt for another 16 hours. Concentrated the reaction, diluted with dichloromethane (5 mL) and washed with saturated sodium sulfate (2 mL) and brine (2 mL). Dried collected organic over sodium sulfate, filtered and concentrated. The crude product was purified on preparative HPLC (0.1% HOAc) to afford 60 mg of the desired product A145 in 53% yield as a white solid.

Examples A146-A164

Examples A146 through A164 were prepared using methods analog to Examples A1, A142 and A145 above.

Example B1

Pyridine-2-carboxylic acid [5-(1-cyclobutyl-4-fluoro-piperidine-4-carbonyl)-6,6-dimethyl-1,4,5,6-tetrahydro-pyrrolo[3,4-c]pyrazol-3-yl]-amide

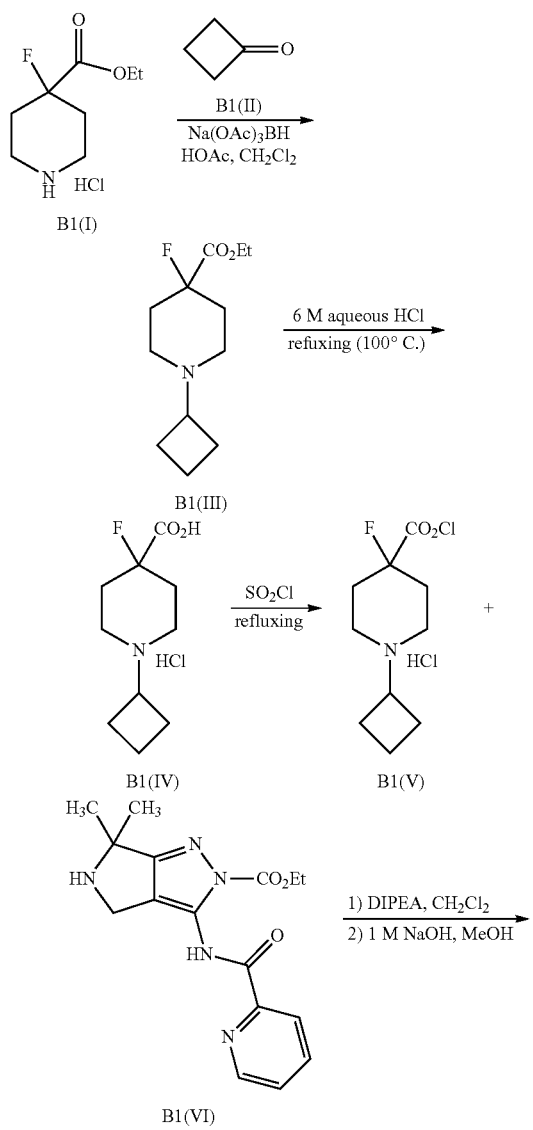

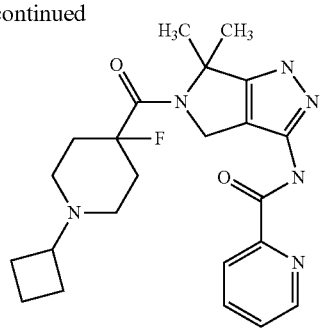

B1

Intermediate B1(II)

1-Cyclobutyl-4-fluoro-piperidine-4-carboxylic acid ethyl ester

To a 250 mL round bottle was added compound B1(1) ethyl 4-fluoropiperidine-4-carboxylate, hydrochloride (1.25 g, 5.91 mmol, 1.0 eq), CH$_2$Cl$_2$ (40 mL), cyclobutanone B1(II) (1.30 g, 7.68 mmol, 1.30 eq), and glacial HOAc (0.338 mL, 5.91 mmol, 1.0 eq). After stirring at rt for 5 to 10 min, sodium triacetoxyborohydride (2.00 g, 9.45 mmol, 1.60 eq) was added in one portion. A cloudy solution was obtained. The reaction mixture was stirred at rt for 2 h. To the reaction mixture, 100 mL aqueous NaOH (1 M) was added, and the resulting suspension was stirred at rt for 10 min. The reaction was extracted with EtOAc (150 mL). The organic layer was collected, washed with brine (200 mL), dried over Na$_2$SO$_4$, filtered, and concentrated to afford the desired product, B1(III), as a colorless oil. The crude product was cleaned and subjected to the next step without purification (see next step for the overall reaction yield). $^1$H NNR (400 MHz, CDCl$_3$, ppm) δ 1.28 (t, J=7.20 Hz, 3H), 1.64-1.73 (m, 2H), 1.82-1.99 (m, 4H), 2.01-2.21 (m, 6H), 2.72-2.80 (m, 3H), 4.22 (q, J=7.2 Hz, 2H); $^{19}$F NMR (376 Hz, CDCl$_3$, ppm) δ -166.83.

Intermediate B1(IV)

1-Cyclobutyl-4-fluoro-piperidine-4-carboxylic acid hydrochlorite

The intermediate B1(III) (crude, 5.91 mmol) was dissolved in 10 mL 6 M aqueous HCl. The colorless solution was warmed to 100° C. and refluxed under N$_2$. After 2 h, the reaction mixture was cooled to rt. The solvent was removed and a yellow solid was obtained. The solid was washed with 10 mL EtOAc, and dried under vacuum to afford 1.20 g of the desired product B1(IV) as a white solid in 85% yield over two steps. The product was subjected to next step without further purification. $^1$H NNR (400 MHz, DMSO-d$_6$, ppm) δ 1.63-1.78 (m, 2H), 2.10-2.16 (m, 4H), 2.35-2.45 (m, 4H), 2.82-2.88 (m, 2H), 3.29-3.32 (m, 2H), 3.66-3.70 (m, 1H), 11.63 (br s, 1H), 13.68 (br s, 1H); $^{19}$F NMR (376 Hz, DMSO-d$_6$, ppm) δ -166.31.

Compound B1

Pyridine-2-carboxylic acid [5-(1-cyclobutyl-4-fluoro-piperidine-4-carbonyl)-6,6-dimethyl-1,4,5,6-tetrahydro-pyrrolo[3,4-c]pyrazol-3-yl]-amide The crude starting material B1(IV) (0.673 mmol) was dissolved in 10 mL SOCl$_2$. The obtained pale yellow suspension was warmed to 80° C. and refluxed under $N_2$ for 1 h. At this point, the reaction turned into clear pale yellow solution. The reaction mixture was cooled to rt. The solvent was removed under reduced pressure to afford the acyl chloride B1(V) as a yellow solid in quantitative yield.

To a 100 mL RB were added the acyl chloride B1(V) (crude, 0.673 mmol, 1.3 eq), compound ethyl 6,6-dimethyl-3-[(pyridin-2-ylcarbonyl)amino]-5,6-dihydropyrrolo[3,4-c]pyrazole-2 (4H)-carboxylate, B1(VI), (189 mg, 0.518 mmol, 1.0 eq), and 13 mL $CH_2Cl_2$. The resulting suspension was stirred at it for 5 min under $N_2$. DIPEA (0.354 ml, 2.07 mmol, 4.0 eq) was added slowly and one can see that lots of smoke was generated. After being stirred at it for 1 h, the reaction was quenched with brine (50 mL), extracted with EtOAC (50 mL), dried over $Na_2SO_4$, and concentrated. The crude coupling product was subjected to next deprotection step.

To a solution of crude coupling product in 10 mL MeOH was added 1.5 mL 1.0 M aqueous NaOH dropwise at rt. A yellow clear solution was obtained. The LC-MS indicated that the reaction was complete in 30 min. The reaction was diluted with 50 mL EtOAc, and washed with brine (50 mL). The organic layer was collected, dried over $Na_2SO_4$, filtered, and concentrated to give the crude product. The crude product was purified on preparative HPLC (0.1% HOAc) to afford 80 mg of the desire product, B1, in 28% yield as a white solid over two steps.

Example B2

Pyridine-2-carboxylic acid {5-[4-fluoro-1-(tetrahydro-pyran-4-yl)-piperidine-4-carbonyl]-6,6-dimethyl-1,4,5,6-tetrahydro-pyrrolo[3,4-c]pyrazol-3-yl}-amide

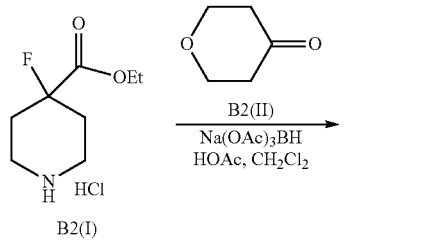

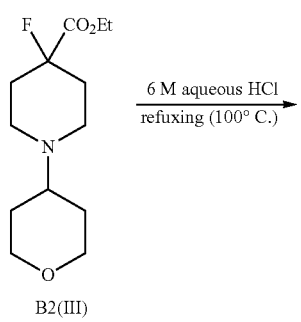

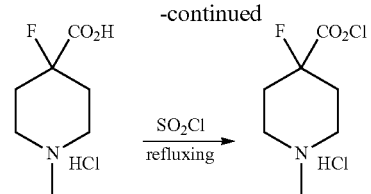

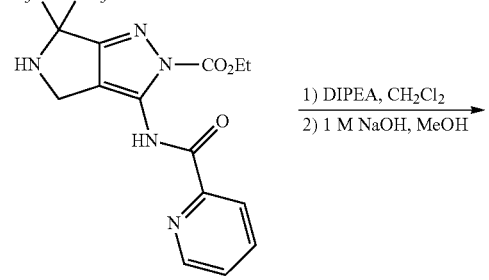

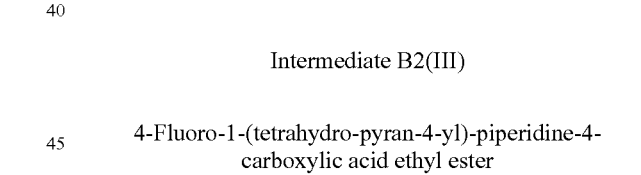

Intermediate B2(III)

4-Fluoro-1-(tetrahydro-pyran-4-yl)-piperidine-4-carboxylic acid ethyl ester

To a 250 mL RB were added compound B2(I) ethyl 4-fluoropiperidine-4-carboxylate, hydrochloride (1.25 g, 5.91 mmol, 1.0 eq), $CH_2Cl_2$ (20 mL), 4-oxotetrahydropyranone B2(II) (0.61 mL, 6.50 mmol, 1.10 eq), and glacial HOAc (0.340 mL, 5.91 mmol, 1.0 eq). After being stirred at rt for 5 to 10 min, sodium triacetoxyborohydride (2.02 g, 9.45 mmol, 1.60 eq) was added in one portion. A cloudy solution was obtained. After being stirred at rt for 12 h, the reaction mixture was diluted with 150 mL $Et_2O$ and 200 mL NaOH (1 M aqueous). The resulting suspension was stirred at rt for 1 h. The organic layer was collected, washed with 200 mL brine, dried over $Na_2SO_4$, filtered, and concentrated to afford 320 mg of the desired product, 4-fluoro-1-(tetrahydro-pyran-4-yl)-piperidine-4-carboxylic acid ethyl ester B2(III) in 21% yield as a colorless oil. $^1$H NNR (400 MHz, $CDCl_3$, ppm) δ 1.30 (t, J=7.08, 3H), 1.56-1.66 (m, 2H), 1.74-1.78 (m, 2H), 1.94-2.21 (m, 4H), 2.46-2.55 (m, 3H), 2.82-2.85 (m, 2H), 3.38 (ddd, J=1.52, 11.84, 11.84, 2H), 4.03 (dd, J=4.28, 11.08, 2H), 4.24 (q, J=7.05 Hz, 2H); $^{19}$F NMR (376 Hz, $CDCl_3$, ppm) δ -166.94.

Intermediate B2(IV)

4-Fluoro-1-(tetrahydro-pyran-4-yl)-piperidine-4-carboxylic acid hydrochlorite To a vial were added B2(III) (260 mg, 1.0 mmol) and 8 mL aqueous HCl (6.0 M). A colorless solution was obtained. The solution was stirred at rt for 5 min and was warmed to 100° C. The mixture was refluxing at 100° C. for 2 h and a pale orange solution was obtained. The reaction was then cooled to rt, and the solvent was removed under reduced pressure to afford a yellow solid. The solid was washed with 2×3 mL EtOAc to afford the 260 mg of the desired product, 4-fluoro-1-(tetrahydro-pyran-4-yl)-piperidine-4-carboxylic acid hydrochlorite B2(IV), as a yellow solid in 97% yield. $^1$H NNR (400 MHz, DMSO-$d_6$, ppm) δ 1.70-1.80 (m, 2H), 2.02-2.05 (m, 2H), 2.14-2.20 (m, 2H), 2.41-2.59 (m, 2H), 2.97-3.09 (m, 2H), 3.29 (dd, J=11.33, 11.33 Hz, 2H), 3.39-3.53 (m, 3H), 3.96 (dd, J=3.78, 11.08 Hz, 2H), 11.19 (s, 1H), 13.76 (s, 1H); $^{19}$F NMR (376 Hz, DMSO-$d_6$, ppm) δ -166.57.

Compound B2

Pyridine-2-carboxylic acid {5-[4-fluoro-1-(tetrahydro-pyran-4-yl)-piperidine-4-carbonyl]-6,6-dimethyl-1,4,5,6-tetrahydro-pyrrolo[3,4-c]pyrazol-3-yl}-amide Intermediate B2(IV) (240 mg, 0.896 mmol) was dissolved in 10 mL SOCl$_2$. The suspension was warmed to 80° C. After stirring the mixture at 80° C. for 1 h, the suspension became a clear pale yellow solution indicating that the reaction was done. The mixture was cooled to rt and the solvent was removed under reduced pressure to afford 257 mg (100%) of the desired product, acyl chloride B2(V), as a white solid.

To a 100 mL RB were added acyl chloride B2(V) (257 mg, 0.896 mmol, 1.5 eq), compound B2(VI) ethyl 6,6-dimethyl-3-[(pyridin-2-ylcarbonyl)amino]-5,6-dihydropyrrolo[3,4-c]pyrazole-2(4H)-carboxylate (219 mg, 0.598 mmol, 1.0 eq), and 13 mL CH$_2$Cl$_2$. The resulting suspension was stirred at rt for 5 min under N$_2$. DIPEA (0.408 ml, 2.39 mmol, 4.0 eq) was added slowly to generate smoke. After stirring the reaction at rt for 1 h, the reaction was quenched with brine (20 mL), extracted with CH$_2$Cl$_2$ (50 mL), dried over Na$_2$SO$_4$, and concentrated. The crude product was dissolved in 10 mL MeOH. At rt, 1.5 mL of 1 M aqueous NaOH was added dropwise. LC-MS indicated that the reaction was complete in 5 to 10 min. The reaction was diluted with 100 mL EtOAc, and washed with 100 mL brine. The organic solvent was collected, dried over Na$_2$SO$_4$, filtered, and concentrated to give a crude final product. The crude product was purified by preparative HPLC to give us 200 mg of the desired product, B2 as a partial HOAc salt, in 47% yield over two steps.

Example B3

3,4-Dichloro-N-[5-(4-fluoro-1-methyl-piperidine-4-carbonyl)-6,6-dimethyl-1,4,5,6-tetrahydro-pyrrolo[3,4-c]pyrazol-3-yl]-benzamide

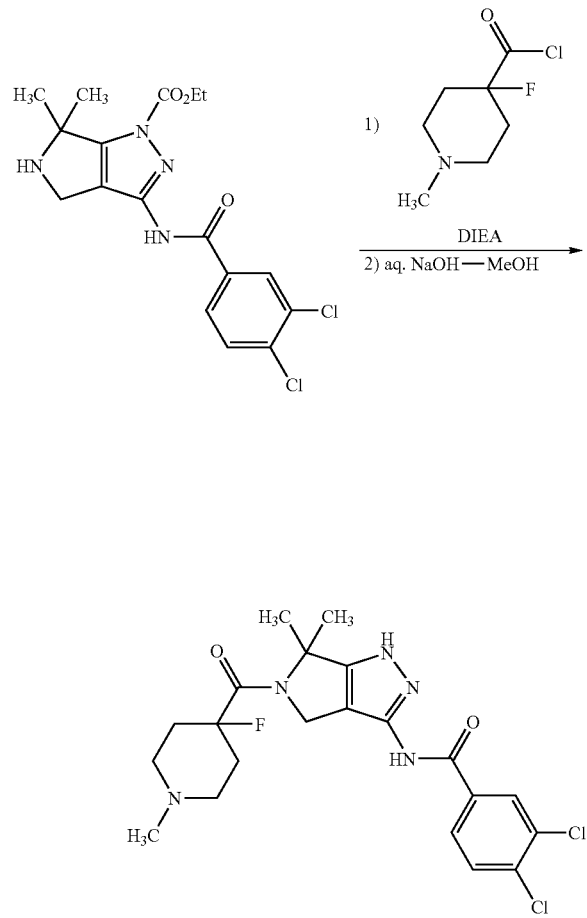

DIEA (0.220 mL, 1.66 mmol) and 3-(3,4-Dichloro-benzoylamino)-6,6-dimethyl-5,6-dihydro-4H-pyrrolo[3,4-c]pyrazole-1-carboxylic acid ethyl ester (221 mg, 0.51 mmol) were added to a solution of 4-Fluoro-1-methyl-piperidine-4-carbonyl chloride (0.51 mmol) in CH$_2$Cl$_2$ (10 mL). The reaction was stirred at RT for 4 h. The mixture was quenched with H$_2$O (30 mL), extracted with CHCl$_3$ (2×30 mL). The organic layers were dried over MgSO$_4$ and concentrated to give the title compound as brown color oil which was used without further purification. ESI (MNa$^+$): 564.10.

The above oil was taken into MeOH (5 mL) and NaOH (1N, 3 mL) was added. The mixture was stirred at RT for 2 h, concentrated and purified by reverse phase HPLC to give a white solid B3 (15 mg, 6%).

Example B4

Example B4 was prepared using methods analogous to Example B1 above.

Example C1
N-(5-{[2S,5R)-4-ethyl-2,5-dimethylpiperazin-1-yl]carbonyl}-6,6-dimethyl-1,4,5,6-tetrahydropyrrolo[3,4-c]pyrazol-3-yl)pyrazine-2-carboxamide
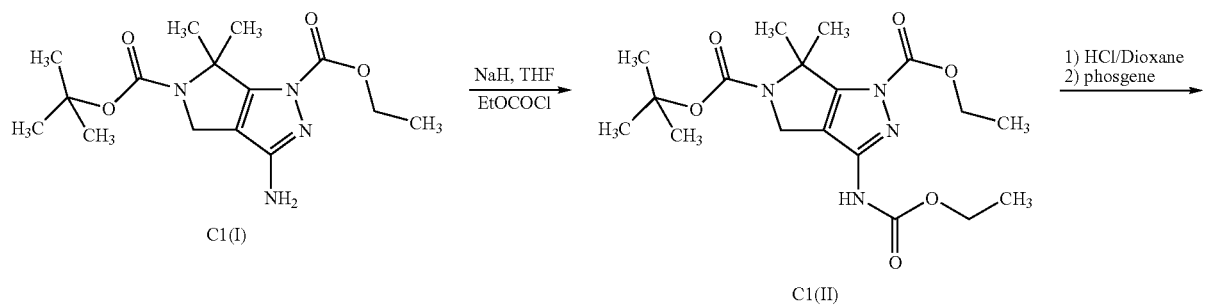
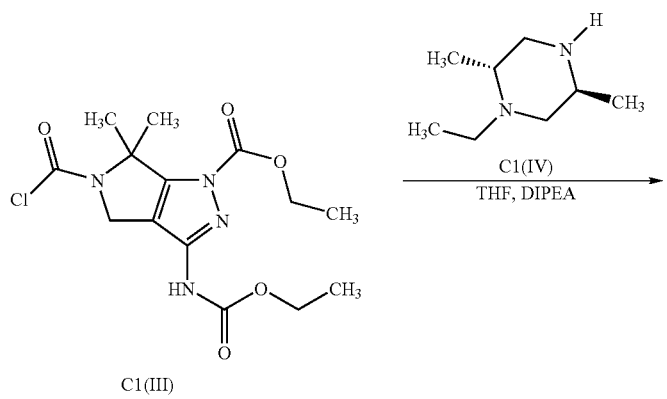
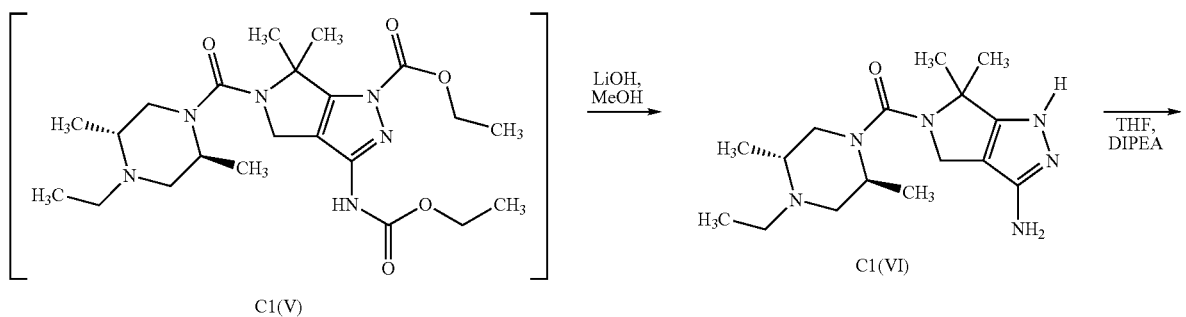
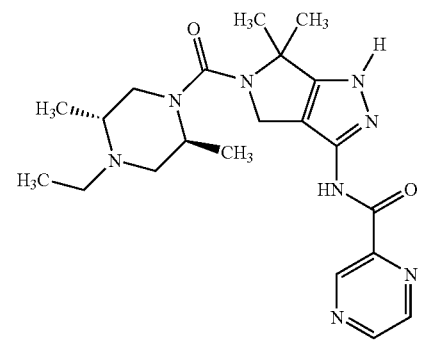

Intermediate C1(II)

5-tert-Butyl 1-ethyl 3-amino-6,6-dimethyl-4,6-dihydropyrrolo[3,4-c]pyrazole-1,5-dicarboxylate To a 0° C. solution of 5-tert-butyl 1-ethyl 3-amino-6,6-dimethyl-4,6-dihydropyrrolo[3,4-c]pyrazole-1,5-dicarboxylate, C1(I) (16.2 g, 49.9 mmol) in THF (100 mL) was added NaH (2.4 g, 59.9 mmol) in 3 portions. The reaction was stirred for 15 min in an ice bath, then ethyl chloroformate (6.5 g, 59.9 mmol) was added over 10 min. The reaction was warmed to room temperature and stirred for 16 h, then quenched with NH$_4$Cl (sat) and extracted with EtOAc (2×50 mL). The combined extracts were washed with brine then dried (MgSO$_4$) filtered and concentrated to give the desired compound C1(II) (19.8 g, 99%). Mass spectrum: Calcd for $C_{18}H_{29}N_4O_6$ (M+H): 397. Found 397.

Intermediate C1(III)

Ethyl 5-(chlorocarbonyl)-3-[(ethoxycarbonyl)amino]-6,6-dimethyl-5,6-dihydropyrrolo[3,4-c]pyrazole-1(4H)-carboxylate To a solution of C1(II) (19.8 g, 49.9 mmol) in dioxane (20 mL) was added HCl (60 mL, 4M in dioxane). The reaction was stirred at room temperature for 3 h then concentrated and dried under vacuum. The HCl salt of ethyl 3-[(ethoxycarbonyl)amino]-6,6-dimethyl-5,6-dihydropyrrolo[3,4-c]pyrazole-1(4H)-carboxylate was taken up in CH$_2$Cl$_2$ (60 mL). DIPEA (16.1 g, 125 mmol) was added and the reaction mixture was cooled in an ice bath. Phosgene (30 mL, 20% in toluene) was added slowly then the reaction was warmed to room temperature and run overnight. The reaction was concentrated then taken up in EtOAc (100 mL) and water (100 mL). The aqueous phase was extracted with EtOAc (2×25 mL) then the combined organic extracts were washed with brine, dried (MgSO$_4$), filtered and concentrated. The crude material was purified by silica gel column chromatography using CH$_2$Cl$_2$—2% 7N NH$_3$/MeOH in CH$_2$Cl$_2$ to give the title compound C1(III) as a white solid (9.58 g, 54%). Mass spectrum: Calcd for $C_{14}H_{20}ClN_4O_5$ (M+H): 359. Found 359.

Intermediate C1(V)

Ethyl 3-[(ethoxycarbonyl)amino]-6,6-dimethyl-5-{[4-ethyl(2S,5R)-2,5-dimethylpiperazin-1-yl]carbonyl}-5,6-dihydropyrrolo[3,4-c]pyrazole-1 (4H)-carboxylate To a sealed tube was added N-ethyl (2S,5R)-2,5-dimethylpiperazine C1(IV), DIPEA and THF followed by C1(III). The tube was sealed and placed in an oil bath at 80° C. and heated for 16 h. The reaction was cooled to room temperature then concentrated. This resulting material C1(V) was carried on forward without further purification.

Intermediate C1(VI)

5-{[(2S,5R)-4-ethyl-2,5-dimethylpiperazin-1-yl]carbonyl}-6,6-dimethyl-1,4,5,6-tetrahydropyrrolo[3,4-c]pyrazol-3-amine To a microwave vial was added C1(V), MeOH and LiOH. The reaction was heated at 110° C. in the microwave for 20 min. The crude reaction mixture was concentrated and taken up in THF. The insoluble material was filtered off and the filtrate was concentrated to give the title compound C1(VI). This material was used further without purification.

Compound C1

N-(5-{[(2S,5R)-4-Ethyl-2,5-dimethylpiperazin-1-yl]carbonyl}-6,6-dimethyl-1,4,5,6-tetrahydropyrrolo[3,4-c]pyrazol-3-yl)pyrazine-2-carboxamide A 2 mL THF suspension of C1(VI) (240 mg, 0.7 mmol) was added to a solution of pyrazine-2-carbonyl chloride (213 mg, 2 eq) and diisopropylethyl amine (0.5 mL, 3 eq) in 3 mL THF. After stirring at room temperature for 3 hours, the solvent was removed in vacuo. Purification as in example A1 afforded the title compound C1 as a white solid (16 mg, 5%).

Examples C2-C8

Examples C2 to C8 were prepared using methods analogous to Example C1 above.

Example D1

Currently no embodiments were prepared using Route D as shown in Scheme 2 above, although it is expected that one skilled in the art can use route D as described above to prepare many compounds of the invention.

Example E1

N-(6,6-Dimethyl-5-{[(3S,8aS)-3-methylhexahydropyrrolo[1,2-a]pyrazin-2 (1H)-yl]carbonyl}-1,4,5,6-tetrahydropyrrolo[3,4-c]pyrazol-3-yl)-3-ethylisoxazole-5-carboxamide

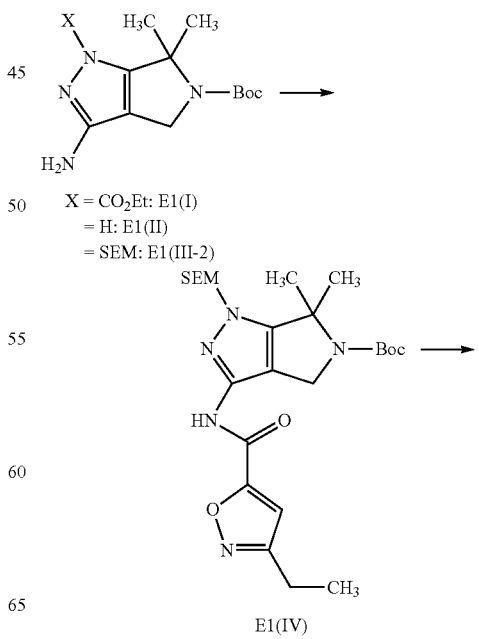

X = CO$_2$Et: E1(I)
 = H: E1(II)
 = SEM: E1(III-2)

E1(IV)

-continued

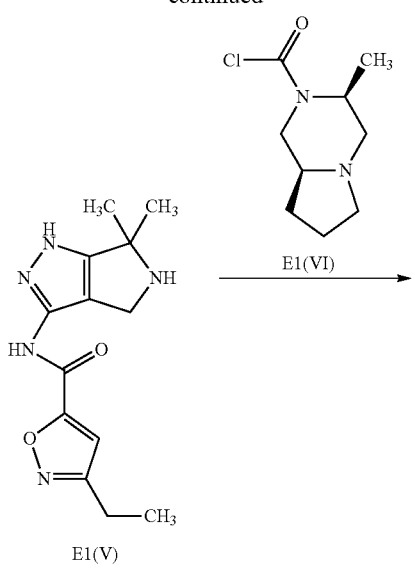

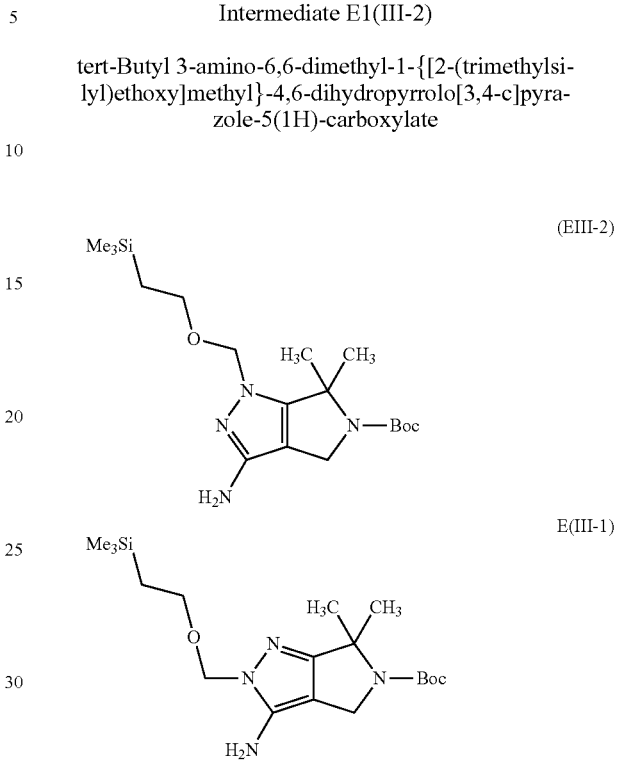

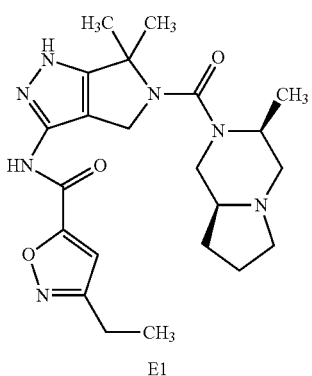

Intermediate E1(II)

tert-Butyl 3-amino-6,6-dimethyl-4,6-dihydropyrrolo[3,4-c]pyrazole-5(1H)-carboxylate Reagent 5-tert-butyl 1-ethyl 3-amino-6,6-dimethyl-4,6-dihydropyrrolo[3,4-c]pyrazole-1,5-dicarboxylate, E1(I), (10.97 g, 33.9 mmol) was dissolved in MeOH (200 mL) after which NaOH (5 eq, 169 mmol) was added. After stirring the mixture at room temperature for 3 h, the starting material disappeared. After removal of MeOH, add $H_2O$ and AcOEt was added, and the product was extracted with AcOEt and dried over $Na_2SO_2$ followed by concentration to afford E1(II).

Intermediate E1(III-2)

tert-Butyl 3-amino-6,6-dimethyl-1-{[2-(trimethylsilyl)ethoxy]methyl}-4,6-dihydropyrrolo[3,4-c]pyrazole-5(1H)-carboxylate To the mixture of the intermediate E1(II) (87 g), methylene chloride (1.74 L) and diisopropylethylamine (87 g) at 0° C. were added 2-(trimethylsilyl)ethoxymethyl chloride (63 g) drop wise at 0° C. (1 hour addition). The reaction mixtures were stirred at room temperature over night. The reaction was a light brown solution. Then the mixture was concentrated to give a light yellow/brown oil and the residue was mixed with ethyl acetate and the salts were filter off. The mixture was purified with silica gel (2:1 to 1:1 EtOAc/Hexane with 0.5% of TEA) to afford the regioisomers E1(III-2) (24 g, >90% purity by HPLC) and E(III-1) (10 g, >98% purity by HPLC). $^1$H NMR (400 MHz, CD3OD) ppm -0.03 (s, 9H) 0.88 (t, J=8.2 Hz, 2H) 1.48 and 1.53 (s, 4.5H each, a total of 9H), 1.70 (s, 3H), 1.72 (s, 3H), 3.56-3.62 (m, 2H), 4.24-4.26 (m, 2H), 5.16 (s, 2H).

Intermediate E1(VII)

N-(6,6-Dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-yl)-3-ethylisoxazole-5-carboxamide A 0.25 M solution of SEM-Boc protected aminopyrrolopyrazole, E1(III-2) was prepared using anhydrous DMF as solvent. A 0.25 M solution of 3-ethylisoxazole-5-carboxylic acid was prepared using anhydrous DMF as solvent. A fresh 0.5 M solution of o-(7-azabenzotriazole-1-yl)-N,N,N',N'-tetramethyl uronium hexafluorophosphate (HATU) was prepared in anhydrous DMF. To the reaction tube were added 320 μL (0.08 mmol, 1 equiv, 0.25M) of the 3-ethylisoxazole-5-carboxylic acid DMF solution prepared, 320 μL (0.080 mmol, 1 equiv, 0.25M) of SEM-Boc protected aminopyrrolopyrazole DMF solution prepared, and 40 μL (0.288 mmol, 3.6 equiv) neat TEA followed by the 160 μL (0.080 mmol, 1 equiv) of the HATU DMF solution. The reaction mixtures were stirred at 60° C. for 16 h. Then the tube was allowed to cool to room temperature. The solvents and volatiles from the tubes were removed in vacuo. To the residue were added 1 mL of EtOAc and 1 mL of 2M aqueous NaOH. After the tube was covered with Parafilm, the covered test tube was vigorously shaken until all residues have dissolved or the mixtures are completely homogenized. The agitation was stopped and the phases were allowed to separate completely. The supernatant organic layer (EtOAc layer) of each test tube was transferred into its corresponding receiving tube. EtOAc (0.5 mL) was added to the tube and extracted the organic layers after the agitation of the mixtures and these procedures were repeated twice. The solvent (EtOAc) and volatiles from the receiving tube were removed in vacuo until they were dry. To the residue was added 0.6 mL (2.4 mmol, 30 equiv) of 4M HCl in dioxane and the mixtures were stirred at room temperature for 2 h. Then the solvent, volatiles and HCl from the tube were removed in vacuo. To the residue were added 500 μL anhydrous DMA, 70 μL neat DIPEA (0.400 mmol, 5 equiv.). A 0.25 M solution of (3S,8aS)-3-methylhexahydropyrrolo[1,2-a]pyrazine-2(1H)-carbonyl chloride, E1(VI), in anhydrous $CH_2Cl_2$ was prepared.

Intermediate E1(VI)

(3S,8aS)-3-methylhexahydropyrrolo[1,2-a]pyrazine-2(1H)-carbonyl chloride

Triphosgene (1.1 equiv.) was dissolved in DCM at 0° C. under $N_2$ in round bottom flask, and DIPEA (2 equiv.) was added dropwise to the stirred solution at 0° C. under $N_2$. The solution of (3S,8aS)-3-methyloctahydropyrrolo[1,2-a]pyrazine in $CH_2Cl_2$ was added dropwise to the triphosgene reaction mixture at 0° C. under $N_2$. After stirring for one hour at 0° C. under $N_2$, the reaction mixtures were warmed to room temperature and stirred for 16 hours under $N_2$. The solvent was evaporated and dried in vacuum overnight at room temperature. The dried product E1(VI) was utilized for the urea formation reaction without purification.

To the tube were added 385 μL (0.096 mmol, 1.2 equiv.) of E1(VI), and the mixture was stirred at 40° C. for 20 h. After removal of the solvent and volatiles in vacuo, 1340 μL of DMSO (containing 0.01% BHT) was added to each tube to reach a final concentration of 0.0572 M and the mixtures were agitated to dissolve the product. In order to prepare the analytical sample, 54 of the solution was removed, and the aliquot was diluted to 1.0 mL with 95:5 MeOH/$H_2O$, and submit for LC-MS analysis.

Crude reaction mixtures from plate 821-107-3930 were dissolved in MeOH:DMSO:H2O (95:5:5) solution and analyzed utilizing analytical scale $CO_2$ SFC (UV/MS {APCI+}/ELSD detection). Analytical SFC method parameters would include; Column: Zymor/Pegasus (150×4.6 mm, 5 μm), linear Gradient: 5 to 50% Eluent A (MeOH) in 2.5 min. at 5.6 ml/min (140 bar outlet pressure).

The same crude reaction mixtures were purified utilizing preparative scale $CO_2$ SFC (UV detection {260 nm}). Prep SFC method parameters would include: Column: Zymor/Pegasus (150×21.2 mm, 5 μm), linear Gradient: 5 to 50% Eluent A (MeOH) in 5 min. at 56 ml/min (140 bar outlet pressure).

Products were dried, weighed and dissolved in DMSO at 30 mM. Products were then analyzed using RP-HPLC (UV {260 nm}/MS {APCI+}/ELSD detection). The HPLC method parameters would include; Column: Peeke Scientific/HI-Q ($C_{18}$, 50×4.6 mm, 3 μm), linear Gradient: 100% Eluent A ($H_2O$+0.05% TFA) to 100% Eluent B (Acetonitrile+0.05% TFA) in 1.75 min at 3 ml/min.

All products, at least 85% pure by two or more HPLC detection methods with an NMR spectrum confirming a structure consistent with the molecular weight, were made available for screening.

Examples E1 through E14

All of Examples E2 through E14 utilized the same analytical and purification conditions as described in Example E1 above.

Example F1

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide

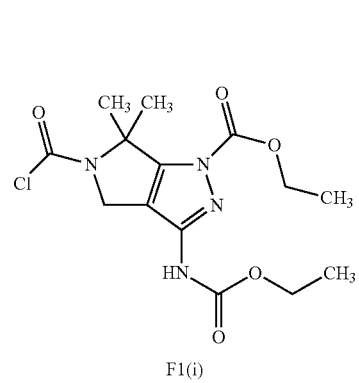
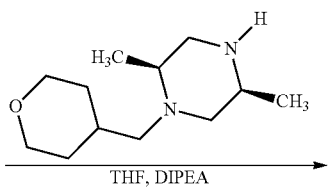

F1(i)

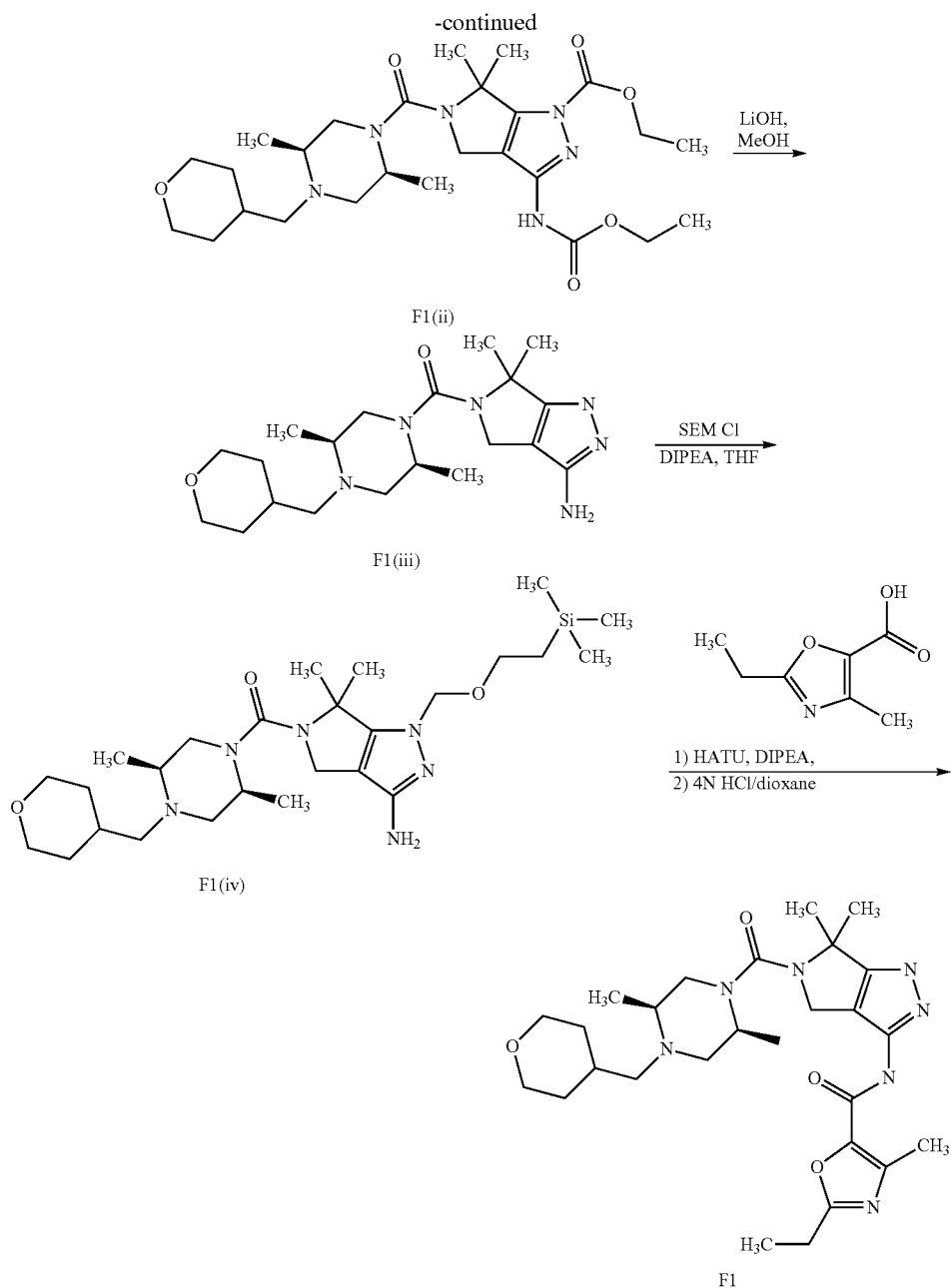

Intermediate F1(ii)

ethyl 5-{[(2S,5R)-2,5-dimethyl-4-(tetrahydro-2H-pyran-4-ylmethyl)piperazin-1-yl]carbonyl}-3-[(ethoxycarbonyl)amino]-6,6-dimethyl-5,6-dihydro-pyrrolo[3,4-c]pyrazole-1(4H)-carboxylate To a sealed tube was added (2R,5S)-2,5-dimethyl-1-(tetrahydro-2H-pyran-4-ylmethyl)piperizine (2.1 g, 9.89 mmol), DIPEA (3.8 mL, 21.8 mmol) and THF (50 mL) followed by F1(i) (3.6 g, 9.89 mmol). The tube was sealed and placed in an oil bath at 90° C. and heated for 16 h. The reaction was cooled to room temperature and concentrated then triturated with MeOH in two batches to give the title compound F1(ii) (4.89 g, 93%) as a white solid. Mass spectrum: Calcd for $C_{26}H_{42}N_6O_6$ (M+H): 535. Found 535.

Intermediate F1(iii)

5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine To a sealed tube was added F1(ii) (4.0 g, 7.54 mmol) in a slurry of MeOH (75 mL) and LiOH (1.0 g, 42 mmol). The reaction was heated at 100° C. for 16 h. The reaction was concentrated and taken up in THF (100 mL). The mixture was filtered through a bed of Celite and $MgSO_4$ then rinsed with THF (100 mL). The filtrate was concentrated to give 1.9 g (65%) of F1(iii) as a yellow solid. $^1$H NMR (300 MHz, DMSO-$d_6$) δ ppm 0.82-0.92 (m, 1 H), 0.92-1.00 (m, 6 H), 1.00-1.14 (m, 2 H), 1.48 (s, 3 H), 1.57 (s, 3 H), 1.69 (d, J=14.32 Hz, 2 H), 1.78-1.95 (m, 2 H), 2.27-2.48

(m, 3 H), 2.74-2.88 (m, 1H), 2.94-3.15 (m, 2 H), 3.18-3.31 (m, 2 H), 3.70-3.93 (m, 2 H), 4.26 (s, 2 H), 4.96 (br. s., 2 H). Mass spectrum: Calcd for $C_{20}H_{34}N_6O_2$ (M+H): 391. Found 391.

Intermediate F1(iv)

5-{[(2S,5R)-2,5-dimethyl-4-(tetrahydro-2H-pyran-4-ylmethyl)piperazin-1-yl]carbonyl}-6,6-dimethyl-1-{[2-(trimethylsilyl)ethoxy]methyl}-1,4,5,6-tetrahydropyrrolo[3,4-c]pyrazol-3-amine To a 0° C. solution of F1(iii) (1.7 g, 4.35 mmol) in THF (30 mL) was added DIPEA (0.95 mL, 5.44 mmol) followed by [2-(chloromethoxy)ethyl](trimethyl)silane (0.81 mL, 4.57 mmol). The reaction was slowly warm to RT and stirred for 16 h. The reaction was quenched with water (50 mL) and extracted with EtOAc (2×100 mL). The combined extracts were washed with brine (50 mL) then dried (MgSO4), filtered and concentrated to provide the title compound F1(iv) (1.7 g, 65%) as a yellow solid. Mass spectrum: Calcd for $C_{26}H_{48}N_6O_3Si$ (M+H): 521. Found 521.

Example F1

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide To a solution of 2-ethyl-4-methyl-1,3-oxazole-5-carboxylic acid (223 mg, 1.44 mmol) and F1(iv) (500 mg, 0.960 mmol) in DMF (5 mL) was added DIPEA (0.52 mL, 2.88 mmol) followed by HATU (548 mg, 1.44 mmol). The reaction was stirred at 65° C. for 16 h then diluted with NaHCO$_3$ (sat) (10 mL) and extracted with MTBE (2×20 mL). The combined extracts were washed with brine (15 mL) then dried (MgSO$_4$), filtered and concentrated. The crude solid was taken up in CH$_2$Cl$_2$ (5 mL) and 4N HCl in dioxane (5 mL) was added. The reaction was stirred at RT for 5 h. The reaction was concentrated then taken up in EtOAc (15 mL) and NaHCO$_3$ (sat) (15 mL) and extracted with EtOAc (2×10 mL). The combined extracts were washed with brine (15 mL) then dried (MgSO$_4$), filtered and concentrated. Preparative HPLC using 5-50% ACN/H$_2$O (0.1% AcOH) provided the title compound F1 as a white solid (35 mg, 6%).

Examples F2-F60

Examples F2 to F60 were prepared using methods analogous to Example F1 above.

Example G1

5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide

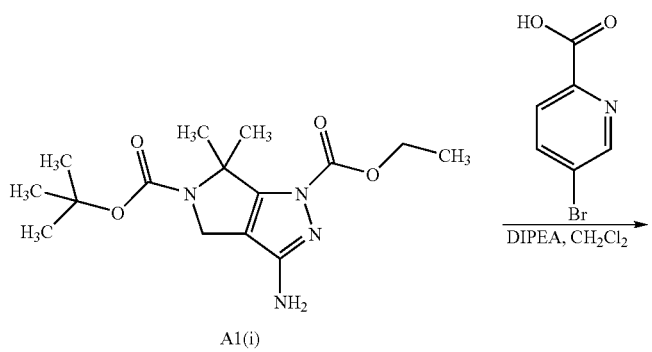

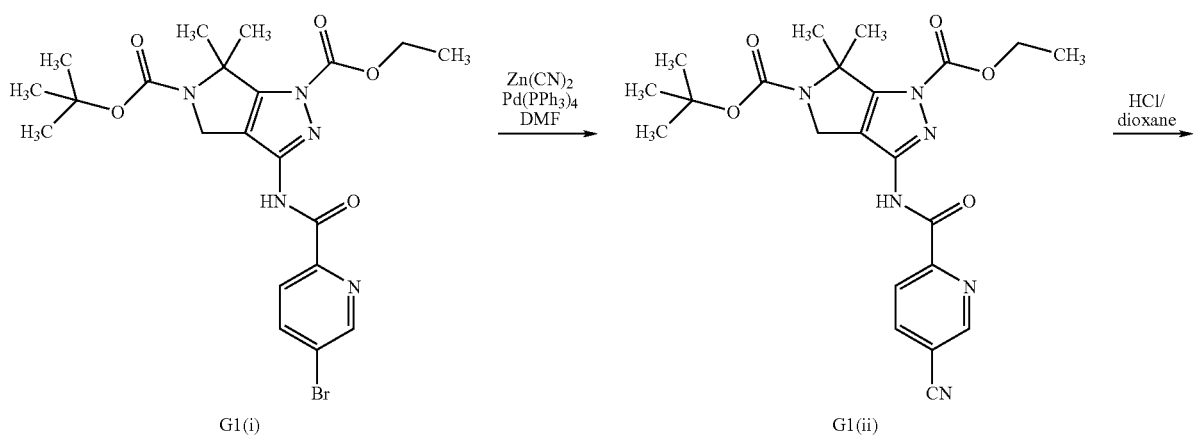

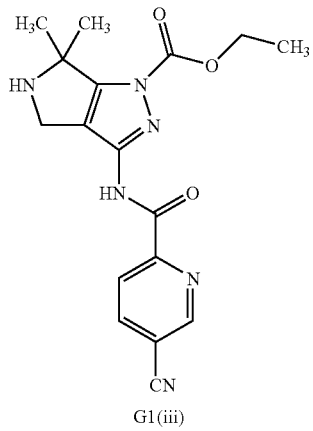 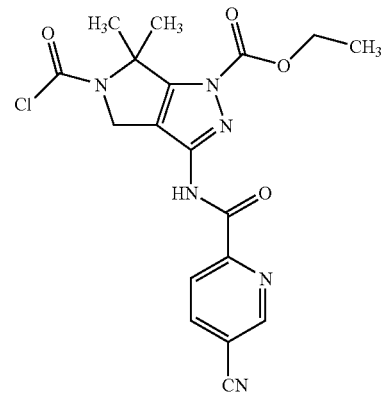 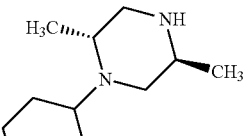

G1(iii)   G1(iv)

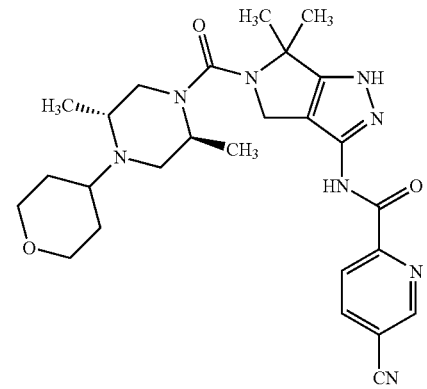

G1

Intermediate G1(i)

tert-butyl 1-ethyl 3-{[(5-bromopyridin-2-yl)carbonyl]amino}-6,6-dimethyl-4,6-dihydropyrrolo[3,4-c]pyrazole-1,5-dicarboxylate To a solution of 5-bromopyridine-2-carboxylic acid (3.11 g, 15.4 mmol) and 5-tert-butyl 1-ethyl 3-amino-6,6-dimethyl-4,6-dihydropyrrolo[3,4-c]pyrazole-1,5-dicarboxylate (5.00 g, 15.4 mmol) in DCM (200 mL) was added DIPEA (5.37 mL, 30.8 mmol) followed by HATU (7.03 g, 18.5 mmol). The reaction was allowed to run at 22° C. overnight. The reaction mixture was diluted with NaHCO3, the layers separated, and the organic portion dried (MgSO4), filtered and concentrated. The crude solid was triturated with Et2O to yield G1 (i) as a pale yellow solid (2.8 g, 15%). Mass Spectrum: Calcd for C21H27BrN5O5 (M+H): 509. Found: 509.

Intermediate G1(ii)

5-tert-butyl 1-ethyl 3-{[(5-cyanopyridin-2-yl)carbonyl]amino}-6,6-dimethyl-4,6-dihydropyrrolo[3,4-c]pyrazole-1,5-dicarboxylate To a suspension of G1(ii) (2.80 g, 5.51 mmol) in DMF (40 mL) was added Pd(PPh3)2 (0.636 g, 0.551 mmol) and Zn(CN)2 (0.647 g, 5.51 mmol). The solution evac/backfilled with argon ×3, then heat to 80° C. for 2 hours. The reaction mixture was diluted with water and EtOAc, the aqueous layer extracted with EtOAc ×2, the organic layer washed with water and brine, dried over MgSO4 and concentrated to give a bright yellow solid. The crude solid was triturated with Et2O to yield G1(ii) as a pale yellow solid (1.9 g, 76%). Mass Spectrum: Calcd for C22H27N6O5 (M+H): 455. Found: 455.

Intermediate G1(iii)

ethyl 3-{[(5-cyanopyridin-2-yl)carbonyl]amino}-6,6-dimethyl-5,6-dihydropyrrolo[3,4-c]pyrazole-1(4H)-carboxylate To a solution of G1(ii) (1.9 g, 4.18 mmol) in DCM (20 mL) was added 20 mL HCl/dioxane solution. Reaction mixture was allowed to stir overnight at 22° C. The suspension was concentrated to yield G1(iii) a pale yellow solid (1.9 g, 100%). Mass Spectrum: Calcd for C17H19N6O3 (M+H): 355. Found: 355.

Intermediate G1(iv)

ethyl 5-(chlorocarbonyl)-3-{[(5-cyanopyridin-2-yl)carbonyl]amino}-6,6-dimethyl-5,6-dihydropyrrolo[3,4-c]pyrazole-1 (4H)-carboxylate To a solution of G1(iii) (1.90 g, 4.45 mmol) in DCM (50 mL) was added DIPEA (2.30 mL, 17.8 mmol). The reaction mixture was cooled to −78° C. and triphosgene (0.924 g, 3.11 mmol) in a solution of DCM (30 mL) was added dropwise with an addition funnel. The reaction was stirred at −70° C. for 15 m then quenched with NaHCO3 (sat., aq.) and warmed to 22° C. The reaction mixture was diluted with water and the aqueous layer extracted with DCM ×2. The organic layer was washed with water and brine, dried over MgSO4 and concentrated to give G1(iv) as a bright yellow solid (1.9 g, 100%).

Example G1

5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide To a solution of G1(iv) (0.250 g, 0.600 mmol) and (2R,5S)-2,5-dimethyl-1-(tetrahydro-2H-pyran-4-yl)piperazine (0.238 g, 1.20 mmol) in THF (4 mL) was added DIPEA (0.5 mL, 3.00 mmol). The reaction was heated to 90 C. in a sealed tube overnight. Volatiles were, removed in vacuo and the residue was dissolved in MeOH (3 mL). TEA (3 mL) was added and the solution was stirred at 45° C. for 3 hours. Solution was concentrated and the crude mixture was purified by preparative chromatography to yield G1 as a white powder (0.130 g, 38%).

Examples G2-G3

Examples G2 to G3 were prepared using methods analogous to Example G1 above.

Example H1

N-[5-({(2S,5R)-4-[(4-hydroxytetrahydro-2H-pyran-4-yl)methyl]-2,5-dimethylpiperazin-1-yl}carbonyl)-6,6-dimethyl-1,4,5,6-tetrahydropyrrolo[3,4-c]pyrazol-3-yl]pyridine-2-carboxamide

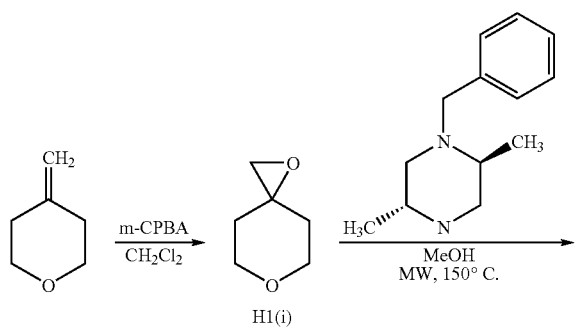

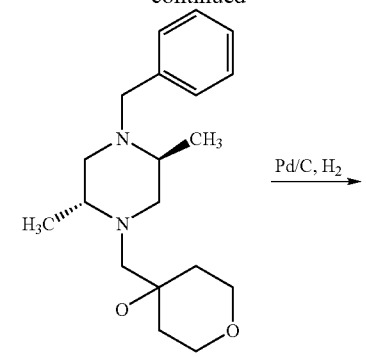

H1(ii)

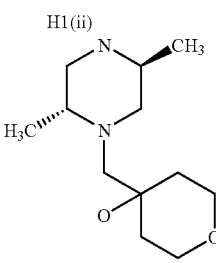

+

H1(iii)

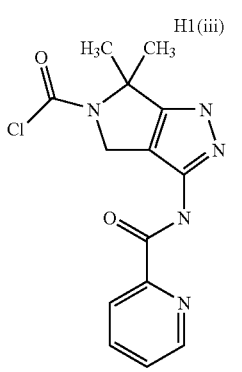

A1(V)

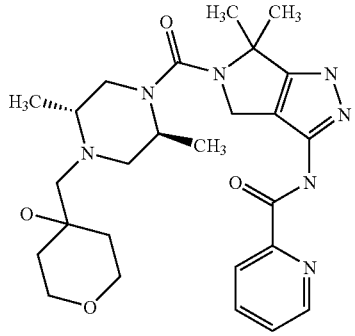

H1

Intermediate H1(i)

1,6-dioxaspiro[2.5]octane

A solution of 4-methylenetetrahydro-2H-pyran (1.00 g, 10.2 mmol) in CH$_2$Cl$_2$ (30 mL) was placed in an ice bath then meta-chloroperoxybenzoic acid (2.46 g, 14.3 mmol) was added in three portions. The reaction was slowly warmed to RT and stirred for 3 h then quenched with 10% NaOH(aq) (10 mL) and extracted with CH$_2$Cl$_2$ (2×15 mL). The combined extracts were dried (MgSO$_4$), filtered and concentrated to provide intermediate H1(i) as a clear oil (607 mg, 52%). $^1$H NMR (300 MHz, CHLOROFORM-d) δ ppm 1.45-1.63 (m, 2 H), 1.76-1.99 (m, 2 H), 2.69 (s, 2 H), 3.71-3.95 (m, 4 H).

Intermediate H1(ii)

4-{[(2R,5S)-4-benzyl-2,5-dimethylpiperazin-1-yl]methyl}tetrahydro-2H-pyran-4-ol

To a microwave vial was added 1,6-dioxaspiro[2.5]octane (259 mg, 2.3 mmol), (2S,5R)-1-benzyl-2,5-dimethylpiperazine (464 mg, 2.3 mmol) and 5 mL of MeOH. The vial was heated to 150° C. for 2 h in the microwave. The crude reaction was concentrated to provide intermediate H1(ii) (723 mg, 100%) $^1$H NMR (300 MHz, CHLOROFORM-d) δ ppm 0.92 (d, J=6.22 Hz, 3 H), 1.13 (d, J=5.84 Hz, 3 H), 1.35-1.45 (m, 1 H), 1.46-1.68 (m, 4 H), 1.83 (dd, J=11.30, 9.80 Hz, 1 H), 2.12 (d, J=13.94 Hz, 1 H), 2.36-2.53 (m, 3 H), 2.60-2.69 (m, 2 H), 2.85 (d, J=9.04 Hz, 1 H), 3.08 (d, J=13.38 Hz, 1 H), 3.71-3.82 (m, 4 H), 4.04 (d, J=13.38 Hz, 1 H), 7.10-7.47 (m, 5 H). Mass Spectrum: Calcd for $C_{19}H_{30}N_2O_2$ (M+H): 318. Found: 318.

Intermediate H1(iii)

4-{[(2R,5S)-2,5-dimethylpiperazin-1-yl]methyl}tetrahydro-2H-pyran-4-ol

To a nitrogen purged solution of H1(ii) (723 mg, 2.3 mmol) in MeOH (15 mL) was added Pd/C (72 mg, 0.07 mmol). The reaction was subject evacuation-backfill (3×) with $H_2$ gas then run overnight under an $H_2$ atmosphere. The completed reaction mixture was filtered through a bed of Celite, rinsed with $CH_2Cl_2$ and MeOH then concentrated to give the title compound (500 mg, 97%) as a yellow-orange semi solid. Mass Spectrum: Calcd for $C_{12}H_{24}N_2O_2$ (M+H): 229. Found: 229.

Compound H1

N-[5-({(2S,5R)-4-[(4-hydroxytetrahydro-2H-pyran-4-yl)methyl]-2,5-dimethylpiperazin-1-yl}carbonyl)-6,6-dimethyl-1,4,5,6-tetrahydropyrrolo[3,4-c]pyrazol-3-yl]pyridine-2-carboxamide.

The title compound was prepared using methods analogous to Example A1 above, where 4-{[(2R,5S)-2,5-dimethylpiperazin-1-yl]methyl}tetrahydro-2H-pyran-4-ol was substituted in place of (3S,8aS)-3-methyloctahydropyrrolo[1,2-a]pyrazine.

Table 1 provides a full listing of the compounds of the present invention and includes relevant H NMR data and Ki values as available Any of the above compounds of Formula I, can be converted into another analogous compound by standard chemical manipulations. All starting materials, regents, and solvents are commercially available and are known to those of skill in the art unless otherwise stated. These chemical manipulations are known to those skilled in the art and include (a) removal of a protecting group by methods outlined in T. W. Greene and P. G. M. Wuts, *Protective Groups in Organic Synthesis,* 2nd Ed., John Wiley and Sons, New York, 1991; (b) displacement of a leaving group (halide, mesylate, tosylate, etc) with a primary or secondary amine, thiol or alcohol to form a secondary or tertiary amine, thioether or ether, respectively; (c) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; (d) reductive amination of a primary or secondary amine using an aldehyde.

The compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of Formula I that are basic in nature are capable of forming a wide variety of different salts with various inorganic and organic acids. Although such salts must be pharmaceutically acceptable for administration to animals, it is often desirable in practice to initially isolate the compound of Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of Formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula I. Such non-toxic base salts include those derived from such pharmacologically acceptable cations as sodium, potassium, calcium, and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are inhibitors of protein kinase C and preferably selectively inhibit beta-1, beta-2 and optionally alpha isozymes of protein kinase C. With respect to the beta-2 isozyme in particular, the compounds of the present invention have Ki values of less than 200 nM.

As an inhibitor of protein kinase C the compounds are useful in the treatment of conditions in which protein kinase C has demonstrated a role in the pathology. Conditions recognized in the art include: diabetes mellitus and its complications, cancer, ischemia, inflammation, central nervous system disorders, cardiovascular disease, Alzheimer's disease and dermatological disase.

Protein kinase C has been linked to several different aspects of diabetes. Excessive activity of protein kinase C has been linked to insulin signaling defects and therefore to the insulin resistance seen in Type II diabetes. Karasik, A. et al. *J. Biol. Chem.* 265: 10226-10231 (1990); Chen, K. S. et al. *Trans. Assoc. Am. Physicians* 104: 206-212 (1991); Chin, J. E. et al *J. Biol. Chem.* 268: 6338-6347 (1993). In addition, studies have demonstrated a marked increase in protein kinase C activity in tissues known to be susceptible to diabetic complications when exposed to hyperglycemic conditions. Lee, T. S. et al., *J. Clin. Invest.* 83: 90-94 (1989); Lee, T. S. et al. *Proc. Natl. Acad. Sci USA* 86: 5141-5145 (1989); Craven, P. A. and DeRubertis, F. R. *J. Clin. Invest.* 83: 1667-1675 (1989); Wolf, B. A. *J. Clin. Invest.* 87: 1643-1648 (1991).

Protein kinase C activity has long been associated with cell growth, tumor promotion and cancer. Rotenberg, S. A. and Weinstein, I. B. *Biochem. Mol. Aspects Sel. Cancer* 1: 25-73 (1991). Ahamd et al., *Molecular Pharmacology:* 43, 858-862 (1993). It is known that inhibitors of protein kinase C inhibitors are effective in preventing tumor growth in animals. Meyer, T. et al. *Int. J. Cancer* 43: 851-856 (1989); Akinagaka, S. et al. *Cancer Res.* 51: 4888-4892 (1991). More recently, the protein kinase Cβ inhibitor, Enzastauring (LY317615.HCl) was shown to have a direct tumor effect by inducement of apoptosis and suppression of proliferating cultured tumor cell, in particular on human glioblastoma and colon carcinoma. Graff et al, *Cancer Res.* 16: 7462-7469 (2005). The compounds of the present invention also act as multridrug reversal (MDR) agents making them effective compounds when administered in conjunction with other chemotherapeutic agents.

Protein kinase C inhibitors have been shown to block inflammatory responses such as neutrophil oxidative burst, CD3 down-regulation in T-lymphocytes, and phorbol-induced paw edema. Towemy, B. et al. *Biochem. Biophvs. Res. Commun.* 171: 1087-1092 (199)); Mulqueen, M. J. et al. *Agents Actions* 37: 85-89 (1992). Accordingly, as inhibitors of PKC, the present compounds are useful in treating inflammation.

Protein kinase C activity plays a central role in the functioning of the central nervous system. Huang, K. P. *Trends Neurosci.* 12: 425-432 (1989). In addition, protein kinase C inhibitors have been shown to prevent the damage seen in focal and central ischemic brain injury and brain edema. Hara, H. et al. *J. Cereb. Blood Flow Metab.* 10: 646-653 (1990); Shibata, S. et al. *Brain Res.* 594: 290-294 (1992). Protein kinase C has also been determined to be implicated in Alzheimer's disease. Shimohama, S. et al. *Neurology* 43: 1407-1413 (1993). Accordingly, the compounds of the present invention are useful in treating Alzheimer's disease and ischemic brain injury.

Protein kinase C activity also plays an important role in cardiovascular disease. Increased protein kinase C activity in the vasculature has been shown to cause increased vasoconstriction and hypertension. A known protein kinase C inhibitor prevented this increase. Bilder, G. E. et al. *J. Pharmacol. Exp. Ter.* 252: 526-430 (1990). Because protein kinase C inhibitors demonstrate inhibition of the neutrophil oxidative burst, protein kinase C inhibitors are also useful in treating cardiovascular ischemia and improving cardiac function following ischemia. Muid, R. E. et al. *FEBS Lett.* 293: 169-172 (1990); Sonoki, H. et al. *Kokyu-To Junkan* 37: 669-674 (1989). The role of protein kinase C in platelet function has also been investigated and as shown elevated protein kinase C levels being correlated with increased response to agonists. Bastyr III, E. J. and Lu, J. *Diabetes* 42: (Suppl. 1) 97A (1993). PKC has been implicated in the biochemical pathway in the platelet-activity factor modulation of microvascular permeability. Kobayashi et al., *Amer. Pjus. Soc. H*1214-H1220 (1994). Potent protein kinase C inhibitors have been demonstrated to affect agonist-induced aggregation in platelets. Toullec, D. et al. *J. Biol. Chem.* 266: 15771-15781 (1991). Protein kinase C inhibitors also block agonist-induced smooth muscle cell proliferation. Matsumoto, H. and Sasaki, Y. *Biochem. Biophys, Res. Commun.* 158: 105-109 (1989). Therefore, the present compounds are useful in treating cardiovascular disease, atherosclerosis and restenosis.

Abnormal activity of protein kinase C has also been linked to dermatological disorders such as psoriasis. Horn, F. et al. *J. Invest. Dermatol.* 88: 220-222 (1987); Raynaud, F. and Evain-Brion, D. *Br. J. Dermatol.* 124: 542-546 (1991). Psoriasis is characterized by abnormal proliferation of keratinocytes. Known protein kinase C inhibitors have been shown to inhibit keratinocyte proliferation in a manner that parallels their potency as PKC inhibitors. Hegemann, L. et al. *Aarch. Dermatol. Res.* 283: 456-460 (1991); Bollag, W. B. et al. *J. Invest. Dermatol.* 100: 240-246 (1993). Accordingly, PKC inhibitors are useful in treating psoriasis.

The compounds of the invention are also isozyme-selective. The compounds preferentially inhibit protein kinase C beta-1 and beta-2 isozyme and optionally the alpha isozyme, over the remaining protein kinase C isozymes, i.e., gamma, delta, epsilon, zeta nad eta. Accordingly, compounds of the present invention inhibit beta-1 and beta-2 isozymes of protein kinase C, and optionally the alpha isozyme at much lower concentrations with minimal inhibition of the other PKC isozymes.

The compounds of the present invention are particularly useful in treating those disease states in which protein kinase C isozyme beta-1, beta-2, and optionally alpha, are associated. For example, the elevated blood glucose levels found in diabetes leads to an isozyme-specific elevation of the beta-2 isozyme in vascular tissues. *Proc. Natl. Acad. Sci. USA* 89: 11059-11065 (1992). A diabetes-linked elevation of the beta isozyme in human plateles has been correlated with their altered response to agonists. Bastyr III, E. J. and Lu, *J. Diabetes* 42: (Suppl 1) 97A (1993). The human vitamin D receptor has been shown to be selectively phosphorylated by protein kinase C beta. This phosphorylation has been linked to alterations in the functioning of the receptor. Hsieh et al, *Proc. Natl. Acad. Sci. USA* 88: 931509319 (1991); Hsieh et al. *J. Biol. Chem.* 268: 15118-15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847-15853 (1993).

In addition to the beta-1 and beta-2 isozymes discussed above, the protein kinase C alpha isozyme has been shown to have potential in the treatment of nephropathy: a PKC-alpha knockout mouse having STZ-induced diabetes showed improved nephropathy. Menne et al, *Diabetes* 53: 2101-2109 (2005). PKC alpha was implicated in heart contractility, Braz et al. *Nature Medicine* 10: 248-254 (2004); and also in the regulation of Akt activation and eNOS phosphorylation in endothelial cells. Partovian & Simons, *Cellular Signalling* 16: 951-957 (2004).

Assay

Protein Kinase C beta 2 (PKCβII) catalyzes the production of ADP from ATP that accompanies the phosphoryl transfer to the PKC Pseudosubstrate peptide (A->S, RFARKGSL-RQKNV). This transfer is coupled to the oxidation of p-NADH through the activities of Pyruvate Kinase (PK) and Lactate Dehydrogenase (LDH). (3-NADH conversion to NAD+ is monitored by the decrease in absorbance at 340 nm (e=6.22 $cm^{-1}$ $mM^{-1}$) using a Molecular Devices SPECTRA max PLUS spectrophotometer.

A typical assay was carried out on a 96-well, clear microtiter plate in a Molecular Devices spectrophotometer for 20 minutes at 30° C. in 0.1 mL of assay buffer containing 50 mM HEPES, pH 7.4, 5 nM PKC, 23 units of pyruvate kinase, 33 units of lactate dehydrogenase, 0.15 mM peptide, 0.1 mM ATP, 1 mM DTT, 4 mM PEP, 8 mM $MgCl_2$, 0.3 mM NADH, 60 mM $CaCl_2$, 10 mg/mL PS, 50 ng/mL PMA, 7.5% DMSO and from about 10,000 nM to 0.169 nM compound inhibitor. Stock solutions of 3-sn-phosphatidyl-L-serine (PS) and phorbol-12-myristate-13-acetate (PMA) were sonicated for 30 seconds just prior to addition to assay buffer and assays were initiated by the addition of 100 μM ATP.

Steady-state kinetic parameters for the bi-bi kinase reaction were determined at saturating phospho-acceptor peptide substrate concentration (0.15 mM) by fitting initial velocity data to the Michaelis-Menten equation, $$v=V_{max}[S]/(K_M+[S])$$

where v is the measured initial velocity, $V_{max}$ is the maximal enzyme velocity, [S] is the ATP substrate concentration, and $K_M$ is the Micheailis constant for ATP. Enzyme turnover values ($k_{cat}$) were calculated according to $k_{cat}=V_{max}[E]$, where [E] is the total enzyme concentration. Enzyme inhibition constants (apparent $K_i$ values) were determined by fitting initial velocities at variable inhibitor concentrations to a model for ATP competitive inhibition based on the Morrison equation). Morrison, J. F., *Biochim. Biophys Acta* 185: 269-286 (1969).

Pharmaceutical Compositions/Formulations, Dosaging and Modes of Administration

Methods of preparing various pharmaceutical compositions with a specific amount of active compound are known, or will be apparent, to those skilled in this art. In addition, those of ordinary skill in the art are familiar with formulation and administration techniques. Such topics would be discussed, e.g. in Goodman and Gilman's *The Pharmaceutical Basis of Therapeutics*, current ed., Pergamon Press; and *Remington's Pharmaceutical Sciences*, current ed., Mack Publishing, Co., Easton, Pa. These techniques can be employed in appropriate aspects and embodiments of the methods and compositions described herein. The following examples are provided for illustrative purposes only and are not meant to serve as limitations of the present invention.

The compounds of Formula I may be provided in suitable topical, oral and parenteral pharmaceutical formulations for use in the treatment of PKCβII mediated diseases. The compounds of the present invention may be administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous susperision. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the acceptable vehicles and solvents that may be employed are water, Ringers solution and isotonic sodium chloride solution.

For this purpose any bland fixed oil may be employed including synthetic mono- or diglycerides. In addition fatty acids such as oleic acid find use in the preparation of injectables.

The compounds of Formula I may also be administered in the form of suppositories for rectal administration of the drug. These compositions can be prepared by mixing the drug with a suitable non-irritating excipient that is solid at about 25 Celsius but liquid at rectal temperature and will therefore melt in the rectum to release the drug. Such materials include cocoa butter and other glycerides.

For topical use preparations, for example, creams, ointments, jellies solutions, or suspensions, containing the compounds of the present invention are employed. The compounds of Formula I may also be administered in the form of liposome delivery systems such as small unilamellar vesicles, large unilamellar vesicles and multimellar vesicles. Liposomes can be formed from a variety of phospholipides, such as cholesterol, stearylamine or phosphatidylcholines.

Dosage levels of the compounds of the present invention are of the order of about 0.5 mg/kg body weight to about 100 mg/kg body weight. A preferred dosage rate is between about 30 mg/kg body weight to about 100 mg/kg body weight. It will be understood, however, that the specific dose level for any particular patient will depend upon a number of factors including the activity of the particular compound being administered, the age, body weight, general health, sex, diet, time of administration, route of administration, rate of excretion, drug combination and the severity of the particular disease undergoing therapy. To enhance the therapeutic activity of the present compounds they may be administered concomitantly with other orally active antidiabetic compounds such as the sulfonylureas, for example, tolbutamide and the like.

For administration to the eye, a compound of the present invention is delivered in a pharmaceutically acceptable ophthalmic vehicle such that the compound is maintained in contact with the ocular surface for a sufficient time period to allow the compound to penetrate the cornea and/or sclera and internal regions of the eye, including, for example, the anterior chamber, posterior chamber, vitreous body, aqueous humor, vitreous humor, cornea, iris/ciliary's, lens, choroid/retina and sclera. The pharmaceutically acceptable ophthalmic vehicle may be an ointment, vegetable oil, or an encapsulating material. A compound of the invention may also be injected directly into the vitreous humor or aqueous humor.

The compounds of the invention, and pharmaceutically acceptable salts thereof, may be administered for the treatment of ophthalmic diseases such as age-related macular degeneration (both wet and dry 'AMD'), glaucoma, diabetic retinopathies (including diabetic macular edema), choroidal neovascular membrane (CNV), uveitis, myopic degeneration, ocular tumors, entral retinal vein occlusion, rubeosis, ocular neovascularization, central serous retinopathy, ocular surface discus such as dry eye, central retinal artery occlusion, cystoid macular edema and other retinal degenerative disease.

The compounds may be formulated as a depot preparation. Such long-acting formulations may be administered by implantation (for example, subcutaneously or intramuscularly) intramuscular injection or by the above mentioned sub-tenon or intravitreal injection. Alternatively, the active ingredient may be in powder form for constitution with a suitable vehicle, e.g., sterile pyrogen-free water, before use.

Within particularly preferred embodiments of the invention, the compounds may be prepared for topical administration in saline (combined with any of the preservatives and antimicrobial agents commonly used in ocular preparations), and administered in eyedrop form. The solution or suspension may be prepared in its pure form and administered several times daily. Alternatively, the present compositions, prepared as described above, may also be administered directly to the cornea.

Within preferred embodiments, the composition is prepared with a muco-adhesive polymer which binds to cornea. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of preferred compounds of the present invention is described in detail in the following examples, but the artisan will recognize that the chemical reactions described may be readily adapted to prepare a number of other compounds of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

TABLE 1

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A1 | Chiral; N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide | 29.2 | 1H NMR (400 MHz, DMSO-d6) d ppm 1.13-1.26 (m, 3 H) 1.26-1.36 (m, 1 H) 1.61 (d, J = 14.40 Hz, 6 H) 1.64-1.79 (m, 2 H) 1.82-2.04 (m, 4 H) 2.24 (dd, J = 10.48, 3.16 Hz, 1 H) 2.69-2.83 (m, 2 H) 2.94 (t, J = 7.58 Hz, 1 H) 3.22-3.45 (m, 2 H) 3.86 (d, J = 2.02 Hz, 1 H) 4.44-4.71 (m, 2 H) 7.63-7.82 (m, 1 H) 7.99-8.10 (m, 1 H) 8.17 (d, J = 7.83 Hz, 1 H) 8.74 (d, J = 4.55 Hz, 1 H). |
| A2 | Chiral; N-(5-{[(8S)-6,8-dimethyl-6,9-diazaspiro[4.5]dec-9-yl]carbonyl}-6,6-dimethyl-1,4,5,6-tetrahydropyrrolo[3,4-c]pyrazol-3-yl)pyridine-2-carboxamide | 3.05 | 1H NMR (400 MHz, DMSO-d6) ppm 1.03 (3 H, d, J = 6.06 Hz), 1.31 (1 H, d, J = 5.81 Hz), 1.57 (6 H, s), 1.66 (4 H, s), 1.89 (3 H, d, J = 1.77 Hz), 2.09 (3 H, d, J = 1.52 Hz), 2.16 (1 H, d, J = 18.19 Hz), 2.60-2.67 (1 H, m), 2.86 (1 H, d, J = 11.87 Hz), 3.31 (21 H, s), 4.59-4.70 (2 H, m), 7.68 (1 H, none), 8.10-8.15 (2 H, m), 8.72 (1 H, d, J = 4.30 Hz). |
| A3 | Chiral; N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-3-phenoxybenzamide | 36.8 | 1H NMR (400 MHz, CDCl3) δ ppm 1.31-2.25 (m, 13 H), 2.52-2.63 (m, 1 H), 2.75-3.18 (m, 5 H), 3.35-3.48 (m, 1 H), 3.92-4.58 (m, 3 H), 6.80-7.65 (m, 14 H), 9.53 (s, br, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A4 | Chiral<br><br>(S)-N-(5-(3-benzyl-1-methylpiperazine-4-carbonyl)-6,6-dimethyl-2,4,5,6-tetrahydropyrrolo[3,4-c]pyrazol-3-yl)benzo[b]thiophene-2-carboxamide | 146 | $^1$H NMR (400 MHz, MeOD) δ ppm: 1.65 (s, 3 H), 1.72 (s, 3 H), 2.29 (s, 3 H), 2.34-2.46 (m, 2 H), 2.55 (dd, J = 11.24, 4.67 Hz, 1 H), 2.62-2.73 (m, 1 H), 2.89 (dd, J = 13.26, 8.46 Hz, 1 H), 3.09 (dd, J = 13.39, 6.32 Hz, 1 H), 3.16-3.26 (m, 1 H), 3.36-3.45 (m, 1 H), 3.79 (s, 1 H), 4.39 (b, 1 H), 4.59 (b, 1 H), 7.11-7.19 (m, 1 H), 7.22-7.28 (m, 4 H), 7.40-7.53 (m, 2 H), 7.90-8.00 (m, 2 H), 8.15 (s, 1 H). |
| A5 | Chiral<br><br>(S)-N-(5-(3-benzyl-1-methylpiperazine-4-carbonyl)-6,6-dimethyl-1,4,5,6-tetrahydropyrrolo[3,4-c]pyrazol-3-yl)benzamide | 189 | $^1$H NMR (400 MHz, MeOD) d ppm: ppm: 1.56 (s, 3 H), 1.63 (s, 3 H), 2.21 (s, 3 H), 2.26-2.39 (m, 2 H), 2.46 (dd, J = 11.62, 4.80 Hz, 1 H), 2.54-2.64 (m, 1 H), 2.80 (dd, J = 13.26, 8.46 Hz, 1 H), 2.99 (dd, J = 13.39, 6.32 Hz, 1 H), 3.07-3.16 (m, 1 H), (3.27-3.36 (m, 1 H), 3.69 (b, 1 H), 4.30 (d, J = 12.63 Hz, 1 H), 4.51 (d, J = 13.14 Hz, 1 H), 7.02-7.11 (m, 1 H), 7.12-7.19 (m, 4 H), 7.43 (t, J = 7.45 Hz, 2 H), 7.48-7.56 (m, 1 H), 7.86 (d, J = 7.33 Hz, 2 H). |
| A6 | Chiral<br><br>(S)-N-(5-(3-benzyl-1-methylpiperazine-4-carbonyl)-6,6-dimethyl-1,4,5,6-tetrahydropyrrolo[3,4-c]pyrazol-3-yl)thiophene-2-carboxamide | 187 | $^1$H NMR (400 MHz, MeOD) d ppm: 1.55 (s, 3 H), 1.63 (s, 3 H), 2.22 (s, 3 H), 2.29-2.40 (m, J = 11.37, 3.03 Hz, 2 H), 2.48 (dd, J = 11.49, 4.93 Hz, 1 H), 2.55-2.65 (m, 1 H), 2.79 (dd, J = 13.39, 8.34 Hz, 1 H), 2.99 (dd, J = 13.39, 6.06 Hz, 1 H), 3.06-3.16 (m, 1 H), 3.29-3.36 (m, 1 H), 3.69 (b, 1 H), 4.27 (d, J = 11.87 Hz, 1 H), 4.48 (d, J = 13.39 Hz, 1 H), 7.05-7.12 (m, 2 H), 7.13-7.19 (m, 4 H), 7.67 (d, J = 4.29 Hz, 1 H), 7.76-7.84 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A7 | Chiral<br>(S)-N-(5-(3-benzyl-1-methylpiperazine-4-carbonyl)-6,6-dimethyl-1,4,5,6-tetrahydropyrrolo[3,4-c]pyrazol-3-yl)benzofuran-2-carboxamide | 124 | 1H NMR (400 MHz, DMSO-D6) d ppm 1.38-1.85 (m, J = 24.76 Hz, 6 H) 2.68-2.82 (m, 3 H) 2.83-3.06 (m, 3 H) 3.09-3.55 (m, 4 H) 3.95-4.27 (m, 1 H) 4.27-4.62 (m, 2H) 6.51 (s, 1 H) 7.03-7.35 (m, 6 H) 7.44 (t, J = 7.83 Hz, 1 H) 7.62 (d, J = 7.83 Hz, 1 H) 7.69-7.90 (m, 2H) 9.56-10.03 (m, 1 H) 11.16 (s, 1 H). |
| A8 | Chiral<br>(S)-N-(5-(3-benzyl-1-methylpiperazine-4-carbonyl)-6,6-dimethyl-1,4,5,6-tetrahydropyrrolo[3,4-c]pyrazol-3-yl)quinolme-2-carboxamide | 78.1 | 1H NMR (400 MHz, DMSO-d6) d ppm 1.43-1.71 (m, 6 H) 2.55-2.67 (m, J = 12.38 Hz, 1 H) 2.71-2.86 (m, 5 H) 3.37 (s,4H) 4.44-4.67 (m, 2H) 7.15 (d, J = 8.08 Hz, 2 H) 7.25 (d, J = 5.31 Hz, 3 H) 7.63-7.76 (m, 1 H) 7.81-7.93 (m, 1 H) 8.08 (d, J = 8.08 Hz, 1 H) 8.10-8.25 (m, 2 H) 8.59 (d, J = 8.59 Hz, 1 H) 9.41-9.95 (m, 1 H) 10.89 (s, 1 H). |
| A9 | N-(6,6-dimethyl-5-(1-methyl-3-phenylpiperazine-4-carbonyl)-1,4,5,6-3,4-c]pyrazol-3-yl)-3-phenoxybenzamide | 159 | $^1$H NMR (400 MHz, CDCl$_3$) δ ppm 1.38 (s, 3 H), 1.57 (s, 3 H), 2.38-2.47 (m, 4 H), 2.52-2.63 (m, 1 H), 2.89-2.98 (m, 2 H), 3.15-3.33 (m, 2 H), 4.35-4.41 (m, 1 H), 4.77 (d, J = 16 Hz, 1 H), 4.91 (d, J = 16 Hz), 6.95-7.66 (m, 14 H), 9.52 (s, br, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A10 | N-(6,6-dimethyl-5-(2-phenylpiperazine-1-carbonyl)-1,4,5,6-tetrahydropyrrolo[3,4-c]pyrazol-3-yl)-3-phenoxybenzamide | 55.9 | $^1$H NMR (400 MHz, MeOD) δ ppm 1.34 (s, 3 H), 1.59 (s, 3 H), 2.93-3.03 (m, 2 H), 3.12-3.25 (m, 3 H), 3.47 (d, J = 12 Hz, 1 H), 4.12-4.17 (m, 1 H), 4.82 (d, J = 12 Hz, 1 H), 4.97 (d, J = 12 Hz), 7.02-7.75 (m, 14 H). |
| A11 | N-(6,6-dimethyl-5-(octahydropyrrolo[1,2-a]pyrazine-2-carbonyl)-1,4,5,6-tetrahydropyrrolo[3,4-c]pyrazol-3-yl)quinolme-2-carboxamide | 73.9 | 1H NMR (400 MHz, DMSO-D6) d ppm 1.75 (none, 1 H) 1.89-1.99 (m, 1 H) 2.02-2.24 (m, 2 H) 2.73-2.88 (m, 1 H) 2.90-3.08 (m, 2 H) 3.48 (dd, J = 42.95, 12.13 Hz, 2 H) 4.53-4.83 (m, 2 H) 7.76 (t, J = 6.95 Hz, 1 H) 7.87-7.99 (m, 1 H) 8.13 (d, J = 7.33 Hz, 1 H) 8.24 (d, J = 8.08 Hz, 2 H) 8.55-8.79 (m, J = 8.08 Hz, 1 H) 10.64 (s, 1 H) 12.58 (s, 1 H). |
| A12 | Chiral<br><br>N-(5-((3S,8aS)-3-isobutyl-octahydropyrrolo[1,2-a]pyrazine-2-carbonyl)-6,6-dimethyl-1,4,5,6-tetrahydropyrrolo[3,4-c]pyrazol-3-yl)quinolme-2-carboxamide | 103 | 1H NMR (400 MHz, CDCl3) d ppm 0.82-0.89 (m, J = 8.72, 6.69 Hz, 7 H) 1.50-1.88 (m, J = 30.57 Hz, 13 H) 2.82-3.13 (m, 2 H) 3.56 (s, 1 H) 3.80-4.00 (m, J = 5.05 Hz, 1 H) 4.57 (s, 1 H) 4.72 (d, J = 12.88 Hz, 1 H) 7.60 (t, J = 7.45 Hz, 1 H) 7.75 (t, J = 7.33 Hz, 1 H) 7.85 (d, J = 8.08 Hz, 1 H) 8.11 (d, J = 8.59 Hz, 1 H) 8.23-8.39 (m, 2 H) 10.48 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A13 | Chiral<br><br>N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)quinoline-2-carboxamide | 27.7 | 1H NMR (400 MHz, DMSO-D6) d ppm 1.21-1.30 (m, 1 H) 1.42 (s, 3 H) 1.48 (s, 3 H) 1.61-1.69 (m, 2 H) 1.71-1.79 (m, 1 H) 1.89 (d, J = 8.84 Hz, 1 H) 2.05 (dd, J = 10.86, 3.54 Hz, 1 H) 2.25-2.34 (m, 1 H) 2.71-2.79 (m, 1 H) 2.80-2.90 (m, 3H) 2.97 (dd, J = 13.14, 8.08 Hz, 1 H) 3.29-3.41 (m, 1 H) 3.75-3.84 (m, J = 2.02 Hz, 1 H) 4.17 (d, J = 13.14 Hz, 1 H) 4.50 (d, J = 12.88 Hz, 1 H) 6.98-7.07 (m, 1 H) 7.08-7.18 (m, 4 H) 7.64-7.68 (m, 1 H) 7.76-7.84 (m, 1 H) 8.02 (d, J = 7.83 Hz, 1 H) 8.13 (d, J = 8.84 Hz, 1 H) 8.16 (d, J = 8.59 Hz, 1 H) 8.54 (d, J = 8.34 Hz, 1 H). |
| A14 | Chiral<br><br>N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)benzamide | 16.1 | 1H NMR (500 MHz, D2O) d ppm 1.47 (s, 1 H) 1.52 (s, 1 H) 1.59 (s, 3 H) 1.64 (s, 3 H) 1.76 (s, 2 H) 2.04 (s, 2 H) 2.90 (d, J = 4.94 Hz, 1 H) 3.08 (s, 1 H) 3.77 (d, J = 15.66 Hz, 4 H) 3.84 (s, 1 H) 4.48 (s, 2 H) 7.09-7.20 (m, 5 H) 7.22-7.29 (m, 3 H) 7.34-7.40 (m, 3 H) 7.49 (dd, J = 12.50, 8.65 Hz, 3 H) 10.87 (s, 1 H). |
| A15 | N-(6,6-dimethyl-5-(octahydropyrrolo[1,2-a]pyrazine-2-carbonyl)-1,4,5,6-tetrahydropyrrolo[3,4-c]pyrazol-3-yl)thiophene-2-carboxamide | 136 | 1H NMR (400 MHz, CDCl3) d ppm 1.23-1.36 (m, 1 H) 1.59-1.67 (m, J = 2.02 Hz, 6 H) 1.67-1.81 (m, 3H) 1.91-2.05 (m, 1 H) 2.08 (q, J = 8.42 Hz, H) 2.16-2.29 (m, 1 H) 2.50-2.68 (m, 1 H) 2.85-3.05 (m, 3 H) 3.47 (d, J = 12.63 Hz, 1 H) 3.57 (d, J = 12.13 Hz, 1 H) 4.50-4.77 (m, 2 H) 7.37 (t, J = 7.58 Hz, 2 H) 7.46 (t, J = 7.20 Hz, 1 H) 7.81 (d, J = 7.58 Hz, 2 H) 9.46 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A16 | N-(5-(1-(2-hydroxyethyl)piperazine-4-carbonyl)-6,6-dimethyl-1,4,5,6-tetrahydropyrrolo[3,4-c]pyrazol-3-yl)-3-phenoxybenzamide | 113 | $^1$H NMR (500 MHz, D$_2$O) d ppm 1.58 (s, 10 H) 2.36 (s, 1 H) 2.49 (d, J = 6.04 Hz, 2 H) 2.98 (s, 2 H) 4.51 (s, 2 H) 7.02 (d, J = 8.24 Hz, 3 H) 7.14 (s, 3 H) 7.36-7.40 (m, 3 H) 7.44-7.47 (m, 1 H) 7.55 (s, 2 H) 7.73 (s, 1 H) 10.89 (s, 1 H) 12.39 (s, 1 H). |
| A17 | N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-3-methoxybenzamide  Chiral | 16.1 | 1H NMR (500 MHz, D2O) d ppm 1.47 (s, 1 H) 1.52 (s, 1 H) 1.59 (s, 3 H) 1.64 (s, 3 H) 1.76 (s, 2 H) 2.04 (s, 2 H) 2.90 (d, J = 4.94 Hz, 1 H) 3.08 (s, 1 H) 3.77 (d, J = 15.66 Hz, 4 H) 3.84 (s, 1 H) 4.48 (s, 2 H) 7.09 - 7.20 (m, 5 H) 7.22-7.29 (m, 3 H) 7.34-7.40 (m, 3 H) 7.49 (dd, J = 12.50, 8.65 Hz, 3 H) 10.87 (s, 1 H). |
| A18 | N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-4-methoxybenzamide  Chiral | 30.2 | 1H NMR (500 MHz, D2O) d ppm 1.47 (s, 1 H) 1.51 (s, 1 H) 1.59 (s, 3 H) 1.63 (s, 3 H) 1.76 (s, 2 H) 2.03 (s, 2 H) 2.90 (s, 1 H) 3.08 (s, 1 H) 3.78 (d, J = 6.59 Hz, 6 H) 4.48 (d, J = 14.28 Hz, 2 H) 6.98 (dd, J = 11.81, 8.79 Hz, 3 H) 7.18 (d, J = 7.42 Hz, 3 H) 7.21-7.29 (m, 3 H) 7.84 (d, J = 8.52 Hz, 1 H) 7.94 (t, J = 9.34 Hz, 2 H) 9.83 (s, 1 H) 10.70 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A19 | 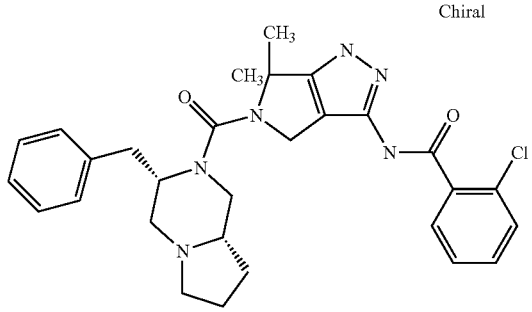<br>Chiral<br>N-(5-((3S,8aS)-3-benzyl-actahydropyrrolo[1,2-a]pyrazine-2-carbonyl)-6,6-dimethyl-1,4,5,6-tetrahydropyrrolo[3,4-c]pyrazol-3-yl)-2-chlorobenzamide | 91.4 | 1H NMR (500 MHz, D2O) d ppm 1.49 (d, J = 16.21 Hz, 2 H) 1.60 (s, 3 H) 1.65 (s, 3 H) 1.76 (s, 1 H) 2.03 (s, 2 H) 2.90 (s, 1 H) 2.94 (s, 1 H) 3.66 (s, 1 H) 3.79 (s, 1 H) 4.48 (s, 2 H) 7.17 (d, J = 7.69 Hz, 3 H) 7.21-7.29 (m, 3 H) 7.36-7.42 (m, 2 H) 7.45 (s, 2 H) 7.49 (d, J = 2.20 Hz, 3 H) 7.73 (d, J = 7.69 Hz, 1 H) 9.82 (s, 1 H) 10.99 (s, 1 H). |
| A20 | 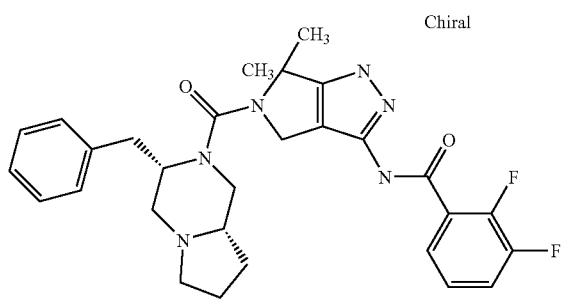<br>Chiral<br>N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-2,3-difluorobenzamide | 50.8 | 1H NMR (500 MHz, D2O) d ppm 1.47 (s, 1 H) 1.51 (s, 1 H) 1.59 (s, 3 H) 1.64 (s, 3 H) 1.77 (s, 2 H) 2.03 (s, 2 H) 2.56 (s, 1 H) 2.88 (d, J = 13.73 Hz, 1 H) 2.95 (d, J = 8.52 Hz, 1 H) 3.07 (s, 1 H) 3.80 (s, 1 H) 4.48 (s, 2 H) 7.18 (t, J = 8.24 Hz, 3 H) 7.23 (s, 1 H) 7.24-7.30 (m, 4 H) 7.39 (s, 1 H) 7.56 (s, 1 H) 7.63 (d, J = 8.24 Hz, 1 H) 9.83 (s, 1 H) 11.03 (s, 1 H). |
| A21 | 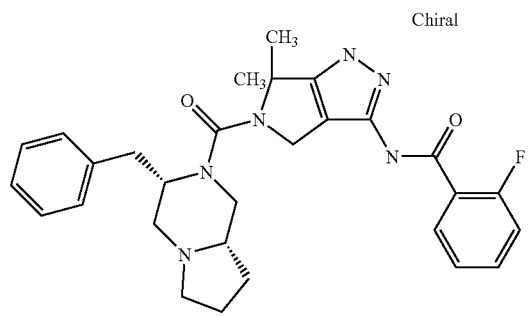<br>Chiral<br>N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-2-fluorobenzamide | 53.2 | 1H NMR (500 MHz, D2O) d ppm 1.47 (s, 1 H) 1.51 (s, 1 H) 1.59 (s, 3 H) 1.64 (s, 3 H) 1.77 (s, 2 H) 2.04 (s, 2 H) 2.56 (s, 1 H) 2.90 (s, 1 H) 3.47 (s, 2 H) 3.66 (s, 1 H) 3.80 (s, 1 H) 4.44 (s, 1 H) 4.50 (d, J = 14.01 Hz, 1 H) 7.18 (t, J = 7.83 Hz, 3 H) 7.24 (s, 1 H) 7.26 (dd, J = 12.77, 5.63 Hz, 5 H) 7.53 (s, 1 H) 7.59 (s, 1 H) 9.83 (s, 1 H) 10.84 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A22 | 3-chloro-N-(6,6-dimethyl-5-(octahydropyrrolo[1,2-a]pyrazine-2-carbonyl)-1,4,5,6-tetrahydropyrrola[3,4-c]pyrazol-3-yl)benzamide | 28.9 | 1H NMR (500 MHz, D2O) d ppm 1.45 (s, 1 H) 1.60 (s, 5 H) 1.89 (s, 1 H) 2.06 (s, 1 H) 3.54 (s, 10 H) 3.71 (s, 1 H) 3.80 (s, 1 H) 4.57 (s, 2 H) 7.50 (t, J = 7.97 Hz, 1 H) 7.61 (s, 1 H) 7.90 (s, 1 H) 7.98 (s, 1 H) 11.03 (s, 1 H). |
| A23 | 6-chloro-N-(6,6-dimethyl-5-(octahydropyrrolo[1,2-a]pyrazine-2-carbonyl)-1,4,5,6-tetrahydropyrrolo[3,4-c]pyrazol-3-yl)picolinamide | 55.9 | 1H NMR (500 MHz, D2O) d ppm 1.45 (s, 1 H) 1.59 (s, 6 H) 1.90 (s, 2 H) 2.06 (s, 1 H) 2.86 (s, 1 H) 2.94 (s, 1 H) 3.55 (s, 6 H) 3.64 (s, 1 H) 3.72 (s, 1 H) 4.61 (s, 2 H) 7.78 (d, J = 7.69 Hz, 1 H) 8.05 (s, 1 H) 8.07 (d, J = 15.38 Hz, 1 H) 10.64 (s, 1 H). |
| A24 | N-(6,6-dimethyl-5-(octahydropyrrolo[1,2-a]pyrazine-2-carbonyl)-1,4,5,6-tetrahydropyrroio[3,4-c]pyrazol-3-yl)picolinamide | 42.9 | 1H NMR (500 MHz, D2O) d ppm 1.45 (s, 1 H) 1.59 (s, 6 H) 1.90 (s, 2 H) 2.06 (s, 1 H) 2.86 (s, 1 H) 3.55 (s, 7 H) 3.65 (s, 1 H) 3.80 (s, 1 H) 4.63 (s, 2 H) 7.66 (dd, J = 6.59, 5.49 Hz, 1 H) 8.02-8.10 (m, 2 H) 8.69 (d, J = 4.40 Hz, 1 H) 10.77 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A25 | 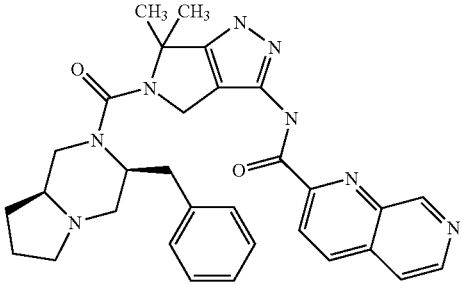<br>N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-1,7-naphthyridine-2-carboxamide | 28.8 | 1H NMR (400 MHz, DMSO-d6) d ppm 1.55 (d, J = 15.41 Hz, 2 H) 1.68 (d, J = 14.65 Hz, 4 H) 1.77-1.90 (m, 2 H) 1.92-2.21 (m, 2 H) 2.59 2.74 (m, 1 H) 2.84-2.98 (m, 1 H) 3.04-3.22 (m, 3 H) 3.65-3.78 (m, 4 H) 3.84-3.98 (m, 1 H) 4.54-4.74 (m, 2 H) 7.19-7.27 (m, 2 H) 7.28-7.41 (m, 3 H) 8.11 (d, J = 6.06 Hz, 1 H) 8.35 (d, J = 8.59 Hz, 1 H) 8.83-8.94 (m, 2 H) 9.59 (s, 1 H) 9.96 (s, 1 H). |
| A26 | 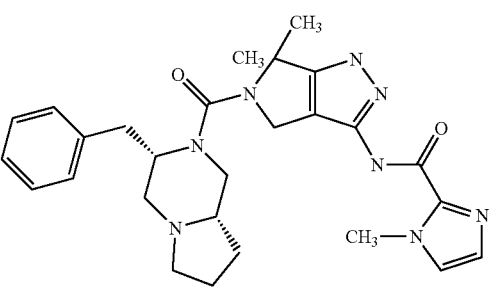<br>N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-1-methyl-1H-imidazole-2-carboxamide | 69.3 | 1H NMR (400 MHz, DMSO-d6) d ppm 1.35 (s, 1 H) 1.50 (s, 2 H) 1.53-1.59 (m, 4 H) 1.60-1.68 (m, 1 H) 1.69-1.81 (m, J = 15.16 Hz, 2 H) 1.85 (dd, J = 13.77, 6.69 Hz, 1 H) 1.99 (d, J = 9.35 Hz, 1 H) 2.12 (dd, J = 10.61, 3.54 Hz, 1 H) 2.88-2.99 (m, 4 H) 3.03-3.17 (m, 1 H) 3.45 (d, J = 17.43 Hz, 1 H) 3.80-3.91 (m, 1 H) 4.01 (s, 3 H) 4.15-4.23 (m, 1 H) 4.46 (d, J = 12.88 Hz, 1 H) 7.08 (s, 1 H) 7.16 (dd, 1 H) 7.20-7.30 (m, 4 H) 7.45 (s, 1 H). |
| A27 | 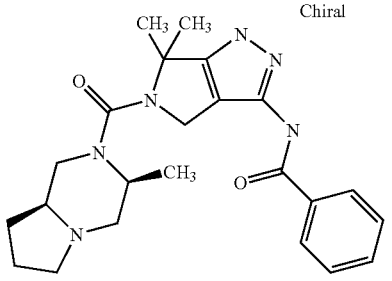<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide | 35.1 | 1H NMR (400 MHz, CD3OD) d ppm 1.35 (d, J = 6.80 Hz, 3 H) 1.41-1.55 (m, 1 H) 1.66-1.96 (m, 9 H) 2.03-2.26 (m, 2 H) 2.40-2.51 (m, 1 H) 2.88-3.08 (m, 3 H) 3.43-3.52 (m, 1 H) 3.92-4.01 (m, 1 H) 4.52-4.82 (m, 2 H) 7.49-7.65 (m, 3 H) 7.96 (d, J = 6.00 Hz, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A28 | N-(6,6-dimethyl-5-((3S,8aS)-3-propyl-octahydropyrrolo[1,2-a]pyrazine-2-carbonyl)-1,4,5,6-tetrahydrapyrrolo[3,4-c]pyrazol-3-yl)benzamide | 96.1 | 1H NMR (400 MHz, CD3OD) d ppm 0.95 (t, J = 7.30 Hz, 3 H) 1.32-1.48 (m, 3 H) 1.63-2.03 (m, J = 31.73 Hz, 12 H) 2.08-2.19 (m, 1 H) 2.36-2.45 (m, 1 H) 2.93-3.08 (m, 3 H) 3.52 (d, J = 9.57 Hz, 1 H) 3.83-3.91 (m, 1 H) 4.50-4.61 (m, 1 H) 4.73-4.83 (m, 1 H) 7.47-7.67 (m, 3 H) 7.95 (d, J = 7.55 Hz, 3 H). |
| A29 | N-(5-(2,6-dimethylpiperazine-4-carbonyl)-6,6-dimethyl-1,4,5,6-tetrahydropyrrolo[3,4-c]pyrazol-3-yl)picolinamide | 77.6 | 1H NMR (400 MHz, DMSO-$d_6$) d ppm 1.11 (d, J = 5.81 Hz, 6 H) 1.64 (s, 6 H) 2.93-3.12 (m, 2 H) 3.38-3.51 (m, J = 12.13 Hz, 4 H) 4.64 (s, 2 H) 7.64-7.79 (m, 1 H) 8.05-8.13 (m, 1 H) 8.15-8.22 (m, 1 H) 8.76 (d, J = 4.55 Hz, 1 H). |
| A30 | 3,5-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide | 22.9 | 1H NMR (500 MHz, D2O) d ppm 1.07 (s, 1 H) 1.19 (s, 1 H) 1.56 (s, 4 H) 1.62 (s, 4 H) 1.82 (s, 2 H) 1.99 (s, 1 H) 3.45 (s, 9 H) 4.54 (s, 2 H) 7.79 (s, 1 H) 7.93 (s, 2 H) 11.12 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A31 | 3-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide | 21.3 | 1H NMR (400 MHz, DMSO-d6) d ppm 1.22 (d, J = 6.82 Hz, 3 H) 1.27-1.40 (m, J = 9.98, 6.95 Hz, 1 H) 1.62 (d, J = 15.66 Hz, 6 H) 1.68-1.81 (m, 3 H) 1.84-2.12 (m, 3 H) 2.29 (s, 1 H) 2.80 (t, J = 10.74 Hz, 2 H) 2.94 (t, J = 7.58 Hz, 1 H) 3.83 (s, 1 H) 4.36-4.68 (m, 2 H) 7.54 (t, J = 7.83 Hz, 1 H) 7.66 (d, J = 8.08 Hz, 1 H) 7.95 (d, J = 7.58 Hz, 1 H) 8.04 (s, 1 H) 11.06 (s, 1 H). |
| A32 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2-fluorobenzamide | 92.4 | 1H NMR (400 MHz, DMSO-d6) d ppm 1.16-1.24 (m, 3 H) 1.26-1.37 (m, 1 H) 1.62 (d, J = 13.89 Hz, 6 H) 1.64-1.77 (m, 3 H) 1.97 (d, J = 8.84 Hz, 3 H) 2.12-2.29 (m, 1 H) 2.69-2.83 (m, 2 H) 2.89-2.99 (m, 1 H) 3.83 (d, J = 5.05 Hz, 1 H) 4.56 (s, 2 H) 7.23-7.38 (m, 2 H) 7.49-7.80 (m, 2 H) 10.87 (s, 1 H). |
| A33 | 5-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2-fluorobenzamide | 82.7 | 1H NMR (400 MHz, DMSO-d6) d ppm 1.22 (d, J = 6.57 Hz, 3 H) 1.35 (d, 1 H) 1.62 (d, J = 14.91 Hz, 6 H) 1.66-1.77 (m, 3 H) 1.86- 2.13 (m, 3 H) 2.15-2.36 (m, 1 H) 2.69- 3.06 (m, 3 H) 3.82 (s, 1 H) 4.36-4.68 (m, 2 H) 7.40 (t, J = 9.22 Hz, 1 H) 7.55-7.74 (m, 2 H) 11.03 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A34 | 3-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-fluorobenzamide | 21.9 | 1H NMR (400 MHz, DMSO-d6) d ppm 1.22 (d, J = 6.57 Hz, 3 H) 1.29-1.35 (m, 1 H) 1.52-1.74 (m, 9 H) 1.81-2.05 (m, 4 H) 2.14-2.31 (m, 1 H) 2.79 (d, J = 10.61 Hz, 2 H) 2.92 (s, 1 H) 3.82 (s, 1 H) 4.31-4.63 (m, 2 H) 7.56 (t, J = 8.84 Hz, 1 H) 7.88-8.11 (m, 1 H) 8.23 (dd, J = 7.07, 2.27 Hz, 1 H) 11.06 (s, 1 H). |
| A35 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2-fluoro-5-(trifluoromethyl)benzamide | 176 | 1H NMR (400 MHz, DMSO-d6) d ppm 1.18-1.40 (m, 4 H) 1.55-1.75 (m, 9 H) 1.81-2.04 (m, 3 H) 2.16-2.27 (m, 1 H) 2.69-2.83 (m, 2 H) 2.92 (t, J = 7.58 Hz, 1 H) 3.84 (s, 1 H) 4.37-4.78 (m, 2 H) 7.59 (t, J = 9.09 Hz, 1 H) 7.84-8.14 (m, 2 H) 11.14 (s, 1 H) 12.42 (s, 1 H). |
| A36 | 3,4-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide | 13.9 | 1H NMR (400 MHz, DMSO-d6) d ppm 1.22 (d, J = 6.57 Hz, 3 H) 1.27-1.41 (m, 1 H) 1.55-1.76 (m, 9 H) 1.80-2.27 (m, 4 H) 2.68-3.01 (m, J = 53.05 Hz, 3 H) 3.78 (s, 1 H) 4.48 (d, J = 5.05 Hz, 2 H) 7.45-7.78 (m, 3 H) 11.29 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A37 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2-fluoro-6-(trifluoromethyl)benzamide | 155 | 1H NMR (400 MHz, DMSO-d6) d ppm 1.22 (d, J = 6.57 Hz, 3 H) 1.26-1.34 (m, 1 H) 1.45-1.76 (m, 9 H) 1.79-2.04 (m, 4 H) 2.22 (dd, J = 10.48, 3.41 Hz, 1 H) 2.67-2.83 (m, 2 H) 2.90-3.02 (m, 1 H) 3.84 (s, 1 H) 4.42-4.64 (m, 2 H) 7.79 (d, J = 8.34 Hz, 1 H) 7.97 (dd, J = 8.34, 2.02 Hz, 1 H) 8.25 (d, J = 2.02 Hz, 1 H) 11.15 (s, 1 H). |
| A38 | 2-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-6-fluorobenzamide | 181 | 1H NMR (400 MHz, DMSO-d6) d ppm 1.19-1.27 (m, 3 H) 1.25-1.38 (m, 1 H) 1.63 (d, J = 11.62 Hz, 6 H) 1.66.1.76 (m, 3 H) 1.79-1.96 (m, 3 H) 2.18 181-2.25 (m, 1 H) 2.67-2.84 (m, 2 H) 2.87-3.01 (m, 1 H) 3.82 (dd, J = 6.44, 2.15 Hz, 1 H) 4.39-4.57 (m, 2 H) 7.20-7.44 (m, 2 H) 7.48-7.59 (m, 1 H) 11.31 (s, 1 H) 12.41 (s, 1 H). |
| A39 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3-methoxybenzamide | 47.4 | 1H NMR (400 MHz, DMSO-d6) d ppm 1.07 (d, J = 6.06 Hz, 3 H) 1.56-1.75 (m, 6 H) 1.83-2.22 (m, 4 H) 3.01-3.68 (m, 8 H) 3.77-3.88 (m, 3 H) 4.49-4.71 (m, 2 H) 7.15 (dd, J = 8.08, 2.53 Hz, 1 H) 7.42 (t, J = 7.83 Hz, 1 H) 7.46-7.62 (m, 2 H) 10.98 (s, 1 H). |
| A40 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-methoxybenzamide | 32.7 | 1H NMR (400 MHz, DMSO-d6) d ppm 1.06 (d, J = 6.06 Hz, 2 H) 1.33 (d, J = 7.07 Hz, 1 H) 1.52-1.76 (m, 6 H) 1.81-2.20 (m, 4 H) 3.02-3.60 (m, 8 H) 3.79-3.91 (m, 3 H) 4.49-4.78 (m, 2 H) 7.04 (d, J = 8.84 Hz, 2 H) 7.98 (d, J = 8.59 Hz, 2 H) 10.80 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A41 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-(trifluoromethoxy)benzamide | 45.4 | 1H NMR (400 MHz, DMSO-d6) d ppm 1.06 (d, J = 6.06 Hz, 2 H) 1.33 (d, J = 7.33 Hz, 1 H) 1.61-1.80 (m, 6 H) 1.88-2.24 (m, 4 H) 3.02-3.86 (m, 8 H) 4.54-4.77 (m, 2 H) 7.51 (d, J = 8.34 Hz, 2 H) 7.99 -8.19 (m, 2 H) 11.12 (s, 1 H). |
| A42 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,3-dimethyl-1H-pyrazole-5-carboxamide | 67.9 | 1H NMR (400 MHz, MeOD) d ppm 1.11-1.25 (m, 2 H) 1.44 (s, 1 H) 1.69 (s, 3 H) 1.76 (s, 3 H) 2.05-2.20 (m, 2 H) 2.26 (s, 3 H) 3.02 (s, 1 H) 3.15-3.27 (m, 2 H) 3.15-3.28 (m, 2 H) 3.34-3.45 (m, J = 12.38 Hz, 2 H) 3.57 (s, 2 H) 3.78-3.91 (m, 1 H) 4.07 (s, 3 H) 4.64-4.75 (m, 2 H) 6.66 (s, 1 H) 7.54 (s, 2 H). |
| A43 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-5-carboxamide | 135 | 1H NMR (400 MHz, MeOD) d ppm 1.17 (s, 2 H) 1.41 (s, 1 H) 1.60-1.82 (m, 6 H) 2.14 (s, 2 H) 2.26 (s, 2 H) 2.66 (s, 2 H) 2.92-3.05 (m, 1 H) 3.12-3.27 (m, 2 H) 3.34-3.43 (m, 1 H) 3.48-3.64 (m, 1 H) 3.76 (d, J = 53.56 Hz, 1 H) 4.59-4.79 (m, 2 H) 7.45 (s, 2 H) 8.53 (s, 1 H) 9.03 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A44 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-4-carboxamide | 43.5 | 1H NMR (400 MHz, MeOD) d ppm 1.34 (d, J = 6.82 Hz, 3 H) 1.73 (d, J = 15.92 Hz, 6 H) 1.81-2.02 (m, H) 2.24 -2.46 (m, 1 H) 2.58 (s, 1 H) 2.86-3.21 (m, 4 H) 3.48 (d, J = 12.38 Hz, 1 H) 3.95 (s, 1 H) 4.58 (s, 5 H) 8.42 (s, 1 H) 9.08 (s, 1 H). |
| A45 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3-trifluoromethoxy)benzamide | 104 | 1H NMR (400 MHz, DMSO-d6) d ppm 1.06 (d, J = 5.81 Hz, 2 H) 1.33 (d, J = 7.07 Hz, 1 H) 1.55-1.73 (m, 6 H) 1.84-2.23 (m, 4 H) 2.94-3.49 (m, 8 H) 4.46-4.75 (m, 2 H) 7.50-7.75 (m, 2 H) 7.86-8.12 (m, 2 H ) 11.22 (s, 1 H). |
| A46 | Chiral<br><br>N-(5-(2,5-dimethylpiperazine-1-carbonyl)-6,6-dimethyl-1,4,5,6-tetrahydropyrrolo[3,4-c]pyrazol-3-yl)picolinamide | 36.2 | 1H NMR (400 MHz, DMSO-d6) d ppm 1.05 (d, J = 5.81 Hz, 3 H) 1.17 (s, 1 H) 1.24 (d, J = 6.32 Hz, 3 H) 1.60 (s, 3 H) 1.68 (s, 3 H) 2.65 (t, J = 11.62 Hz, 1 H) 2.75-2.91 (m, 1 H) 3.18-3.38 (m, 3 H) 4.73 (d, J = 7.58 Hz, 2 H) 7.63-7.75 (m, J = 1.77 Hz, 1 H) 8.08 (d, J = 6.32 Hz, 1 H) 8.15 (d, 1 H) 8.72 (s, 1 H) 8.86-9.06 (m, 1 H) 9.34 (s, 1 H) 10.79 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A47 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-methoxypicolinamide | 65.5 | 1H NMR (400 MHz, DMSO-d6) d ppm 0.93-1.19 (m, 3 H) 1.57-1.74 (m, 6 H) 1.84-2.21 (m, 4 H) 3.02-3.77 (m, 8 H) 3.85-3.98 (m, 3 H) 4.55-4.77 (m, 2 H) 7.18-7.35 (m, 1 H) 7.53-7.72 (m, 1 H) 8.56 (d, J = 5.56 Hz, 1 H). |
| A48 | Chiral<br><br>4-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3-methoxybenzamide | 68.8 | 1H NMR (400 MHz, DMSO-d6) d ppm 0.85-1.14 (m, 3 H) 1.55-1.75 (m, 6 H) 1.77-2.12 (m, 4 H) 2.86-3.14 (m, 3 H) 3.26-3.74 (m, 5 H) 3.89-4.00 (m, 3 H) 4.00-4.16 (m, 1 H) 4.49-4.69 (m, 2 H) 7.43-7.61 (m, 2 H) 7.76 (s, 1 H) 11.15 (s, 2 H). |
| A49 | Chiral<br><br>3-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-fluorobenzamide | 53.6 | 1H NMR (400 MHz, DMSO-d6) d ppm 0.91-1.18 (m, 3 H) 1.56-1.67 (m, 6 H) 1.79-2.08 (m, 4 H) 2.88-3.15 (m, 3 H) 3.17-3.72 (m, 5 H) 4.34-4.71 (m, 2 H) 7.35-7.64 (m, 1 H) 7.88-8.00 (m, 1 H) 8.11-8.26 (m, 1 H) 11.13 (s, 1 H) 11.25 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A50 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-ethylpicolinamide | 82.1 | 1H NMR (400 MHz, DMSO-d6) d ppm 0.99 (d, J = 5.81 Hz, 3 H) 1.08-1.23 (m, 6 H) 1.43-1.70 (m, 4 H) 1.96-2.10 (m, 3 H) 2.60-2.74 (m, 2 H) 2.81-3.10 (m, 4 H) 3.23-3.76 (m, 4 H) 4.45-4.76 (m, 2 H) 7.45-7.56 (m, 1 H) 7.89-8.03 (m, 1 H) 8.55 (d, J = 5.05 Hz, 1 H) 10.51-10.91 (m, 1 H). |
| A51 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4,6-dimethylpicolinamide | 20.9 | 1H NMR (400 MHz, MeOD) d ppm 1.21 (d, J = 6.06 Hz, 3 H) 1.46 (d, J = 7.83 Hz, 1 H) 1.73 (s, 2 H) 1.75 (d, J = 8.34 Hz, 3 H) 1.81 (s, 3 H) 2.05-2.22 (m, 1 H) 2.21-2.35 (m, 2 H) 2.44 (s, 3 H) 2.60 (s, 3 H) 3.11-3.27 (m, J = 3.54 Hz, 1 H) 3.36-3.50 (m, 2 H) 3.50-3.68 (m, 2 H) 3.82-3.99 (m, 1 H) 4.90 (s, 2 H) 7.36 (s, 1 H) 7.82 (s, 1 H). |
| A52 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,5-dimethyl-1H-pyrazole-3-carboxamide | 149 | 1H NMR (400 MHz, MeOD) d ppm 1.10-1.22 (m, 3 H) 1.35-1.46 (m, 2 H) 1.64-1.82 (m, 6 H) 2.03-2.15 (m, 2 H) 2.18-2.25 (m, 2 H) 3.01-3.13 (m, 3 H) 3.29-3.43 (m, 2 H) 3.44-3.65 (m, 3 H) 3.82-3.90 (m, 6 H) 4.72 (s, 2 H) 6.55 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A53 | 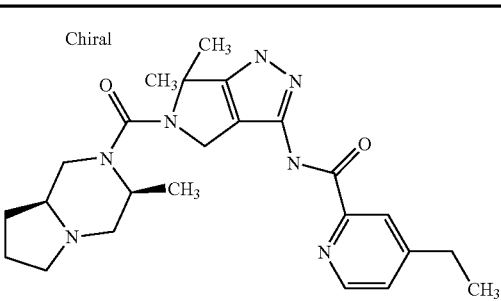 N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-ethylpicolinamide | 66.3 | 1H NMR (400 MHz, DMSO-d6) d ppm 0.99-1.16 (m, 3 H) 1.16-1.32 (m, 6 H) 1.50- 1.82 (m, 2 H) 1.85-2.06 (m, 2 H) 2.07-2.19 (m, 3 H) 2.62-2.84 (m, 2 H) 2.86-3.15 (m, 4 H) 3.36-3.63 (m, 2 H) 3.98-4.13 (m, 2 H) 7.81-7.98 (m, 1 H) 8.04-8.16 (m, 1 H) 8.61 (d, J = 1.52 Hz, 1 H). |
| A54 | 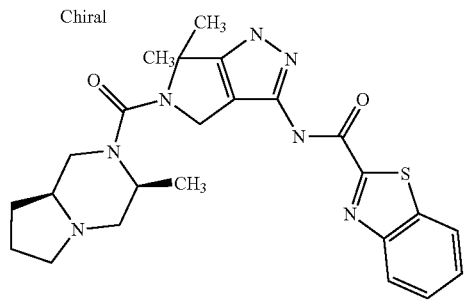 N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzo[d]thiazole-2-carboxamide | 49.9 | 1H NMR (400 MHz, DMSO-d6) d ppm 0.98-1.11 (m, 3 H) 1.17-1.40 (m, 2 H) 1.61-1.78 (m, 2 H) 1.84-2.09 (m, 6 H) 2.83-3.18 (m, 4 H) 3.42-3.63 (m, 4 H) 5.18-5.46 (m, 2 H) 7.44-7.77 (m, 2 H) 7.94-8.37 (m, 2 H) 10.64-11.47 (m, 2 H). |
| A55 | 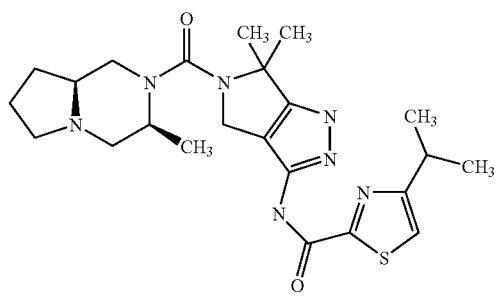 N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-isopropylthiazole-2-carboxamide | 177 | 1H NMR (400 MHz, DMSO-d6) d ppm 0.80-0.92 (m, 1 H) 1.00-1.14 (m, 2 H) 1.15-1.39 (m, 9 H) 1.50 (s, 2 H) 1.57-1.85 (m, 2 H) 1.86-2.09 (m, 2 H) 2.83-3.22 (m, 4 H) 3.33-3.76 (m, 2 H) 3.96-4.29 (m, 3 H) 4.37-4.80 (m, 2 H) 5.24 (s, 1 H) 5.30-5.81 (m, 1 H) 7.51-7.83 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A56 | N-(5-((3S,8aS)-3-(cyclohexylmethyl)-octahydropyrrolo[1,2-a]pyrazine-2-carbonyl)-6,6-dimethyl-1,4,5,6-tetrahydropyrrolo[3,4-c]pyrazol-3-yl)picolinamide | 18.1 | 1H NMR (500 MHz, D2O) d ppm 0.84 (s, 2 H) 1.09 (s, 2 H) 1.38 (s, 1 H) 1.57 (s, 9 H) 1.62 (s, 9 H) 1.78 (s, 2 H) 2.06 (s, 3 H) 3.03 (s, 2 H) 3.74 (s, 1 H) 4.01 (s, 1 H) 4.65 (s, 1 H) 7.65 (s, 1 H) 8.07 (s, 3 H) 8.69 (s, 1 H) 10.77 (d, J = 2.75 Hz, 1 H). |
| A57 | (S)-3-chloro-N-(5-(3,3-dimethyl-octahydropyrrolo[1,2-a]pyrazine-2-carbonyl)-6,6-dimethyl-1,4,5,6-tetrahydropyrrolo[3,4-c]pyrazol-3-yl)benzamide | 87.4 | 1H NMR (500 MHz, D2O) d ppm 1.21 (s, 4 H) 1.43 (s, 5 H) 1.55 (s, 5 H) 1.63 (s, 5 H) 2.09 (s, 3 H) 3.01 (s, 2 H) 3.35 (s, 1 H) 4.59 (s, 2 H) 7.50 (s, 1 H) 7.96 (s, 1 H) 9.70 (s, 1 H) 11.00 (s, 1 H). |
| A58 | 2-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-6-methylpyrimidine-4-carboxamide | 35.3 | $^1$H NMR (400 MHz, DMSO-$d_6$) d ppm 1.05 (d, J = 6.06 Hz, 3 H) 1.13-1.30 (m, 2 H) 1.54-1.78 (m, 6 H) 1.86-2.02 (m, 2 H) 2.62 (s, 3 H) 2.95-3.20 (m, 6 H) 3.95-4.15 (m, 2 H) 4.53-4.77 (m, 2 H) 7.91-8.17 (m, 1 H) 10.97 (s, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A59 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,6-dimethoxypyrimidine-4-carboxamide | 94.5 | $^1$H NMR (400 MHz, DMSO-d$_6$) d ppm 1.05 (d, J = 6.06 Hz, 3 H) 1.17-1.31 (m, J = 7.58, 7.58 Hz, 2 H) 1.38-1.46 (m, J = 4.29 Hz, 1 H) 1.61 (s, 3 H) 1.69 (s, 3 H) 1.84-1.98 (m, J = 7.58 Hz, 1 H) 2.02-2.21 (m, 2 H) 2.98-3.13 (m, 2 H) 3.38-3.50 (m, 2 H) 3.64 (d, J = 57.35 Hz, 2 H) 3.98 (s, 3 H) 4.06 (s, 3 H) 4.54-4.74 (m, 2 H) 7.05 (s, 1 H) 10.72 (s, 1 H). |
| A60 | Chiral<br>3-cyano-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide | 17.1 | 1H NMR (400 MHz, DMSO-d6) d ppm 0.90-1.30 (m, 4 H) 1.40-1.67 (m, J = 22.74 Hz, 6 H) 1.61-2.15 (m, 6 H) 2.67-3.14 (m, J = 54.06 Hz, 3 H) 3.33-3.87 (m, 3 H) 4.55 (s, 2 H) 7.65 (t, J = 7.71 Hz, 1 H) 7.98 (d, J = 7.58 Hz, 1 H) 8.20 (d, J = 7.58 Hz, 1 H) 8.35 (s, 1 H) 11.11 (s, 1 H) 12.47 (s, 1 H). |
| A61 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-ethylbenzamide | 23.8 | 1H NMR (400 MHz, DMSO-d6) d ppm 1.11-1.38 (m, 7 H) 1.51-1.65 (m, 6 H) 1.62-2.27 (m, 6 H) 2.61-3.03 (m, 5 H) 3.83 (s, 1 H) 4.56 (s, 2 H) 7.33 (s, 2 H) 7.91 (d, J = 7.58 Hz, 2 H) 10.80 (s, 1 H) 12.40 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A62 | Chiral<br><br>N-(6,6-dimethyl-5-((3S,8aS)-3-methyl-octahydropyrrolo[1,2-a]pyrazine-2- arbonyl)-1,4,5,6-tetrahydropyrroio[3,4-c]pyrazol-3-yl)-4-fluoro-3-methylbenzamide | 50.8 | 1H NMR (500 MHz, D2O) d ppm 1.04 (s, 2 H) 1.20 (s, 2 H) 1.56 (s, 4 H) 1.58-1.66 (m, 6 H) 1.83 (s, 2 H) 2.01 (s, 2 H) 2.24 (s, 5 H) 3.41 (s, 1 H) 4.55 (s, 2 H) 7.21 (s, 1 H) 7.80 (s, 1 H) 7.90 (s, 1 H) 10.83 (s, 1 H). |
| A63 | Chiral<br><br>N-(6,6-dimethyl-5-((3S,8aS)-3-methyl-octahydropyrrolo[1,2-a]pyrazine-2-carbonyl)-1,4,5,6-tetrahydropyrroio[3,4-c]pyrazol-3-yl)-2,3-difluorobenzamide | 65.4 | 1H NMR (400 MHz, DMSO-d6) d ppm 1.22 (d, J = 6.57 Hz, 3 H) 1.26-1.36 (m, J = 10.61, 6.57 Hz, 1 H) 1.62 (d, J = 13.64 Hz, 6 H) 1.66-1.76 (m, 3 H) 1.80-1.88 (m, 1 H) 1.91-2.02 (m, 1 H) 2.20 (dd, J = 10.48, 3.16 Hz, 1 H) 2.67-2.84 (m, 2 H) 2.89-3.00 (m, 1 H) 3.83 (s, 1 H) 4.34-4.67 (m, 2 H) 7.16-7.36 (m, 1 H) 7.46 (s, 1 H) 7.61 (s, 1 H) 11.07 (s, 1 H). |
| A64 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,3-dihydrobenzofuran-5-carboxamide | 15.9 | 1H NMR (400 MHz, DMSO-d6) d ppm 1.10 (s, 5 H) 1.39-1.91 (m, 13 H) 2.99-3.18 (m, 10 H) 4.04 (q, J = 5.31 Hz, 3 H) 4.33-4.74 (m, J = 8.72, 8.72 Hz, 4 H) 7.83 (s, 2 H) 10.60 (s, 1 H) 12.33 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A65 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3-methylbenzamide | 54.5 | 1H NMR (400 MHz, DMSO-d6) d ppm 0.95-1.28 (m, 3 H) 1.54 (s, 6 H) 1.68-2.03 (m, 4 H) 2.20-2.37 (m, 3 H) 2.79-3.64 (m, 8 H) 4.53 (s, 2 H) 7.32 (s, 2 H) 7.73 (d, J = 15.41 Hz, 2 H) 10.78 (s, 2 H) 12.40 (s, 1 H). |
| A66 | Chiral<br><br>4-cyano-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2-fluorobenzamide | 122 | 1H NMR (400 MHz, DMSO-d6) d ppm 1.18-1.26 (m, J = 6.57, 6.57 Hz, 3 H) 1.25-1.33 (m, 1 H) 1.55-1.64 (m, J = 13.39 Hz, 6 H) 1.74 (d, J = 5.05 Hz, 3 H) 1.79-2.06 (m, 4 H) 2.20 (dd, J = 10.48, 3.41 Hz, 1 H) 2.62-2.96 (m, 4 H) 3.83 (s, 1 H) 4.56 (s, 2 H) 7.82 (s, 2 H) 8.02 (d, J = 9.35 Hz, 1 H) 11.20 (s, 1 H) 12.49 (s, 1 H). |
| A67 | Chiral<br><br>5-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide | 24.3 | 1H NMR (400 MHz, DMSO-d6) d ppm 1.14-1.36 (m, 4 H) 1.47-1.80 (m, 9 H) 1.80-2.03 (m, 3 H) 2.22 (dd, J = 10.61, 3.28 Hz, 1 H) 2.69-2.85 (m, 2 H) 2.87-3.01 (m, 1 H) 3.85 (s, 1 H) 4.42-4.71 (m, 2 H) 8.00-8.34 (m, 2 H) 8.80 (s, 1 H) 12.24 (d, J = 211.96 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A68 | 4-chloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide | 21.3 | 1H NMR (500 MHz, D2O) d ppm 1.09 (s, 2 H) 1.54-1.63 (m, 14 H) 1.84 (s, 2 H) 1.99 (s, 2 H) 4.56 (s, 2 H) 4.61 (S 1 H) 7.80 (s, 2 H) 8.07 (s, 1 H) 8.67 (s, 2 H). |
| A69 | N-(5-((3S,8aS)-3-ethyl-octahydropyrrolo[1,2-a]pyrazine-2-carbonyl)-6,6-dimethyl-1,4,5,6-tetrahydropyrrolo[3,4-c]pyrazol-3-yl)benzamide | 67.8 | 1H NMR (500 MHz, DMSO-d6) d ppm 0.77 (t, J = 7.55 Hz, 1 H) 0.85 (t, J = 7.42 Hz, 3 H) 1.26 (d, J = 10.99 Hz, 1 H) 1.58 (s, 4 H) 1.62-1.69 (m, 6 H) 1.72 (d, J = 7.42 Hz, 2 H) 1.79 (s, 1 H) 1.90 (s, 1 H) 1.97 (d, J = 8.79 Hz, 1 H) 2.18 (d, J = 3.57 Hz, 1 H) 2.70-2.79 (m, 2 H) 2.90 (d, J = 10.99 Hz, 2 H) 3.60 (s, 1 H) 4.43 (s, 1 H) 4.59 (s, 1 H) 7.51 (d, J = 7.14 Hz, 2 H) 7.57 (s, 1 H) 7.98 (d, J = 7.69 Hz, 2 H). |
| A70 | N-(5-((3S,8aS)-3-ethyl-octahydropyrrolo[1,2-a]pyrazine-2-carbonyl)-6,6-dimethyl-1,4,5,6-tetrahydropyrrolo[3,4-c]pyrazol-3-yl)picolinamide | 46.2 | 1H NMR (400 MHz, CD3OD) d ppm 0.96 (t, J = 7.43 Hz, 3 H) 1.12-1.22 (m, 1 H) 1.34-1.49 (m, 1 H) 1.65-2.02 (m, 11 H) 2.04-2.16 (m, 1 H) 2.38 (dd, J = 10.95, 3.90 Hz, 1 H) 2.90-3.08 (m, 3 H) 3.47-3.57 (m, 1 H) 3.72-3.81 (m, 1 H) 4.57-4.67 (m, 1 H) 4.79-4.86 (m, 1 H) 7.63 (dd, J = 7.55, 4.78 Hz, 1 H) 7.96-8.09 (m, 1 H) 8.21 (d, J = 7.55 Hz, 1 H) 8.71 (d, J = 4.78 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A71 | 3-chloro-N-(5-((3S,8aS)-3-ethyl-octahydropyrrolo[1,2-a]pyrazine-2-carbonyl)-6,6-dimethyl-1,4,5,6-tetrahydropyrrolo[3,4-c]pyrazol-3-yl)benzamide | 49.9 | 1H NMR (400 MHz, CD3OD) d ppm 0.95 (t, J = 7.43 Hz, 3 H) 1.33-1.49 (m, 1 H) 1.65-2.02 (m, 12 H) 2.11 (q, J = 8.81 Hz, 1 H) 2.37 (dd, J = 11.20, 3.90 Hz, 1 H) 2.89-3.07 (m, 3 H) 3.47-3.56 (m, 1 H) 3.66-3.82 (m, 1 H) 4.48-4.60 (m, 1 H) 4.72-4.82 (m, 1 H) 7.52 (t, J = 7.93 Hz, 1 H) 7.62 (d, J = 7.93 Hz, 1 H) 7.89 (d, J = 7.93 Hz, 1 H) 7.98 (s, 1 H). |
| A72 | N-(5-((3S,8aS)-3-ethyl-octahydropyrrolo[1,2-a]pyrazine-2-carbonyl)-6,6-dimethyl-1,4,5,6-tetrahydropyrrolo[3,4-c]pyrazol-3-yl)-2-fluorobenzamide | 105 | 1H NMR (500 MHz, DMSO-d6) d ppm 0.85 (t, J = 7.42 Hz, 3 H) 1.26 (d, J = 10.16 Hz, 1 H) 1.57 (s, 3 H) 1.64-1.73 (m, 7 H) 1.88 (s, 2 H) 1.96 (d, J = 8.79 Hz, 1 H) 2.18 (dd, J = 10.71, 3.30 Hz, 1 H) 2.70-2.79 (m, 2 H) 2.90 (d, J = 10.71 Hz, 3 H) 2.99 (s, 1 H) 3.40 (s, 1 H) 4.43 (d, J = 12.64 Hz, 1 H) 4.61 (d, J = 12.64 Hz, 1 H) 7.31 (q, J = 7.33 Hz, 2 H) 7.57 (d, J = 2.20 Hz, 1 H) 7.67 (s, 1 H). |
| A73 | N-(5-((3S,8aS)-3-ethyl-octahydropyrrolo[1,2-a]pyrazine-2-carbonyl)-6,6-dimethyl-1,4,5,6-tetrahydropyrrolo[3,4-c]pyrazol-3-yl)-4-fluorobenzamide | 115 | 1H NMR (500 MHz, DMSO-d6) d ppm 0.85 (t, J = 7.42 Hz, 3 H) 1.27 (s, 1 H) 1.58 (s, 4 H) 1.62-1.69 (m, 6 H) 1.72 (d, J = 7.14 Hz, 2 H) 1.79 (s, 1 H) 1.90 (s, 2 H) 1.97 (d, J = 8.52 Hz, 1 H) 2.19 (d, J = 10.71 Hz, 1 H) 2.90 (d, J = 10.99 Hz, 2 H) 3.59 (s, 2 H) 4.43 (s, 1 H) 4.60 (d, J = 12.91 Hz, 1 H) 7.29-7.37 (m, 2 H) 8.06 (dd, J = 8.24, 5.49 Hz, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
| --- | --- | --- | --- |
| A74 | Chiral<br>4,5-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-2-carboxamide | 10.4 | $^1$H NMR (400 MHz, DMSO-d6) d ppm 1.21 (d, J = 6.57 Hz, 3 H) 1.24-1.36 (m, 1 H) 1.57 (s, 3 H) 1.61 (s, 3 H) 1.63-1.77 (m, 2 H) 1.84 (s, 1 H) 1.98 (d, J = 7.83 Hz, 1 H) 2.21 (d, J = 8.34 Hz, 1 H) 2.70-2.85 (m, 2 H) 2.92 (t, J = 7.71 Hz, 1 H) 3.27-3.44 (m, 2 H) 3.75-3.88 (m, 1 H) 4.37-4.60 (m, 2 H). |
| A75 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,6-dimethylpyrimidine-4-carboxamide | 56.9 | $^1$H NMR (400 MHz, DMSO-d$_6$) d ppm 1.03-1.16 (m, 1 H) 1.23 (d, J = 6.57 Hz, 3 H) 1.30 (dd, J = 10.99, 6.44 Hz, 1 H) 1.59 (s, 3 H) 1.63 (s, 3 H) 1.65-1.77 (m, 3 H) 1.80-1.89 (m, J = 9.09 Hz, 1 H) 1.93-2.04 (m, 1 H) 2.19-2.27 (m, 1 H) 2.55 (s, 3 H) 2.71 (s, 3 H) 2.74-2.84 (m, 2 H) 2.93 (t, J = 7.71 Hz, 1 H) 3.83 (s, 1 H) 4.46-4.70 (m, 2 H) 7.84 (s, 1 H). |
| A76 | Chiral<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)H-pyrrolo[1,2-f]pyrimidme-3-carboxamide | 13.9 | $^1$H NMR (400 MHz, DMSO-d$_6$) d ppm 1.24 (d, J = 6.57 Hz, 3 H) 1.25-1.39 (m, J = 16.67 Hz, 1 H) 1.58 (s, 3 H) 1.62 (s, 3 H) 1.64-1.76 (m, 2 H) 1.80-1.88 (m, 1 H) 1.98 (q, J = 8.59 Hz, 1 H) 2.22 (dd, J = 10.48, 3.41 Hz, 1 H) 2.45-2.57 (m, 2 H) 2.72-2.84 (m, 2 H) 2.93 (t, J = 7.71 Hz, 1 H) 3.85 (d, J = 7.07 Hz, 1 H) 4.46-4.74 (m, 2 H) 6.85 (d, J = 3.28 Hz, 1 H) 7.06 (t, J = 3.16 Hz, 1 H) 7.90 (s, 1 H) 8.24 (s, 1 H) 9.29 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A77 | 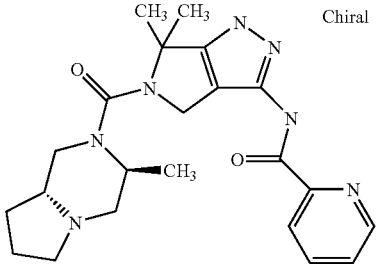<br>N-(6,6-dimethyl-5-((3S,8aR)-3-methyl-octahydropyrrolo[1,2-a]pyrazine-2-carbonyl)-1,4,5,6-tetrahydropyrralo[3,4-c]pyrazol-3-yl)picolinamide | 77.8 | 1H NMR (400 MHz, DMSO-d6) d ppm 0.96 (d, J = 5.81 Hz, 3 H) 1.19-1.34 (m, 1 H) 1.58 (s, 3 H) 1.60-1.66 (m, 1 H) 1.67 (s, 3 H) 1.69-1.80 (m, 2 H) 1.97-2.12 (m, 2 H) 2.34 (t, J = 10.48 Hz, 1 H) 2.90-3.05 (m, 3 H) 3.19-3.25 (m, 1 H) 3.27-3.41 (m, 1 H) 4.66 (q, 2 H) 7.65-7.72 (m, 1 H) 8.02-8.10 (m, 1 H) 8.16 (d, 1 H) 8.72 (d, J = 4.55 Hz, 1 H) 10.12-11.38 (m, 1 H) 11.50-12.80 (m, 1 H). |
| A78 | 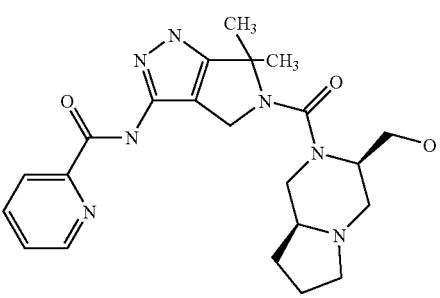<br>N-(5-((3R,8aS)-3-(hydroxymethy)-octahydropyrrolo[1,2-a]pyrazine-2-carbonyl)-6,6-dimethyl-1,4,5,6-tetrahydropyrrolo[3,4-c]pyrazol-3-yl)picolinamide | 165 | 1H NMR (500 MHz, D2O) d ppm 1.57 (s, 7 H) 1.62 (s, 2 H) 1.73 (s, 2 H) 1.83 (s, 1 H) 2.01 (s, 2 H) 3.56 (s, 1 H) 3.70 (s, 1 H) 3.78 (s, 1 H) 4.54 (s, 2 H) 4.66 (s, 2 H) 7.65 (s, 2 H) 8.03 (s, 4 H) 8.69 (s, 2 H) 10.36 (s, 1 H) 11.23 (s, 1 H). |
| A79 | 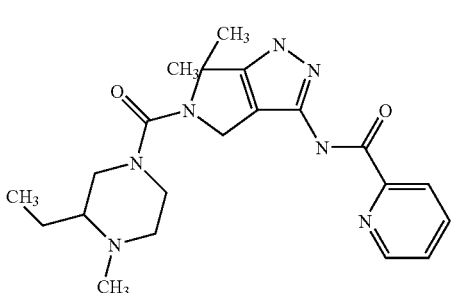<br>N-(5-(2-ethyl-1-methylpiperazine-4-carbonyl)-6,6-dimethyl-1,4,5,6-tetrahydropyrrolo[3,4-c]pyrazol-3-yl)picolinamide | 79.6 | $^1$H NMR (500 MHz, D$_2$O) d ppm 0.90 (s, 5 H) 1.48 (s, 1 H) 1.61 (s, 11 H) 1.90 (s, 1 H) 2.83 (s, 3 H) 4.60 (s, 2 H) 7.65 (s, 2 H) 8.04 (s, 2 H) 8.10 (s, 1 H) 8.69 (s, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A80 | Chiral<br><br>N-(5-((3S,8aR)-3-((S)-sec-butyl)-octahydropyrrolo[1,2-a]pyrazine-2-carbonyl)-6,6-dimethyl-1,4,5,6-tetrahydropyrrolo[3,4-c]pyrazol-3-yl)picolinamide | 129 | 1H NMR (500 MHz, D2O) d ppm 0.81 (s, 10 H) 1.10 (s, 2 H) 1.29 (s, 1 H) 1.59 (s, 8 H) 1.65 (s, 4 H) 1.92 (s, 2 H) 4.65 (s, 2 H) 7.65 (s, 2 H) 8.04 (s, 2 H) 8.11 (s, 1 H) 8.68 (s, 1 H). |
| A81 | Chiral<br><br>(S)-N-(5-(3,3-dimethyl-octahydropyrrolo[1,2-a]pyrazine-2-carbonyl)-6,6-dimethyl-1,4,5,6-tetrahydropyrrolo[3,4-c]pyrazol-3-yl)picolinamide | 125 | 1H NMR (500 MHz, D2O) d ppm 1.12 (s, 3 H) 1.19 (s, 2 H) 1.36 (s, 4 H) 1.54 (s, S H) 1.59 (s, 7 H) 1.92 (s, 1 H) 2.94 (s, 1 H) 4.59 (s, 3 H) 7.65 (s, 2 H) 8.04 (s, 2 H) 8.11 (s, 1 H) 8.68 (s, 1 H). |
| A82 | Chiral<br><br>N-(5-((3R,8aS)-3-((R)-1-tert-butoxyethyl)-octahydropyrrolo[1,2-a]pyrazine-2-carbonyl)-6,6-dimethyl-1,4,5,6-tetrahydropyrrolo[3,4-c]pyrazol-3-yl)picolinamide | 81.8 | 1H NMR (500 MHz, D2O) d ppm 1.00 (s, 4 H) 1.12 (s, 17 H) 1.52 (s, 2 H) 1.57 (s, 2 H) 1.61 (s, 2 H) 1.65 (s, 3 H) 3.84 (s, 1 H) 4.48 (s, 1 H) 4.70 (s, 1 H) 7.65 (s, 1 H) 8.06 (s, 3 H) 8.69 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A83 | Chiral<br><br>N-(5-((2R,5S)-2-(2-hydroxyethyl)-5-methyl-1-propylpiperazine-4-carbonyl)-6,6-dimethyl-1,4,5,6-tetrahydropyrrolo[3,4-c]pyrazol-3-yl)picolinamide | 9.53 | $^1$H NMR (500 MHz, D$_2$O) d ppm 0.85 (s, 5 H) 1.00 (d, J = 5.49 Hz, 5 H) 1.59 (d, J = 14.28 Hz, 10 H) 1.65 (s, 4 H) 4.63 (s, 3 H) 7.65 (s, 2 H) 8.04 (s, 2 H) 8.10 (s, 2 H) 8.68 (s, 2 H). |
| A84 | Chiral<br><br>N-(5-((3S,7R,8aS)-3-((S)-sec-butyl)-7-hydroxy-octahydropyrrolo[1,2-a]pyrazine-2-carbonyl)-6,6-dimethyl-1,4,5,6-tetrahydropyrrolo[3,4-c]pyrazol-3-yl)picolinamide | 139 | 1H NMR (500 MHz, D2O) d ppm 0.79 (d, J = 6.59 Hz, 8 H) 1.06 (s, 1 H) 1.48 (s, 3 H) 1.57 (s, 6 H) 1.64 (s, 2 H) 2.01 (s, 2 H) 4.13 (s, 1 H) 4.34 (s, 1 H) 4.66 (s, 2 H) 7.65 (s, 2 H) 8.03 (s, 2 H) 8.10 (s, 2 H) 8.68 (s, 2 H) 10.33 (s, 1 H). |
| A85 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-nitropicolinamide | 15.2 | 1H NMR (400 MHz, DMSO-d6) d ppm 1.23 (d, J = 6.57 Hz, 3 H) 1.24-1.36 (m, 1 H) 1.58 (s, 3 H) 1.62 (s, 3 H) 1.63-1.78 (m, 4 H) 1.78-1.87 (m, 1 H) 1.90-2.02 (m, 1 H) 2.21 (dd, J = 10.61, 3.28 Hz, 1 H) 2.67-2.82 (m, 2 H) 2.92 (t, 1 H) 3.83 (d, J = 8.59 Hz, 1 H) 4.48-4.66 (m, 2 H) 8.37 (d, J = 8.59 Hz, 1 H) 8.79 (dd, J = 8.59, 2.53 Hz, 1 H) 9.44 (d, J = 2.53 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A86 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3,5-difluoropicolinamide | 74.1 | 1H NMR (400 MHz, DMSO-d6) d ppm 1.23 (d, J = 6.57 Hz, 3 H) 1.30 (dd, J = 10.61, 6.57 Hz,1 H) 1.60 (s, 3 H) 1.63 (s, 3 H) 1.68-1.77 (m, 1.80-1.88 (m, 1 H) 1.95-2.04 (m, 1 H) 2.22 (dd, J = 10.61, 3.54 Hz, 1 H) 2.68-2.85 (m, 2 H) 2.85-3.01 (m, 1 H) 3.70-3.90 (m, 1 H) 4.41-4.69 (m, 2 H) 8.03-8.28 (m, 1 H) 8.65 (d, J = 1.77 Hz, 1 H) 10.86 (s, 1 H) 11.98-12.37 (m, 1 H). |
| A87 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4-(dimethylamino)picolinamide | 32.3 | 1H NMR (400 MHz, DMSO-d6) d ppm 1.22 (d, J = 6.82 Hz, 3 H) 1.24-1.37 (m, J = 10.74, 6.69 Hz, 1 H) 1.57 (s, 3 H) 1.62 (s, 3 H) 1.65-1.77 (m, 2 H) 1.78-1.87 (m, 1 H) 1.97 (q, J = 8.59 Hz, 1 H) 2.23 (dd, J = 10.48, 3.41 Hz, 1 H) 2.71-2.82 (m, 2 H) 2.86-2.98 (m, 2 H) 3.05 (s, 6 H) 3.31 (s, 1 H) 3.84 (d, J = 2.78 Hz, 1 H) 4.40-4.75 (m, 2 H) 6.81 (dd, J = 5.81, 2.78 Hz, 1 H) 7.34 (d, J = 2.78 Hz, 1 H) 8.22 (d, J = 5.81 Hz, 1 H). |
| A88 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoline-2-carboxamide | 17.8 | $^1$H NMR (400 MHz, DMSO-d$_6$) d ppm 1.25 (d, J = 6.57 Hz, 3 H) 1.27-1.38 (m, 1 H) 1.61 (s, 3 H) 1.65 (s, 3 H) 1.66-1.79 (m, J = 10.36 Hz, 2 H) 1.80-1.89 (m, 1 H) 1.94-2.07 (m, 1 H) 2.24 (dd, J = 10.61, 3.79 Hz, 1 H) 2.75-2.86 (m, 2 H) 2.93 (t, J = 9.35 Hz, 1 H) 3.34-3.43 (m, 2 H) 3.87 (s, 1 H) 4.52-4.75 (m, 2 H) 7.73-7.81 (m, 1 H) 7.92 (t, J = 7.45 Hz, 1 H) 8.14 (d, J = 8.34 Hz, 1 H) 8.21-8.30 (m, 2 H) 8.65 (d, J = 8.59 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A89 | Chiral<br><br>N-(5-((+/−)-trans-1-allyl-2,5-dimethylpiperazine-4-carbanyl)-6,6-dimethyl-1,4,5,6-tetrahydropyrrolo[3,4-c]pyrazol-3-yl)picolinamide | 15.7 | $^1$H NMR (400 MHz, DMSO-d$_6$) d ppm 0.94-1.05 (m, 6 H) 1.58 (s, 3 H) 1.67 (s, 3 H) 2.00 (dd, J = 11.12, 9.35 Hz, 1 H) 2.37-2.45 (m, 2 H) 2.74 (dd, J = 11.24, 2.65 Hz, 1 H) 2.88 (dd, J = 14.15, 7.58 Hz, 1 H) 3.01-3.11 (m, 2 H) 3.22-3.42 (m, 1 H) 4.65 (s, 2 H) 5.15 (d, J = 10.11 Hz, 1 H) 5.21 (d, J = 16.93 Hz, 1 H) 5.80-5.95 (m, 1 H) 7.70 (dd, J = 6.95, 5.18 Hz, 1 H) 8.04-8.12 (m, 1 H) 8.14-8.20 (m, 1 H) 8.74 (d, J = 4.29 Hz, 1 H). |
| A90 | N-(5-((3S,8aR)-3-ethyl-octahydropyrrolo[1,2-a]pyrazine-2-carbonyl)-6,6-dimethyl-1,4,5,6-tetrahydropyrrolo[3,4-c]pyrazol-3-yl)picolinamide | 107 | 1H NMR (400 MHz, CD3OD-d4) d ppm 0.92 (t, J = 7.43 Hz, 3 H) 1.40-1.54 (m, 2 H) 1.64-1.97 (m, 10 H) 2.13-2.40 (m, 3 H) 2.56-2.71 (m, 1 H) 3.04-3.22 (m, 3 H) 3.36-3.47 (m, 1 H) 4.76-4.86 (m, 2 H) 7.49-7.71 (m, 1 H) 7.94-8.10 (m, 1 H) 8.21 (d, J = 7.81 Hz, 1 H) 8.71 (d, J = 4.78 Hz, 1 H). |
| A91 | Chiral<br><br>5-bromo-N-(6,6-dimethyl-5-((3S,8aS)-3-methyl-octahydropyrrolo[1,2-a]pyrazine-2-carbonyl)-1,4,5,6-tetrahydropyrrola[3,4-c]pyrazol-3-yl)picolinamide | 20.3 | 1H NMR (400 MHz, DMSO-d6) d ppm 1.22 (d, J = 6.57 Hz, 3 H) 1.24-1.37 (m, 1 H) 1.57 (s, 3 H) 1.61 (s, 3 H) 1.63-1.78 (m, 2 H) 1.78-1.88 (m, 1 H) 1.97 (q, J = 8.67 Hz, 1 H) 2.21 (dd, J = 10.48, 3.41 Hz, 1 H) 2.65-2.83 (m, 2 H) 2.91 (t, 1 H) 3.33 (d, J = 9.60 Hz, 2 H) 3.82 (s, 1 H) 4.42-4.67 (m, 2 H) 8.07 (d, J = 8.34 Hz, 1 H) 8.31 (dd, J = 8.34, 2.27 Hz, 1 H) 8.85 (d, J = 2.27 Hz, 1 H) 10.83 (S, 1 H) 12.07 (S, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A92 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-fluoropicolinamide | 20.3 | 1H NMR (400 MHz, DMSO-d6) d ppm 1.22 (d, J = 6.82 Hz, 3 H) 1.24-1.35 (m, 1 H) 1.57 (s, 3 H) 1.61 (s, 3 H) 1.63-1.77 (m, 2 H) 1.79-1.88 (m, 1 H) 1.92-2.01 (m, 1 H) 2.21 (dd, J = 10.48, 3.41 Hz, 1 H) 2.70-2.83 (m, 2 H) 2.85-2.97 (m, 1 H) 3.33 (dd, J = 12.25, 2.40 Hz, 2 H) 3.75-3.90 (m, 1 H) 4.45-4.70 (m, 2 H) 7.85-8.02 (m, 1 H) 8.22 (dd, J = 8.84, 4.55 Hz, 1 H) 8.72 (d, J = 2.78 Hz, 1 H) 10.74 (s, 1 H) 12.13 (s, 1 H). |
| A93 | N-(5-(+/−)-trans-1-(2-methoxyethyl)-2,5-dimethylpiperazine-4-carbonyl)-6,6-dimethyl-1,4,5,6-tetrahydropyrrolo[3,4-c]pyrazol-3-yl)picolinamide | 63.6 | $^1$H NMR (400 MHz, DMSO-$d_6$) d ppm 0.98 (d, J = 6.06 Hz, 6 H) 1.58 (s, 3 H) 1.67 (s, 3 H) 2.03-2.18 (m, 1 H) 2.33-2.47 (m, 4 H) 2.74-2.88 (m, 2 H) 3.05 (d, J = 9.85 Hz, 2 H) 3.25 (s, 3 H) 3.39-3.49 (m, 3 H) 4.66 (s, 2 H) 7.65-7.80 (m, 1 H) 8.00-8.12 (m, 1 H) 8.17 (d, J = 8.08 Hz, 1 H) 8.66-8.83 (m, 1 H). |
| A94 | N-(5-((+/−)-trans-1-(3-methoxypropyl)-2,5-dimethylpiperazine-4-carbonyl)-6,6-dimethyl-1,4,5,6-tetrahydropyrrolo[3,4-c]pyrazol-3-yl)picolinamide | 23.8 | $^1$H NMR (400 MHz, DMSO-$d_6$) d ppm 0.99 (dd, 6 H) 1.58 (s, 3 H) 1.63 (dd, 1 H) 1.67 (s, 3 H) 1.95-2.09 (m, 1 H) 2.39-2.47 (m, 2 H) 2.70-2.82 (m, 1 H) 2.86-2.99 (m, 1 H) 3.01-3.15 (m, J = 7.83 Hz, 3 H) 3.22 (s, 2 H) 3.33 (s, 4 H) 4.66 (s, 2 H) 5.11-5.28 (m, 1 H) 5.87 (d, J = 15.16 Hz, 1 H) 7.70 (dd, 1 H) 8.08 (t, J = 7.45 Hz, 1 H) 8.17 (d, J = 7.83 Hz, 1 H) 8.73 (d, J = 4.04 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A95 | N-(5-((+/−)-trans-1-ethyl-2,5-dimethylpiperazine-4-carbonyl)-6,6-dimethyl-1,4,5,6-tetrahydropyrrolo[3,4-c]pyrazol-3-yl)picolinamide | 9.11 | $^1$H NMR (400 MHz, DMSO-$d_6$) d ppm 1.00 (d, J = 5.81 Hz, 9 H) 1.58 (s, 3 H) 1.68 (s, 3 H) 1.94-2.10 (m, 1 H) 2.30-2.46 (m, J = 30.57 Hz, 2 H) 2.78 (s, 1 H) 3.02-3.14 (m, 2 H) 3.33 (s, 2 H) 4.66 (s, 2 H) 7.66-7.73 (m, 1 H) 8.03-8.11 (m, 1 H) 8.17 (d, J = 7.58 Hz, 1 H) 8.74 (d, J = 4.29 Hz, 1 H). |
| A96 | N-(6,6-dimethyl-5-((+/−)-trans-1,2,5-trimethylpiperazine-4-carbonyl)-1,4,5,6-tetrahydropyrroio[3,4-c]pyrazol-3-yl)picolinamide | 28.2 | $^1$H NMR (400 MHz, DMSO-$d_6$) d ppm 0.95 (d, J = 6.32 Hz, 3 H) 0.97 (d, J = 6.06 Hz, 3 H) 1.58 (s, 3 H) 1.68 (s, 3 H) 2.03-2.12 (m, 1 H) 2.16 (s, 3 H) 2.33 (t, J = 10.74 Hz, 1 H) 2.37-2.45 (m, 1 H) 2.65-2.70 (m, 1 H) 2.70-2.76 (m, 1 H) 2.95-3.06 (m, 3 H) 4.67 (q, 2 H) 7.65-7.73 (m, 1 H) 8.04-8.11 (m, 1 H) 8.17 (d, J = 7.83 Hz, 1 H) 8.73 (d, J = 4.80 Hz, 1 H). |
| A97 | N-(5-((+/−)-trans-1-isopropyl-2,5-dimethylpiperazine-4-carbonyl)-6,6-dimethyl-1,4,5,6-tetrahydropyrrolo[3,4-c]pyrazol-3-yl)picolinamide | 69.2 | $^1$H NMR (400 MHz, DMSO-$d_6$) d ppm 0.86 (d, J = 6.32 Hz, 3 H) 0.97 (d, J = 2.53 Hz, 3 H) 0.98 (d, J = 2.27 Hz, 3 H) 1.05 (d, J = 6.57 Hz, 3 H) 1.58 (s, 3 H) 1.67 (s, 3 H) 1.97-2.05 (m, 1 H) 2.31-2.41 (m, 1 H) 2.54-2.57 (m, 1 H) 2.57-2.62 (m, 1 H) 2.65-2.74 (m, 1 H) 2.95-3.08 (m, 2 H) 3.10-3.19 (m, 1 H) 4.66 (s, 2 H) 7.70 (dd, J = 6.44, 4.93 Hz, 1 H) 8.04-8.11 (m, 1 H) 8.17 (d, J = 7.83 Hz, 1 H) 8.74 (d, J = 4.55 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A98 | N-(5-((+/−)-trans-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide | 19.1 | $^1$H NMR (400 MHz, DMSO-d$_6$) d ppm 0.03-0.13 (m, 2 H) 0.39-0.54 (m, 2 H) 0.78-0.89 (m, 1 H) 0.97 (d, J = 6.06 Hz, 3 H) 1.00 (d, J = 6.06 Hz, 3 H) 1.58 (s, 2 H) 1.68 (s, 3 H) 2.05-2.21 (m, 2 H) 2.34-2.47 (m, 2 H) 2.96 (dd, J = 11.37, 2.78 Hz, 1 H) 3.01-3.11 (m, 2 H) 4.66 (d, J = 4.04 Hz, 2 H) 7.66-7.76 (m, 1 H) 8.03-8.11 (m, 1 H) 8.17 (d, J = 7.83 Hz, 1 H) 8.73 (d, J = 4.29 Hz, 1 H). |
| A99 | N-(5-(1-(3-hydroxypropyl)-2,5-dimethylpiperazine-4-carbonyl)-6,6-dimethyl-1,4,5,6-tetrahydropyrrolo[3,4-c]pyrazol-3-yl)picolinamide | 19.9 | $^1$H NMR (400 MHz, DMSO-d$_6$) d ppm 0.94-0.98 (m, 2 H) 1.00 (d, J = 6.06 Hz, 3 H) 1.04 (d, J = 6.06 Hz, 3 H) 1.58 (s, 3 H) 1.67 (s, 3 H) 2.00-2.18 (m, 2 H) 2.32-2.46 (m, 2 H) 2.80-2.90 (m, 1 H) 3.05-3.17 (m, 2 H) 3.67-3.79 (m, 1 H) 4.65 (s, 2 H) 7.70 (dd, 1 H) 8.03-8.12 (m, 1 H) 8.17 (d, J = 7.58 Hz, 1 H) 8.73 (d, J = 4.29 Hz, 1 H). |
| A100 | N-(5-((3S,8aS)-3-isopropyl-octahydropyrrolo[1,2-a]pyrazine-2-carbonyl)-6,6-dimethyl-1,4,5,6-tetrahydropyrrolo[3,4-c]pyrazol-3-yl)picolinamide | 14.1 | 1H NMR (400 MHz, CD3OD) d ppm 0.97 (d, J = 6.80 Hz, 6 H) 1.33-1.48 (m, 1 H) 1.63-1.99 (m, 10 H) 1.99-2.21 (m, 1 H) 2.26-2.39 (m, 2 H) 2.90-3.07 (m, 2 H) 3.19-3.27 (m, 1 H) 3.44-3.51 (m, 1 H) 3.55-3.63 (m, 1 H) 4.48-4.64 (m, 1 H) 4.89-4.94 (m, 1 H) 7.57-7.67 (m, 1 H) 7.98-8.06 (m, 1 H) 8.20 (d, J = 7.81 Hz, 1 H) 8.70 (d, J = 4.78 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A101 | 2,4-difluoro-N-(5-((3S,8aS)-3-isopropyl-octahydropyrrolo[1,2-a]pyrazine-2-carbonyl)-6,6-dimethyl-1,4,5,6-tetrahydropyrrolo[3,4-c]pyrazol-3-yl)benzamide | 148 | 1H NMR (400 MHz, CD3OD) d ppm 0.97 (dd, J = 6.55, 3.27 Hz, 6 H) 1.34-1.46 (m, 1 H) 1.65-1.96 (m, 10 H) 2.07-2.16 (m, 1 H) 2.27-2.39 (m, 2 H) 2.92-3.07 (m, 2 H) 3.21-3.27 (m, 1 H) 3.44-3.51 (m, 1 H) 3.56-3.63 (m, 1 H) 4.46-4.56 (m, 1 H) 4.79-4.87 (m, 1 H) 7.07-7.21 (m, 2 H) 7.84-7.95 (m, 1 H). |
| A102 | 2,4-difluoro-N-(5-((2R,5S)-2-(2-hydroxyethyl)-5-methyl-1-propylpiperazine-4-carbonyl)-6,6-dimethyl-1,4,5,6-tetrahydropyrrolo[3,4-c]pyrazol-3-yl)benzamide | 45.9 | 1H NMR (400 MHz, CDCl3-d) d ppm 0.89 (t, J = 7 Hz, 3H), 1.14 (d, J = 4 Hz, 3H), 1.25-1.35 (m, 1H), 1.40-1.60 (m, 2H), 1.60-1.90 (m, 1H), 1.71 (s, 3H), 1.77 (s, 3H), 1.85-2.00 (m, 1H), 2.05-2.20 (m, 1H), 2.25-2.40 (m, 1H), 2.70-2.85 (m, 2H), 2.89-2.93 (m, 1H), 3.05-3.25 (m, 2H), 3.40-3.50 (m, 1H), 3.65-3.90 (m, 2H), 4.05-4.25 (m, 1H), 4.60-4.85 (m, 2H), 6.93 (dd, J = 8.5 Hz, J = 11.6 Hz, 1H), 7.01-7.10 (m, 1H), 8.05-8.20 (m, 1H), 9.00-9.10 (m, 1 H). |
| A103 | Chiral 2-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-4-carboxamide | 12.9 | 1H NMR (400 MHz, DMSO-d6) d ppm 1.21 (d, J = 6.57 Hz, 3 H) 1.23-1.35 (m, 1 H) 1.57 (s, 3 H) 1.60 (s, 3 H) 1.62-1.77 (m, 2 H) 1.78-1.87 (m, 1 H) 1.96 (q, J = 8.59 Hz, 1 H) 2.20 (dd, J = 10.36, 3.54 Hz, 1 H) 2.69-2.82 (m, 2 H) 2.86-2.96 (m, 1 H) 3.25-3.44 (m, J = 9.09 Hz, 2 H) 3.77-3.88 (m, 1 H) 4.40-4.65 (m, 2 H) 8.52 (s, 1 H) 10.66 (s, 1 H) 11.96 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A104 | N-(6,6-dimethyl-5-(((3S,6aS,7aS,7bS)-3-methyl-octahydro-1H-3-aza-bicyclo[3.1.0]hex-1(5)-eno[3,2-a]pyrazine-2-carbonyl)-1,4,5,6-tetrahydropyrrolo[3,4-c]pyrazol-3-yl)picolinamide | 83.7 | 1H NMR (400 MHz, DMSO-d6) d ppm 0.12-0.25 (m, 1 H) 0.66-0.84 (m, 1 H) 1.04 (dd, J = 101.31, 6.32 Hz, 3 H) 1.22-1.38 (m, 2 H) 1.58 (s, 3 H) 1.64 (d, J = 25.52 Hz, 3 H) 2.19-2.43 (m, 3 H) 2.64 (d, J = 10.36 Hz, 1 H) 2.72-2.94 (m, 3 H) 3.08-3.25 (m, 1 H) 3.67-3.82 (m, 1 H) 4.44-4.74 (m, 2 H) 7.64-7.73 (m, 1 H) 8.01-8.11 (m, 1 H) 8.12-8.21 (m, 1 H) 8.66-8.76 (m, 1 H). |
| A105 | Chiral<br>N-(5-((3S,7S,8aS)-7-fluoro-3-methyl-octahydropyrrolo[1,2-a]pyrazine-2-carbonyl)-6,6-dimethyl-1,4,5,6-tetrahydropyrrolo[3,4-c]pyrazol-3-yl)picolinamide | 109 | 1H NMR (400 MHz, CD3OD) d ppm 1.40 (d, J = 6.55 Hz, 3 H) 1.71 (s, 3 H) 1.74 (s, 3 H) 1.97-2.09 (m, 1 H) 2.15-2.46 (m, 3 H) 2.90 (d, J = 10.83 Hz, 1 H) 2.98-3.25 (m, 3 H) 3.47 (d, J = 12.59 Hz, 1 H) 3.92-4.04 (m, 1 H) 4.65-4.81 (m, 2 H) 5.02-5.24 (m, 1 H) 7.58-7.66 (m, 1 H) 7.99-8.06 (m, 1 H) 8.20 (d, J = 7.81 Hz, 1 H) 8.67-8.75 (m, 1 H). |
| A106 | N-(5-(+/−)-trans-2,5-dimethyl-1-propylpiperazine-4-carbonyl)-6,6-dimethyl-1,4,5,6-tetrahydropyrrolo[3,4-c]pyrazol-3-yl)picolinamide | 39.5 | $^1$H NMR (400 MHz, DMSO-d$_6$) d ppm 0.85 (t, J = 7.33 Hz, 3 H) 0.97 (d, J = 5.31 Hz, 3 H) 0.99 (d, J = 6.32 Hz, 3 H) 1.36-1.49 (m, 2 H) 1.58 (s, 3 H) 1.67 (s, 3 H) 1.95 (t, 1 H) 2.10-2.22 (m, 1 H) 2.41 (d, J = 6.57 Hz, 2 H) 2.52-2.64 (m, 1 H) 2.79 (dd, J = 11.12, 2.78 Hz, 1 H) 3.02-3.14 (m, 2 H) 4.65 (s, 2 H) 7.70 (dd, 1 H) 8.08 (t, 1 H) 8.17 (d, J = 7.83 Hz, 1 H) 8.73 (d, J = 4.29 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A107 | 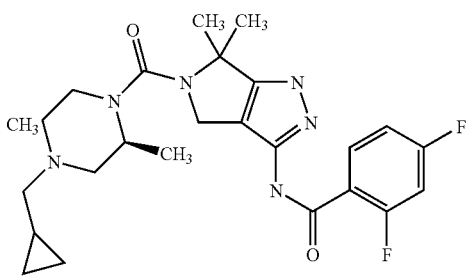 N-(5-(+/−)-trans-1-(cyclopropylmethyl)-2,5-dimethylpiperazine-4-carbonyl)-6,6-dimethyl-1,4,5,6-tetrahydropyrrolo[3,4-c]pyrazol-3-yl)-2,4-difluorobenzamide | 68.9 | $^1$H NMR (400 MHz, DMSO-d$_6$) d ppm 0.06 (d, J = 4.80 Hz, 2 H) 0.45 (dd, J = 7.96, 3.66 Hz, 2 H) 0.76-0.88 (m, J = 4.55 Hz, 1 H) 0.96 (d, J = 5.81 Hz, 3 H) 0.98 (d, J = 5.81 Hz, 3 H) 1.59 (s, 3 H) 1.68 (s, 3 H) 2.04-2.21 (m, 2 H) 2.31-2.45 (m, 2 H) 2.88-2.99 (m, 1 H) 3.00-3.09 (m, 2 H) 3.17 (d, J = 3.28 Hz, 1 H) 4.59 (s, 2 H) 7.20 (t, J = 7.83 Hz, 1 H) 7.39 (t, J = 8.97 Hz, 1 H) 7.67-7.84 (m, 1 H) 10.92 (s, 1 H). |
| A108 | 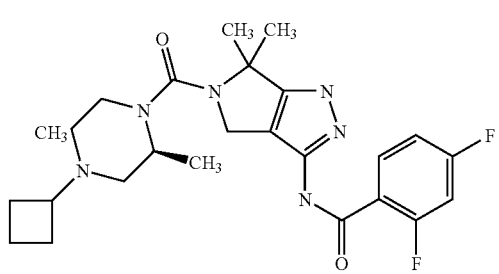 N-(5-((+/−)-trans-1-cyclobutyl-2,5-dimethylpiperazine-4-carbonyl)-6,6-dimethyl-1,4,5,6-tetrahydropyrrolo[3,4-c]pyrazol-3-yl)-2,4-difluorobenzamide | 74.2 | $^1$H NMR (400 MHz, DMSO-d$_6$) d ppm 0.92 (d, J = 6.32 Hz, 3 H) 1.03 (d, J = 6.32 Hz, 3 H) 1.50-1.60 (m, 5 H) 1.67 (s, 3 H) 1.76-1.69 (m, 3 H) 1.92-2.07 (m, 1 H) 2.40-2.47 (m, 1 H) 2.53-2.58 (m, J = 7.07 Hz, 1 H) 2.61-2.71 (m, 1 H) 2.91-3.01 (m, 1 H) 3.00-3.13 (m, 1 H) 3.17-3.27 (m, 2 H) 4.57 (s, 2 H) 7.20 (s, 1 H) 7.39 (s, 1 H) 7.73 (s, 1 H) 10.89 (s, 1 H) 12.44 (s, 1 H). |
| A109 | 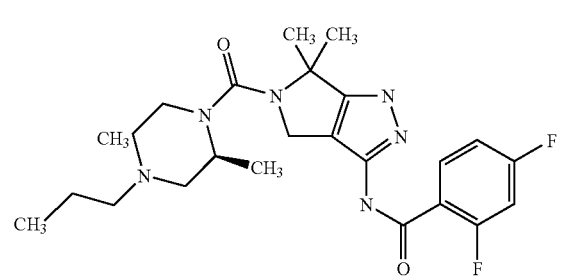 N-(5-((+/−)-trans-1-butyl-2,5-dimethylpiperazine-4-carbonyl)-6,6-dimethyl-1,4,5,6-tetrahydropyrrolo[3,4-c]pyrazol-3-yl)-2,4-difluorobenzamide | 54.9 | $^1$H NMR (400 MHz, DMSO-d$_6$) d ppm 0.84-0.90 (m, 3 H) 0.93-0.97 (m, 3 H) 0.98 (d, J = 6.06 Hz, 3 H) 1.18-1.33 (m, 2 H) 1.31-1.43 (m, 2 H) 1.58 (s, 3 H) 1.67 (s, 3 H) 1.91-1.98 (m, 1 H) 2.11-2.23 (m, 1 H) 2.34-2.44 (m, 1 H) 2.54-2.65 (m, 1 H) 2.76 (dd, J = 11.12, 2.78 Hz, 1 H) 3.05 (t, J = 9.22 Hz, 1 H) 3.16 (s, 2 H) 4.59 (s, 2 H) 7.20 (t, J = 7.71 Hz, 1 H) 7.39 (t, J = 9.47 Hz, 1 H) 7.68-7.82 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A110 | N-(5-((+/−)-trans-1-(cyclopentylmethyl)-2,5-dimethylpiperazine-4-carbonyl)-6,6-dimethyl-1,4,5,6-tetrahydropyrrolo[3,4-c]pyrazol-3-yl)-2,4-difluorobenzamide | 81.3 | $^1$H NMR (400 MHz, DMSO-d$_6$) d ppm 0.92 (d, J = 6.32 Hz, 3 H) 1.03 (d, J = 6.32 Hz, 3 H) 1.50-1.60 (m, 5 H) 1.67 (s, 3 H) 1.76-1.89 (m, 3 H) 1.92-2.07 (m, 1 H) 2.40-2.47 (m, 1 H) 2.53-2.58 (m, J = 7.07 Hz, 1 H) 2.61-2.71 (m, 1 H) 2.91-3.01 (m, 1 H) 3.00-3.13 (m, 1 H) 3.17-3.27 (m, 2 H) 4.57 (s, 2 H) 7.20 (s, 1 H) 7.39 (s, 1 H) 7.73 (s, 1 H) 10.89 (s, 1 H) 12.44 (s, 1 H). |
| A111 | Chiral<br>N-(5-((3S,7S,8aS)-7-methoxy-3,8,8-trimethyl-octahydropyrrolo[1,2-a]pyrazine-2-carbonyl)-6,6-dimethyl-1,4,5,6-tetrahydropyrrolo[3,4-c]pyrazol-3-yl)picolinamide | 177 | 1H NMR (400 MHz, DMSO-d6) d ppm 0.82-0.90 (m, 3 H) 0.91-0.97 (m, 1 H) 1.03 (s, 3 H) 1.22 (d, J = 6.57 Hz, 3 H) 1.58 (s, 3 H) 1.61 (s, 3 H) 1.78 (dd, J = 10.61, 2.53 Hz, 1 H) 2.19 (dd, J = 10.36, 3.28 Hz, 1 H) 2.32 (dd, J = 9.85, 8.34 Hz, 1 H) 2.71 (d, J = 10.36 Hz, 1 H) 2.78-2.87 (m, 2 H) 3.08 (dd, J = 12.38, 2.27 Hz, 1 H) 3.22-3.25 (m, 3 H) 3.38 (dd, J = 8.08, 3.03 Hz, 2 H) 3.74 (d, J = 3.54 Hz, 1 H) 4.58 (d, J = 3.54 Hz, 1 H) 7.58-7.76 (m, 1 H) 8.02-8.11 (m, 1 H) 8.11-8.20 (m, 1 H) 8.72 (d, J = 4.29 Hz, 1 H). |
| A112 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-tetrahydro-2H-pyran-2-carboxamide | 186 | 1H NMR (400 MHz, DMSO-d6) d ppm 1.14-1.22 (m, J = 7.07 Hz, 3 H) 1.25-1.46 (m, 2 H) 1.47-1.52 (m, 3 H) 1.54 (s, 3 H) 1.58 (s, 3 H) 1.60-1.73 (m, 2 H) 1.75-1.85 (m, 3 H) 1.91-2.05 (m, 1 H) 2.06-2.31 (m, 1 H) 2.66-2.86 (m, 2 H) 2.86-3.01 (m, 1 H) 3.23-3.37 (m, 2 H) 3.40-3.53 (m, 1 H) 3.76 (s, 1 H) 3.86-4.03 (m, 2 H) 4.33-4.57 (m, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A113 | Chiral<br>N-(6,6-dimethyl-5-((2R,5S)-1,2,5-trimethylpiperazine-4-carbonyl)-1,4,5,6-tetrahydropyrrolo[3,4-c]pyrazol-3-yl)picolinamide | 13.9 | 1H NMR (400 MHz, DMSO-d6) d ppm 0.96 (d, J = 6.06 Hz, 3 H) 0.99 (d, J = 6.06 Hz, 3 H) 1.59 (s, 3 H) 1.68 (s, 3 H) 1.92-2.01 (m, 1 H) 2.08-2.17 (m, 1 H) 2.20 (s, 3 H) 2.35 (t, J = 10.48 Hz, 1 H) 2.67-2.82 (m, J = 9.09 Hz, 1 H) 2.95-3.12 (m, 2 H) 4.59-4.79 (m, 2 H) 7.65-7.79 (m, 1 H) 8.02-8.13 (m, 1 H) 8.13-8.21 (m, 1 H) 8.74 (d, J = 4.29 Hz, 1 H). |
| A114 | Chiral<br>N-(6,6-dimethyl-5-{[(2S)-2,4,5,5-tetramethylpiperazin-1 yl]carbonyl}-1,4,5,6-tetrahydropyrrolo[3,4-c]pyrazol-3-yl)-2,4-difluorobenzamide | 87.1 | 1H NMR (400 MHz, DMSO-d6) d ppm 0.82-0.89 (m, 3 H) 0.92-1.00 (m, 6 H) 1.43-1.54 (m, 3 H) 1.55-1.66 (m, 3 H) 1.96-2.05 (m, 3 H) 2.02-2.25 (m, 2 H) 2.45-2.56 (m, 2 H) 2.65-2.87 (m, 2 H) 4.39-4.68 (m, 2 H) 7.13 (t, J = 7.58 Hz, 1 H) 7.32 (t, J = 9.35 Hz, 1 H) 7.65 (q, J = 7.58 Hz, 1 H) 10.83 (s, 1 H) 12.37 (s, 1 H). |
| A115 | N-(5-((+/−)-trans-1-ethyl-2,5-dimethylpiperazine-4-carbonyl)-6,6-dimethyl-1,4,5,6-tetrahydropyrrolo[3,4-c]pyrazol-3-yl)-2,4-difluorobenzamide | 83.1 | $^1$H NMR (400 MHz, DMSO-$d_6$) d ppm 0.90-1.04 (m, J = 6.06 Hz, 9 H) 1.58 (s, 3 H) 1.68 (s, 3 H) 2.28-2.35 (m, 1 H) 2.36-2.42 (m, 1 H) 2.53-2.59 (m, 2 H) 2.69-2.80 (m, 2 H) 2.99-3.11 (m, 2 H) 4.61 (s, 2 H) 7.20 (s, 1 H) 7.39 (s, 1 H) 7.74 (s, 1 H) 10.90 (s, 1 H) 12.46 (s, 1 H). |
| A116 | N-(5-((+/−)-trans-2,5-dimethyl-1-propylpiperazine-4-carbonyl)-6,6-dimethyl-1,4,5,6-tetrahydropyrrolo[3,4-c]pyrazol-3-yl)-2,4-difluorobenzamide | 87.3 | $^1$H NMR (400 MHz, DMS0-$d_6$) d ppm 0.83 (t, J = 7.33 Hz, 3 H) 0.95 (d, J = 5.56 Hz, 3 H) 0.98 (d, J = 6.06 Hz, 3 H) 1.31-1.48 (m, 2 H) 1.58 (s, 3 H) 1.67 (s, 3 H) 1.95 (dd, J = 10.86, 9.35 Hz, 1 H) 2.08-2.19 (m, 1 H) 2.31-2.42 (m, 2 H) 2.54-2.60 (m, 1 H) 2.77 (dd, J = 11.12, 2.53 Hz, 1 H) 3.00-3.11 (m, J = 8.97, 8.97 Hz, 2 H) 4.59 (s, 2 H) 7.20 (t, J = 7.96 Hz, 1 H) 7.39 (t, J = 8.46 Hz, 1 H) 7.67-7.82 (m, 1 H) 10.90 (s, 1 H) 12.46 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A117 | 2,4-difluoro-N-(5-((+/−)-trans-1-(3-methoxypropyl)-2,5-dimethylpiperazine-4-carbonyl)-6,6-dimethyl-1,4,5,6-tetrahydropyrrolo[3,4-c]pyrazol-3-yl)benzamide | 131 | $^1$H NMR (400 MHz, DMSO-$d_6$) d ppm 0.95 (d, J = 5.31 Hz, 3 H) 0.98 (d, J = 6.06 Hz, 3 H) 1.58 (s, 3 H) 1.59-1.64 (m, 2 H) 1.67 (s, 3 H) 1.90-2.01 (m, 1 H) 2.13-2.26 (m, 1 H) 2.32-2.44 (m, 2 H) 2.58-2.72 (m, 1 H) 2.72-2.82 (m, 1 H) 2.99-3.11 (m, 2 H) 3.22 (s, 3 H) 3.27-3.39 (m, 2 H) 4.59 (s, 2 H) 7.21 (t, 1 H) 7.39 (t, J = 9.35 Hz, 1 H) 7.70-7.84 (m, 1 H) 10.92 (s, 1 H) 12.46 (s, 1 H). |
| A118 | Chiral<br>N-(5-{[(2S,5S)-4-ethyl-2,5-dimethylpiperazin-1-yl]carbonyl}-6,6-dimethyl-1,4,5,6-tetrahydropyrrolo[3,4-c]pyrazol-3-yl)pyridine-2-carboxamide | 149 | 1H NMR (400 MHz, DMSO-d6) d ppm 0.86 (t, J = 7.07 Hz, 3 H) 0.94 (d, J = 6.06 Hz, 3 H) 1.10 (d, J = 6.57 Hz, 3 H) 1.52 (s, 3 H) 1.56 (s, 3 H) 1.83 (s, 3 H) 2.09-2.36 (m, 3 H) 2.49 (dd, J = 11.24, 3.41 Hz, 1 H) 2.57-2.74 (m, 2 H) 2.93 (dd, J = 12.51 2.40 Hz, 1 H) 3.45-3.61 (m, 1 H) 4.44-4.66 (m, 2 H) 7.50-7.69 (m, 1 H) 7.89-8.03 (m, 1 H) 8.05-8.16 (m, 1 H) 8.67 (d, J = 4.04 Hz, 1 H). |
| A119 | Chiral<br>N-(5-{[(2S,5S)-2,5-dimethyl-4-propylpiperazin-1-yl]carbonyl}-6,6-dimethyl-1,4,5,6-tetrahydropyrrolo[3,4-c]pyrazol-3-yl)pyridine-2-carboxamide | 52.5 | 1H NMR (400 MHz, DMSO-d6) ppm 0.77 (t, J = 7.33 Hz, 3 H) 0.94 (d, J = 6.06 Hz, 3 H) 1.11 (d, J = 6.57 Hz, 3 H) 1.24-1.38 (m, 3 H) 1.44-1.61 (m, 6 H) 1.97-2.10 (m, 1 H) 2.16-2.35 (m, 2 H) 2.52 (dd, J = 10.86, 3.28 Hz, 2 H) 2.59-2.75 (m, 1 H) 2.94 (dd, J = 12.51, 2.65 Hz, 1 H) 3.48-3.66 (m, 1 H) 4.31-4.63 (m, 2 H) 7.49-7.70 (m, 1 H) 7.93-8.05 (m, 1 H) 8.08-8.15 (m, 1 H) 8.67 (d, J = 4.04 Hz, 1 H) 10.74 (s, 1 H) 12.09 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A120 | Chiral<br><br>N-(5-((2R,5S)-1-ethyl-2,5-dimethylpiperazine-4-carbonyl)-6,6-dimethyl-1,4,5,6-tetrahydropyrrolo[3,4-c]pyrazol-3-yl)picolinamide | 19.5 | $^1$H NMR (400 MHz, DMSO-$d_6$) d ppm 0.91-1.03 (m, 9 H) 1.58 (s, 3 H) 1.67 (s, 3 H) 1.99 (dd, J = 10.99, 9.73 Hz, 1 H) 2.32 (dd, J = 12.88, 6.82 Hz, 1 H) 2.37-2.44 (m, 2 H) 2.66-2.82 (m, 2 H) 3.00-3.11 (m, 2 H) 4.66 (d, J = 2.53 Hz, 2 H) 7.65-7.73 (m, 1 H) 8.03-8.12 (m, 1 H) 8.12-8.22 (m, 1 H) 8.73 (d, J = 4.29 Hz, 1 H). |
| A121 | Chiral<br><br>N-(5-((2R,5S)-2,5-dimethyl-1-propylpiperazine-4-carbonyl)-6,6-dimethyl-1,4,5,6-tetrahydropyrrolo[3,4-c]pyrazol-3-yl)picolinamide | 14.6 | $^1$H NMR (400 MHz, DMSO-$d_6$) d ppm 0.85 (t, J = 7.33 Hz, 3 H) 0.93-1.04 (m, 6 H) 1.33-1.46 (m, 2 H) 1.58 (s, 3 H) 1.67 (s, 3 H) 1.96-2.02 (m, 1 H) 2.09-2.25 (m, J = 5.31 Hz, 1 H) 2.37-2.46 (m, 2 H) 2.79 (dd, J = 11.37, 2.78 Hz, 1 H) 3.00-3.14 (m, 3 H) 4.65 (s, 2 H) 7.70 (dd, J = 6.82, 5.31 Hz, 1 H) 8.01-8.12 (m, 1 H) 8.13-8.24 (m, 1 H) 8.73 (d, J = 4.55 Hz, 1 H). |
| A122 | Chiral<br><br>N-(5-((2R,SS)-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide | 13.3 | $^1$H NMR (400 MHz, DMSO-$d_6$) d ppm −0.04-0.14 (m, 2 H) 0.40-0.54 (m, 2 H) 0.84 (s, 1 H) 0.98 (dd, J = 10.86, 6.06 Hz, 6 H) 1.58 (s, 3 H) 1.68 (s, 3 H) 2.04-2.21 (m, 2 H) 2.56-2.73 (m, 1 H) 2.91-3.01 (m, 1 H) 3.01-3.10 (m, 2 H) 3.41-3.56 (m, 2 H) 4.66 (d, J = 3.54 Hz, 2 H) 7.62-7.74 (m, 1 H) 7.99-8.13 (m, 1 H) 8.14-8.21 (m, 1 H) 8.73 (d, J = 4.29 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A123 | Chiral 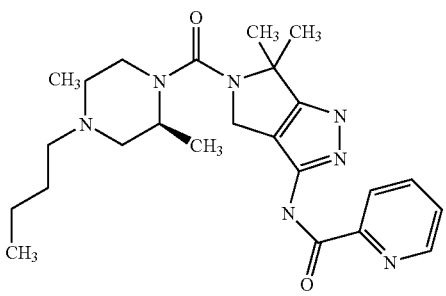<br>N-(5-((2R,5S)-1-butyl-2,5-dimethylpiperazine-4-carbonyl)-6,6-dimethyl-1,4,5,6-tetrahydropyrrolo[3,4-c]pyrazol-3-yl)picolinamide | 13.3 | $^1$H NMR (400 MHz, DMSO-d$_6$) d ppm 0.89 (t, J = 7.20 Hz, 3 H) 0.98 (dd, J = 10.48, 5.68 Hz, 6 H) 1.21-1.34 (m, 2 H) 1.32-1.45 (m, 2 H) 1.58 (s, 3 H) 1.67 (s, 3 H) 1.97 (dd, J = 10.99, 9.22 Hz, 1 H) 2.12-2.24 (m, 1 H) 2.41 (d, J = 6.57 Hz, 2 H) 2.56-2.67 (m, 1 H) 2.78 (dd, J = 11.12, 2.78 Hz, 1 H) 2.99-3.11 (m, 2 H) 4.65 (s, 2 H) 7.70 (dd, J = 6.95, 5.43 Hz, 1 H) 8.01-8.12 (m, 1 H) 8.13-8.26 (m, 1 H) 8.73 (d, J = 4.55 Hz, 1 H). |
| A124 | Chiral 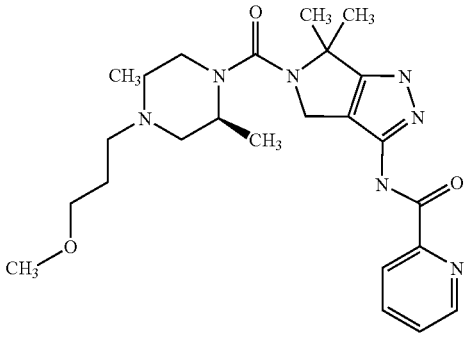<br>N-(5-{[(2S,5S)-4-(3-methoxypropyl)-2,5-dimethylpiperazln-1-yl]carbonyl}-6,6-dimethyl-1,4,5,6-tetrahydropyrrolo[3,4-c]pyrazol-3-yl)pyridine-2-carboxamide | 143 | 1H NMR (400 MHz, DMSO-d6) d ppm 0.85-1.00 (m, 3 H) 1.11 (d, J = 6.32 Hz, 3 H) 1.54 (d, J = 15.16 Hz, 8 H) 1.99-2.15 (m, 1 H) 2.16-2.34 (m, 2 H) 2.52 (dd, J = 11.24, 2.91 Hz, 1 H) 2.59-2.77 (m, 2 H) 2.94 (d, J = 10.36 Hz, 1 H) 3.22-3.36 (m, 4 H) 3.54 (d, J = 5.56 Hz, 1 H) 4.43-4.66 (m, 2 H) 7.42-7.74 (m, 1 H) 8.01 (t, J = 7.71 Hz, 1 H) 8.06-8.15 (m, 1 H) 8.67 (d, J = 4.04 Hz, 1 H) 10.40-11.17 (m, 1 H) 12.09 (s, 1 H). |
| A125 | Chiral 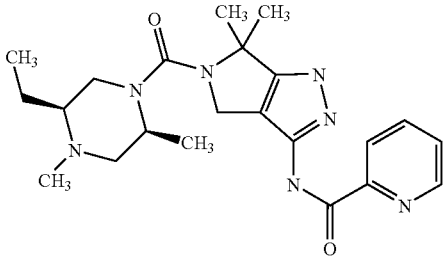<br>N-(5-{[(2S,5S)-5-ethyl-2,4-dimethylpiperazin-1-yl]carbonyl}-6,6-dimethyl-1,4,5,6-tetrahydropyrrolo[3,4-c]pyrazol-3-yl)pyridine-2-carboxamide | 93.9 | 1H NMR (400 MHz, DMSO-d6) d ppm 0.80 (t, J = 7.45 Hz, 3 H) 1.15 (d, J = 6.57 Hz, 3 H) 1.24-1.38 (m, 1 H) 1.54 (d, J = 10.61 Hz, 6 H) 1.81 (s, 2 H) 2.07 (s, 3 H) 2.15-2.32 (m, 1 H) 2.50 (d, J = 11.12 Hz, 1 H) 2.66-2.84 (m, 1 H) 3.03 (d, J = 12.63 Hz, 1 H) 3.57-3.73 (m, 1 H) 4.37-4.59 (m, 2 H) 7.47-7.78 (m, 1 H) 8.01 (t, J = 7.58 Hz, 1 H) 8.05-8.17 (m, 1 H) 8.67 (d, J = 4.55 Hz, 1 H) 10.76 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A126 | Chiral<br>N-(5-((2R,5S)-1-ethyl-2,5-dimethylpiperazine-4-carbonyl)-6,6-dimethyl-1,4,5,6-tetrahydropyrrolo[3,4-c]pyrazol-3-yl)-5-fluoropicolinamide | 22.2 | 1H NMR (400 MHz, DMSO-d6) d ppm 0.90-1.03 (m, 9 H) 1.57 (s, 3 H) 1.66 (s, 3 H) 1.97 (dd, J = 10.99, 9.47 Hz, 1 H) 2.30 (dd, J = 13.01, 6.95 Hz, 1 H) 2.34-2.43 (m, 2 H) 2.62-2.81 (m, 2 H) 2.96-3.19 (m, 2 H) 4.63 (s, 2 H) 7.92-8.04 (m, 1 H) 8.24 (dd, J = 8.59, 4.55 Hz, 1 H) 8.73 (d, J = 1.77 Hz, 1 H). |
| A127 | N-(5-(1-(cyclopropylmethyl)-2-methylpiperazine-4-carbonyl)-6,6-dimethyl-1,4,5,6-tetrahydropyrrolo[3,4-c]pyrazol-3-yl)picolinamide | 134 | 1H NMR (400 MHz, DMSO-d6) d ppm 0.02-0.14 (m, 2 H) 0.38-0.53 (m, 2 H) 0.75-0.89 (m, 1 H) 0.99 (d, J = 6.32 Hz, 3 H) 1.61 (d, J = 3.54 Hz, 6 H) 2.13 (dd, J = 13.14, 6.57 Hz, 1 H) 2.30-2.39 (m, 1 H) 2.43-2.61 (m, 2 H) 2.82-3.01 (m, 2 H) 3.23 (dd, J = 18.06, 13.77 Hz, 3 H) 4.61 (s, 2 H) 7.62-7.76 (m, 1 H) 8.04-8.10 (m, 1 H) 8.13-8.20 (m, 1 H) 8.73 (d, J = 4.29 Hz, 1 H). |
| A128 | N-(5-(1-ethyl-2-methylpiperazine-4-carbonyl)-6,6-dimethyl-1,4,5,6-tetrahydropyrrolo[3,4-c]pyrazol-3-yl)picolinamide | 156 | 1H NMR (400 MHz, DMSO-d6) d ppm 0.89-1.03 (m, 6 H) 1.61 (d, J = 4.04 Hz, 6 H) 2.18-2.28 (m, 1 H) 2.28-2.37 (m, 1 H) 2.37-2.47 (m, 1 H) 2.57 (dd, J = 12.13, 8.84 Hz, 1 H) 2.65-2.78 (m, 2 H) 2.82-2.94 (m, 1 H) 3.21 (t, J = 13.39 Hz, 2 H) 4.61 (s, 2 H) 7.65-7.74 (m, 1 H) 8.02-8.11 (m, 1 H) 8.12-8.21 (m, 1 H) 8.73 (d, J = 4.55 Hz, 1 H) 10.82 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A129 | N-(6,6-dimethyl-5-{[(2S)-2,4,5,5-tetramethylpiperazin-1-yl]carbonyl}-1,4,5,6-tetrahydropyrrolo[3,4-c]pyrazol-3-yl)pyridine-2-carboxamide | 18.1 | 1H NMR (400 MHz, DMSO-d6) d ppm 1.03 (s, 3 H) 1.11-1.18 (m, 6 H) 1.66 (s, 3 H) 1.75 (s, 3 H) 2.19 (s, 3 H) 2.26-2.35 (m, 1 H) 2.63-2.72 (m, 2 H) 2.95 (d, J = 11.87 Hz, 1 H) 3.35-3.43 (m, 1 H) 4.60-4.84 (m, 2 H) 7.65-7.87 (m, 1 H) 8.05-8.18 (m, 1 H) 8.19-8.33 (m, 1 H) 8.82 (d, J = 4.80 Hz, 1 H) 10.91 (s, 1 H). |
| A130 | N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-(trifluoromethyl)picolinamide | 31.5 | 1H NMR (400 MHz, DMSO-d6) d ppm 1.24 (d, J = 6.57 Hz, 3 H) 1.25-1.36 (m, 1 H) 1.61 (d, J = 13.64 Hz, 6 H) 1.64-1.78 (m, 4 H) 1.80-1.86 (m, 1 H) 1.97 (q, 1 H) 2.17-2.27 (m, 1 H) 2.73-2.83 (m, 2 H) 2.87-2.98 (m, 1 H) 3.84 (s, 1 H) 4.49-4.67 (m, 2 H) 8.34 (d, J = 8.34 Hz, 1 H) 8.49 (d, J = 9.35 Hz, 1 H) 9.13 (s, 1 H). |
| A131 | N-(5-((2R,5S)-2-ethyl-1,5-dimethylpiperazine-4-carbonyl)-6,6-dimethyl-1,4,5,6-tetrahydropyrrolo[3,4-c]pyrazol-3-yl)picolinamide | 37.2 | 1H NMR (400 MHz, DMSO-d6) d ppm 0.72-0.95 (m, 3 H) 1.46-1.60 (m, 6 H) 1.73-1.96 (m, 2 H) 1.99-2.12 (m, 3 H) 2.31-2.54 (m, 4 H) 2.59-2.79 (m, 1 H) 2.82-3.03 (m, 2 H) 4.44-4.66 (m, 2 H) 7.46-7.73 (m, 1 H) 7.93-8.03 (m, 1 H) 8.05-8.18 (m, 1 H) 8.67 (d, J = 4.29 Hz, 1 H) 10.19-11.03 (m, 1 H) 11.65-12.26 (m, J = 36.13 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A132 | Chiral<br><br>N-(6,6-diethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide | 61.9 | 1H NMR (400 MHz, DMSO-d6) d ppm 0.52-0.69 (m, 6 H) 0.88-1.21 (m, 2 H) 1.26 (d, J = 6.82 Hz, 3 H) 1.28-1.38 (m, 1 H) 1.54-1.81 (m, 6 H) 1.99 (q, J = 8.67 Hz, 1 H) 2.19-2.34 (m, 2 H) 2.40 (dd, J = 13.39, 7.33 Hz, 1 H) 2.72-2.85 (m, 2 H) 2.93 (t, J = 7.58 Hz, 1 H) 3.84 (s, 1 H) 4.52-4.74 (m, 2 H) 7.69 (dd, J = 6.82, 5.05 Hz, 1 H) 7.98-8.11 (m, 1 H) 8.11-8.20 (m, 1 H) 8.73 (d, J = 4.29 Hz, 1 H). |
| A133 | Chiral<br><br>N-(5-{[(7S)-5,7-dimethyl-5,8-diazaspiro[3.5]non-8-yl]carbonyl}-6,6-dimethyl-1,4,5,6-tetrahydropyrrolo[3,4-c]pyrazol-3-yl)pyridine-2-carboxamide | 8.58 | 1H NMR (400 MHz, DMSO-d6) ppm 1.01 (3 H, d, J = 6.32 Hz), 1.53 (1 H, m), 1.58 (3 H, s), 1.67 (3 H, s), 1.68-1.77 (2 H, m), 1.90 (2 H, s), 2.10-2.20 (2 H, m), 2.22 (3 H, s), 2.44 (1 H, dd, J = 11.62, 3.54 Hz), 2.79 (1 H, d, J = 12.13 Hz), 3.07 (1 H, d, J = 11.87 Hz), 7.68 (1 H, ddd, J = 7.58, 4.80, 1.26 Hz), 8.04-8.12 (2 H, m), 8.72 (1 H, d, J = 4.29 Hz). |
| A134 | Chiral<br><br>N-(5-{[(2S)-2-isopropyl-4,5,5-trimethylpiperazin-1-yl]carbonyl}-6,6-dimethyl-1,4,5,6-tetrahydropyrrolo[3,4-c]pyrazol-3-yl)pyridine-2 carboxamide | 90.1 | 1H NMR (400 MHz, DMSO-d6) d ppm 0.82-0.89 (m, 9 H) 0.98 (s, 3 H) 1.22-1.31 (m, 2 H) 1.54 (s, 3 H) 1.66 (s, 3 H) 2.10 (s, 3 H) 2.24-2.35 (m, 1 H) 2.81-2.93 (m, 2 H) 3.15-3.17 (m, 1 H) 4.34-4.50 (m, 1 H) 4.66-4.77 (m, 1 H) 7.65-7.75 (m, 1 H) 8.03-8.12 (m, 1 H) 8.11-8.24 (m, 1 H) 8.67-8.81 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A135 | 5-chloro-N-(5-{[(2S)-2-isopropyl-4,5,5-trimethylpiperazin-1-yl]carbonyl}-6,6-dimethyl-1,4,5,6-tetrahydropyrrolop[3,4-c]pyrazol-3-yl)pyridine-2-carboxamide | 51.2 | 1H NMR (400 MHz, DMSO-d6) d ppm 0.79-0.89 (m, 9 H) 0.98 (s, 3 H) 1.22-1.31 (m, 1 H) 1.54 (s, 3 H) 1.66 (s, 3 H) 2.10 (s, 3 H) 2.24-2.36 (m, 1 H) 2.54-2.62 (m, 1 H) 2.81-2.94 (m, 2 H) 3.12-3.19 (m, 1 H) 4.42 (s, 1 H) 4.68 (s, 1 H) 8.17-8.18 (m, 2 H) 8.79 (s, 1 H). |
| A136 | N-(5-{[(3S,8aS)-3,8a-dimethylhexahydropyrrolo[1,2-a]pyrazin-2(1H)-yl]carbonyl}-6,6-dimethyl-1,4,5,6-tetrahydropyrrolo[3,4-c]pyrazol-3-yl)pyridine-2-carboxamide | 57.6 | 1H NMR (400 MHz, DMSO-d6) d ppm 0.86 (s, 3 H) 1.07 (d, J = 6.29 Hz, 3 H) 1.19-1.29 (m, 2 H) 1.42-1.75 (m, 8 H) 2.36-2.45 (m, 1 H) 2.54-2.62 (m, 1 H) 2.63-2.80 (m, 2 H) 3.10 (s, 2 H) 3.78-3.87 (m, 1 H) 4.63-4.75 (m, 1 H) 7.60-7.76 (m, 1 H) 7.98-8.23 (m, 2 H) 8.71 (s, 1 H). |
| A137 | N-(5-{[(2S,5R)-4-(3-methoxypropyl)-2,5-dimethylpiperazin-1-yl]carbonyl}-6,6-dimethyl-1,4,5,6-tetrahydropyrrola[3,4-c]pyrazol-3-yl)pyridine-2-carboxamide. | 19.5 | 1H NMR (300 MHz, DMSO-d6) d 0.95-1.00 (m, 4 H) 1.58 (s, 3 H) 1.59-1.66 (m, 1 H) 1.67 (s, 3 H) 1.90 (s, 3 H) 1.97-2.01 (m, 1 H) 2.15-2.30 (m, 1 H) 2.40-2.42 (m, 2 H) 2.67-2.71 (m, 1 H) 2.76-2.81 (m, 1 H) 3.01-3.14 (m, 2 H) 3.22 (s, 3 H) 3.32-3.36 (m, 3 H) 4.65 (s, 2 H) 7.68-7.72 (m, 1 H) 8.05-8.10 (m, 1 H) 8.13-8.20 (m, 1 H) 8.73-8.73 (m, 1 H) 10.9 (bs, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A138 | Chiral<br><br>N-(5-{[(3S,8aS)-3,8a-dimethylhexahydropyrrolo[1,2-a]pyrazin-2(1H)-yl]carbonyl}-6,6-dimethyl-1,4,5,6-tetrahydropyrrolo[3,4-c]pyrazol-3-yl)-5-fluoropyridine-2-carboxamide | 29.3 | 1H NMR (400 MHz, MeOD) d ppm 1.18 (d, J = 6.04, 3 H) 1.26 (s, 3 H) 1.69 (s, 3H), 1.75-1.86 (m, 4H) 1.95-2.10 (m, 3 H) 2.80-2.97 (m, 2H) 3.10-3.19 (m, 1H) 3.21-3.28 (m, 1H) 3.35-3.44 (m, 1H) 3.52-3.55 (m, 1H) 3.77-3.93 (m, 1 H) 4.64-4.68 (m, 1H) 4.88-4.97 (m, 1 H) 7.74-7.91 (m, 1 H) 8.25-8.28 (m, 1 H) 8.61 (d, J = 2.77 Hz, 1 H). |
| A139 | Chiral<br><br>N-(5-{[(3S,8aS)-3-ethyl-8a-methylhexahydropyrrolo[1,2-a]pyrazin-2(1H)-yl]carbonyl}-6,6-dimethyl-1,4,5,6-tetrahydropyrrolo[3,4-c]pyrazol-3-yl)-5-fluoropyridine-2-carboxamide | 75.2 | 1H NMR (400 MHz, MeOD) d ppm 0.93 (t, J = 7.43 Hz, 3 H) 1.12 (s, 3 H) 1.48-1.58 (m, 1 H) 1.68 (s, 3 H) 1.69-1.77 (m, 3 H) 1.80 (s, 3 H) 1.82-1.92 (m, 2 H) 2.65-2.77 (m, 2 H) 3.00-3.12 (m, 2 H) 3.22-3.29 (m, 1 H) 3.34-3.45 (m, 1 H) 3.77-3.88 (m, 1 H) 4.53-4.66 (m, 2 H) 7.74-7.91 (m, 1 H) 8.27 (dd, J = 8.81, 4.53 Hz, 1 H) 8.61 (d, J = 2.77 Hz, 1 H). |
| A140 | Chiral<br><br>5-cyclopropyl-N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)isoxazole-3-carboxamide | 26.8 | $^1$H NMR (400 MHz, MeOD) d ppm 0.95-1.05 (m, 2H) 1.10-1.22 (m, 5H) 1.38-1.43 (m, 3H), 1.73 (s, 3H) 1.78 (s, 3 H) 2.16-2.26 (m, 1 H) 2.67 (s, 3 H) 2.70-2.81 (m, 1 H) 2.90-3.10 (m, 3H) 3.40-3.60 (m, 2 H) 4.75-4.90 (m, 2H) 6.47 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A141 | N-(5-((2R,5S)-1-(3-cyanopropyl)-2,5-dimethylpiperazine-4-carbonyl)-6,6-dimethyl-1,4,5,6-tetrahydropyrrolo[3,4-c]pyrazol-3-yl)picolinamide | 23.6 | $^1$H NMR (300 MHz, DMSO-$d_6$) δ ppm 0.89-1.09 (m, 6 H) 1.50-1.83 (m, 9 H) 1.89-2.02 (m, J = 9.42 Hz, 1 H) 2.16-2.28 (m, 1 H) 2.44 (d, J = 6.78 Hz, 3 H) 2.75 (m, 2 H) 3.10 (m, 2 H) 4.66 (s, 2 H) 7.63-7.75 (m, 1 H) 8.02-8.12 (m, 1 H) 8.13-8.23 (m, 1 H) 8.73 (d, J = 4.14 Hz, 1 H) 10.32-11.39 (m, 1 H) 12.28 (d, J = 146.37 Hz, 1 H). |
| A142 | N-(5-((2R,5S)-1-(3-fluoropropyl)-2,5-dimethylpiperazine-4-carbonyl)-6,6-dimethyl-1,4,5,6-tetrahydropyrrolo[3,4-c]pyrazol-3-yl)picolinamide | 43.4 | $^1$H NMR (300 MHz, DMSO-$d_6$) δ ppm 1.04 (m, 6 H) 1.72 (m, 8 H) 1.93-2.07 (m, 1 H) 2.27 (d, J = 5.09 Hz, 1 H) 2.44 (s, 2 H) 2.78 (m, 2 H) 3.11 (m, 2 H) 4.36-4.48 (m, 1 H) 4.51-4.61 (m, 1 H) 4.68 (m, 2 H) 7.70 (s, 1 H) 8.12 (d, J = 25.05 Hz, 2 H) 8.73 (s, 1 H) 10.87 (d, J = 267.50 Hz, 1 H) 12.29 (d, J = 144.86 Hz, 1 H) |
| A143 | N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide | 1.9 | $^1$H NMR (300 MHz, CHLOROFORM-d) δ ppm 1.01 (m, 3 H) 1.12 (d, J = 6.03 Hz, 3 H) 1.25 (m, 3 H) 1.65 (m, 2 H) 1.73 (s, 3 H) 1.81 (s, 3 H) 2.04 (m, 2 H) 2.17 (s, 1 H) 2.52 (m, 2 H) 2.67-2.80 (m, 1 H) 2.81-2.93 (m, 1 H) 3.12 (dd, J = 11.40, 1.79 Hz, 1 H) 3.39 (m, 3 H) 3.97 (dd, J = 10.93, 3.01 Hz, 2 H) 4.73 (m, 2 H) 7.52 (dd, J = 6.50, 4.80 Hz, 1 H) 7.88-7.98 (m, 1 H) 8.26 (d, J = 7.72 Hz, 1 H) 8.62 (d, J = 4.14 Hz, 1 H) 10.38 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A144 | 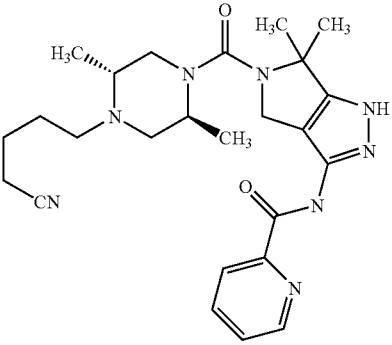 N-(5-((2R,5S)-1-(4-cyanobutyl)-2,5-dimethylpiperazine-4-carbonyl)-6,6-dimethyl-1,4,5,6-tetrahydropyrrolo[3,4-c]pyrazol-3-yl)picolinamide | 38.3 | $^1$H NMR (300 MHz, DMSO-d$_6$) δ ppm 0.99 (m, 6 H) 1.59 (m, 8 H) 1.88-2.05 (m, 1 H) 2.13-2.29 (m, 1 H) 2.43 (d, J = 6.59 Hz, 2 H) 2.65 (d, J = 5.84 Hz, 1 H) 2.79 (d, J = 9.61 Hz, 1 H) 3.09 (m, 3 H) 3.35 (m, 3 H) 4.65 (s, 2 H) 7.70 (s, 1 H) 8.12 (m, 2 H) 8.73 (d, 1 H) 10.87 (d, J = 266.37 Hz, 1 H) 12.29 (d, J = 147.31 Hz, 1 H). |
| A145 | 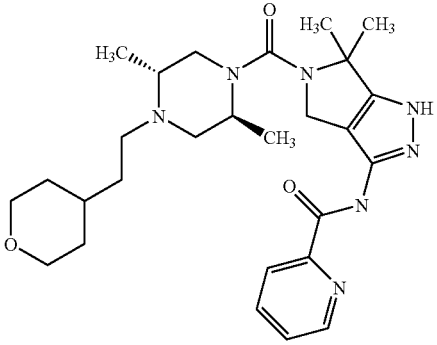 N-(5-((2R,5S)-2,5-dimethyl-1-(2(tetradhydro-2H-pyran-4-yl)ethyl)piperazine-4-carbonyl)-6,6-dimethyl-1,4,5,6-tetrahydropyrrolo[3,4-c]pyrazol-3-yl)picolinamide | 17.6 | $^1$H NMR (300 MHz, DMSO-d$_6$) δ ppm 0.91-1.05 (m, 6 H) 1.05-1.26 (m, 2 H) 1.35 (t, J = 7.91 Hz, 2 H) 1.41-1.72 (m, 7 H) 1.99 (d, J = 8.10 Hz, 1 H) 2.17-2.31 (m, 2 H) 2.41 (d, J = 6.40 Hz, 2 H) 2.61-2.83 (m, 3 H) 2.99-3.13 (m, 2 H) 3.19-3.29 (m, 2 H) 3.74-3.86 (m, 2 H) 4.65 (s, 2 H) 7.66-7.70 (m, 1 H) 8.08 (m, 1 H) 8.18 (m, 1 H) 8.73 (s, 1 H) 10.87 (d, J = 269.38 Hz, 1 H) 12.28 (d, J = 149.76 Hz, 1 H). |
| A146 | 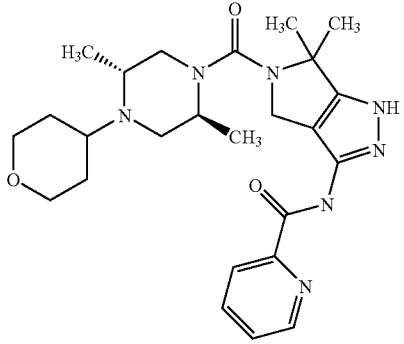 N-(5-((2R,5S)-2,5-dimethyl-1-(tetrahydro-2H-pyran-4-yl)piperazine-4-carbonyl)-6,6-dimethyl-1,4,5,6-tetrahydropyrrolo[3,4-c]pyrazol-3-yl)picolinamide | 1.7 | $^1$H NMR (300 MHz, DMSO-d$_6$) δ ppm 1.07 (d, J = 5.84 Hz, 3 H) 1.32 (d, J = 5.84 Hz, 3 H) 1.62 (s, 3 H) 1.65-1.81 (m, 5 H) 1.81-1.99 (m, 2 H) 2.69-2.99 (m, 2 H) 3.30 (s, 1 H) 3.36-3.55 (m, 3 H) 3.80 (m, 1 H) 3.97 (d, J = 9.04 Hz, 2 H) 4.72 (d, J = 1.88 Hz, 2 H) 7.70 (m, 1 H) 8.05-8.18 (m, 2 H) 8.73 (d, J = 0.75 Hz, 1 H) 9.47 (s, 1 H) 10.87 (s, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A147 | N-(5-{[(2S,5R)-2,5-dimethyl-4-(tetrahydrofuran-3-ylmethyl)piperazin-1-yl]carbonyl}-6,6-dimethyl-1,4,5,6-tetrahydropyrrolo[3,4-c]pyrazol-3-yl)pyridine-2-carboxamide | <10 | 1H NMR (300 MHz, DMSO-$d_6$) δ 1.06 (d, J = 5.84 Hz, 3 H) 1.23-1.28 (m, 1 H) 1.32 (d, J = 4.33 Hz, 3 H) 1.62 (s, 3 H) 1.69 (s, 3 H) 2.04-2.19 (m, 1 H) 2.59-2.81 (m, 1 H) 2.59-2.81 (m, 1 H) 2.83-2.98 (m, 1 H) 3.05-3.20 (m, 1 H) 3.21-3.46 (m, 4 H) 3.21-3.46 (m, 1 H) 3.54-3.71 (m, 2 H) 3.72-3.81 (m, 1 H) 3.81-3.91 (m, 1 H) 4.63-4.80 (m, 2 H) 7.65-7.74 (m, 1 H) 7.99-8.16 (m, 1 H) 8.09 (d, J = 0.94 Hz, 1 H) 8.74 (d, J = 4.52 Hz, 1 H) 9.56 (br. s., 1 H) 10.86 (s, 1 H). |
| A148 | N-(5-{[(2S,5R)-2,5-dimethyl-4-(1,3-oxazol-4-ylmethyl)piperazin-1-yl]carbonyl}-6,6-dimethyl-1,4,5,6-tetrahydropyrrolo[3,4-c]pyrazol-3-yl)pyridine-2-carboxamide | 48.3 | $^1$H NMR (300 MHz, CHLOROFORM-d) δ ppm 1.06 (d, J = 6.03 Hz, 3 H), 1.20 (d, J = 5.84 Hz, 3 H), 1.73 (s, 3 H), 1.81 (s, 3 H), 2.15-2.32 (m, 1 H), 2.65-2.80 (m, 2 H), 2.80-2.91 (m, 1 H), 3.00-3.14 (m, 1 H), 3.24-3.41 (m, 1 H), 3.59-3.91 (m, 2 H), 4.57-4.83 (m, 2 H), 7.47-7.59 (m, 1 H), 7.63 (s, 1 H), 7.87-7.99 (m, 2 H), 8.27 (d, J = 7.91 Hz, 1 H), 8.63 (d, J = 4.14 Hz, 1 H), 10.36 (s, 1 H). |
| A149 | N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide | <10 | 1H NMR (300 MHz, DMSO-$d_6$) δ 0.95-1.07 (m, 6 H) 1.33-1.54 (m, 2 H) 1.33-1.54 (m, 1 H) 1.54-1.63 (m, 5 H) 1.67 (br. s., 4 H) 2.11-2.22 (m, 1 H) 2.68-2.91 (m, 1 H) 2.68-2.91 (m, 2 H) 3.06-3.20 (m, 3 H) 3.06-3.20 (m, 1 H) 3.20-3.28 (m, 1 H) 3.88 (d, J = 9.04 Hz, 2 H) 4.02-4.18 (m, 0 H) 4.56-4.71 (m, 2 H) 7.93-8.04 (m, 1 H) 8.19-8.29 (m, 1 H) 8.69-8.79 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A150 | N-(5-((2R,5S)-2-(2-hydroxyethyl)-1,5-dimethylpiperazine-4-carbonyl)-6,6-dimethyl-1,4,5,6-tetrahydropyrroio[3,4-c]pyrazol-3-yl)picolinamide (Isomer A) | 42.0 | 1H NMR (300 MHz, DMSO-$d_6$) δ 0.96 (d, J = 6.03 Hz, 3 H) 1.37-1.52 (m, 1 H) 1.59 (s, 3 H) 1.63-1.77 (m, 1 H) 1.67 (s, 3 H) 1.86-1.92 (m, 2 H) 1.92-1.99 (m, 1 H) 2.11-2.23 (m, 4 H) 2.66-2.79 (m, 1 H) 2.98-3.15 (m, 1 H) 2.98-3.15 (m, 1 H) 3.38-3.50 (m, 2 H) 3.38-3.50 (m, 1 H) 4.57-4.73 (m, 2 H) 7.65-7.76 (m, 1 H) 8.04-8.13 (m, 1 H) 8.13-8.22 (m, 1 H) 8.73 (d, J = 4.52 Hz, 1 H) 10.86 (br. s., 1 H). |
| A151 | N-(5-((2S,5S)-2-(2-hydroxyethyl)-1,5-dimethylpiperazine-4-carbonyl)-6,6-dimethyl-1,4,5,6-tetrahydropyrroio[3,4-c]pyrazol-3-yl)picolinamide (Isomer B) | 152 | 1H NMR (300 MHz, DMSO-$d_6$) δ 1.19 (d, J = 6.59 Hz, 3 H) 1.42-1.55 (m, 1 H) 1.61 (d, J = 10.93 Hz, 6 H) 1.70-1.82 (m, 1 H) 1.87-1.96 (m, 2 H) 1.99-2.11 (m, 1 H) 2.15 (s, 3 H) 2.20-2.32 (m, 1 H) 2.77-2.90 (m, 1 H) 3.06-3.14 (m, 1 H) 3.24-3.40 (m, 1 H) 3.40-3.55 (m, 1 H) 3.40-3.55 (m, 1 H) 3.58-3.72 (m, 1 H) 4.51-4.67 (m, 2 H) 7.65-7.74 (m, 1 H) 8.03-8.12 (m, 1 H) 8.12-8.19 (m, 1 H) 8.73 (d, J = 4.71 Hz, 1 H) 10.82 (br. s., 1 H). |
| A152 | N-(5'-{[(2S,5R)-2,5-dimethyl-4-(tetrahydro-2H-pyran-4-ylmethyl)piperazin-1-yl]carbonyl}-4',5'-dihydro-1'H-spiro[cyclopropane-1,6'-pyrrolo[3,4-c]pyrazol]-3'-yl)pyridine-2-carboxamide | 76.2 | 1H NMR (300 MHz, DMSO-$d_6$) δ 0.94 (d, J = 5.84 Hz, 6 H) 0.98-1.08 (m, 5 H) 1.08-1.23 (m, 2 H) 1.49-1.59 (m, 1 H) 1.59-1.76 (m, 3 H ) 1.92-2.04 (m, 2 H) 2.17-2.31 (m, 1 H) 2.71-2.86 (m, 1 H) 3.08-3.19 (m, 1 H) 3.19-3.29 (m, 3 H) 3.76-3.92 (m, 2 H) 4.69-4.88 (m, 2 H) 7.64-7.78 (m, 1 H) 8.03-8.12 (m, 1 H) 8.12-8.23 (m, 1 H) 8.73 (d, J = 4.14 Hz, 1 H) 11.00 (br. s., 1 H) 12.01 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A153 | 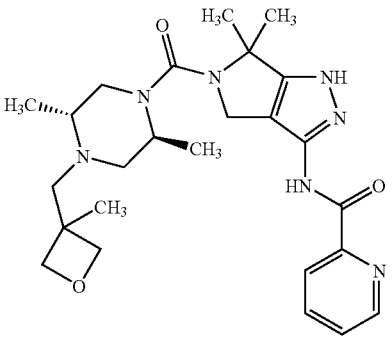 N-[5-({(2S,5R)-2,5-dimethyl-4-[(3-methyloxetan-3-yl)methyl]piperazin-1-yl}carbonyl)-6,6-dimethyl-1,4,5,6-tetrahydropyrrolo[3,4-c]pyrazol-3-yl]pyridine-2-carboxamide | 37 | 1H NMR (300 MHz, CHLOROFORM-d) δ 1.04 (d, J = 6.22 Hz, 3 H) 1.14 (d, J = 6.22 Hz, 3 H) 1.39 (s, 3 H) 1.72 (s, 3 H) 1.81 (s, 3 H) 1.92-2.04 (m, 1 H) 2.41-2.51 (m, 1 H) 2.52-2.65 (m, 1 H) 2.52-2.65 (m, 1 H) 2.68-2.76 (m, 1 H) 2.76-2.85 (m, 1 H) 3.13-3.24 (m, 1 H) 3.41-3.53 (m, 1 H) 4.28-4.38 (m, 2 H) 4.48 (d, J = 5.65 Hz, 1 H) 4.55 (d, J = 5.65 Hz, 1 H) 4.65-4.75 (m, 2 H) 7.49-7.58 (m, 1 H) 7.89-8.00 (m, 1 H) 8.28 (d, J = 7.91 Hz, 1 H) 8.64 (d, J = 4.52 Hz, 1 H) 10.33 (s, 1 H). |
| A154 | 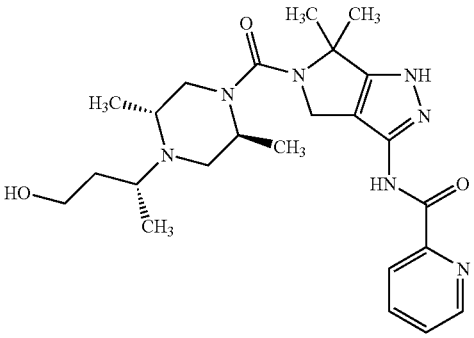 N-[5-({(2S,5R)-4-[(1R)-3-hydroxy-1-methylpropyl]-2,5-dimethylpiperazin-1-yl}carbonyl)-6,6-dimethyl-1,4,5,6-tetrahydropyrrolo[3,4-c]pyrazol-3-yl]pyridine-2-carboxamide | 25.1 | 1H NMR (400 MHz, MeOD) δ 1.00-1.02 (m, 6 H) 1.08-1.18 (m, 3 H) 1.50-1.60 (m, 2 H) 1.66 (s, 3 H) 1.69 (s, 3 H) 2.07-2.10 (m, 1 H) 2.41-2.49 (m, 1 H) 2.51-2.52 (m, 2 H) 2.72-2.82 (m, 2 H) 3.05-3.11 (m, 1 H) 3.12-3.22 (m, 1 H) 3.70-3.76 (m, 1 H) 4.71-4.72 (m, 2 H) 7.51-7.54 (m, 1 H) 7.91 7.95 (m, 1 H) 8.10-8.12 (m, 1 H) 8.60-8.61 (m, 1 H). |
| A155 | 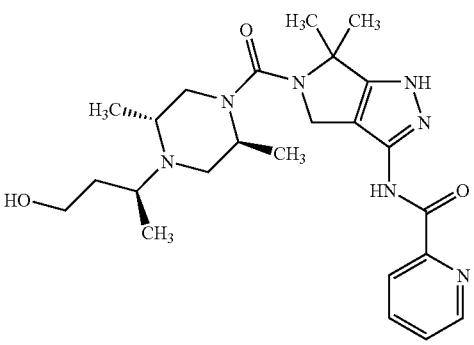 N-[5-({(2S,5R)-4-[(1S)-3-hydroxy-1-methylpropyl]-2,5-dimethylpiperazin-1-yl}carbonyl)-6,6-dimethyl-1,4,5,6-tetrahydropyrrolo[3,4-c]pyrazol-3-yl]pyridine-2-carboxamide | 43.3 | 1H NMR (400 MHz, MeOD) δ 0.99-1.01 (m, 6 H) 1.15-1.17 (m, 3 H) 1.44-1.56 (m, 2 H) 1.58 (s, 3 H) 1.60 (s, 3 H) 1.91-1.99 (m, 1 H) 2.23-2.29 (m, 1 H) 2.43-2.50 (m, 2 H) 2.89-2.96 (m, 2 H) 3.04-3.10 (m, 2 H) 3.69-3.77 (m, 1 H) 4.68-4.84 (m, 2 H) 7.50-7.53 (m, 1 H) 7.90-7.94 (m, 1 H) 8.10-8.11 (m, 1 H) 8.59-8.60 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A156 | N-[5-({(2S,5R)-4-[2-(2-hydroxyethoxy)ethyl]-2,5-dimethylpiperazin-1-yl}carbonyl)-6,6-dimethyl-1,4,5,6-tetrahydropyrrolo[3,4-c]pyrazol-3-yl]pyridme-2-carboxamide | 108 | 1H NMR (400 MHz, MeOD) δ 0.98-1.01 (m, 6 H) 1.60 (s, 3 H) 1.69 (s, 3 H) 2.08-2.13 (m, 1 H) 2.37-2.43 (m, 1 H) 2.47-2.53 (m, 2 H) 2.89-2.97 (m, 2 H) 3.04-3.14 (m, 2 H) 3.44-3.47 (m, 2 H) 3.50-3.61 (m, 4 H) 4.68-4.76 (m, 2 H) 7.51-7.54 (m, 1 H) 7.91-7.95 (m, 1 H) 8.10-8.12 (m, 1 H) 8.59-8.60 (m, 1 H). |
| A157 | N-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyridine-2-carboxamide | 38.8 | $^1$H NMR (300 MHz, DMSO-d6) δ ppm 0.88-1.07 (m, 6 H), 1.58 (s, 3 H), 1.67 (s, 3 H), 2.10 (t, J = 10.0 Hz, 1 H), 2.32-2.48 (m, 3 H), 2.75-2.91 (m, 2 H), 3.06 (dd, J = 9.2, 1.5 Hz, 2 H), 3.25 (s, 3 H), 3.39-3.46 (m, 2 H), 4.66 (s, 2 H), 7.64-7.77 (m, 1 H), 8.03-8.13 (m, 1 H), 8.14-8.24 (m, 1 H), 8.69-8.80 (m, 1 H), 10.86 (br. s., 1 H), 12.18 (br. s., 1 H) |
| A158 | N-[5-({(2S,5R)-4-[(2S)-3-hydroxy-2-methylpropyl]-2,5-dimethylpiperazin-1-yl}carbonyl)-6,6-dimethyl-1,4,5,6-tetrahydropyrrolo[3,4-c]pyrazol-3-yl]pyridine-2-carboxamide | 50.4 | $^1$H NMR (400 MHz, MeOD) δ ppm 0.79 (d, J = 6.4 HZ, 3H), 1.03 (d, J = 6.0 Hz, 3H), 1.07 (d, J = 6.0 Hz, 3H), 1.60 (s, 3H), 1.70 (s, 3H), 1.96-2.07 (m, 2H), 2.15-2.19 (m, 1H), 2.49-2.56 (m, 2H), 2.76-2.83 (m, 2H), 3.07-3.14 (m, 3H), 3.44-3.46 (m, 2H), 4.73-4.79 (m, 2H), 7.51-7.54 (m, 1H), 7.91-7.95 (m, 1 H), 8.09-8.11 (m, 1H), 8.59-8.61 (m, 1H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A159 | 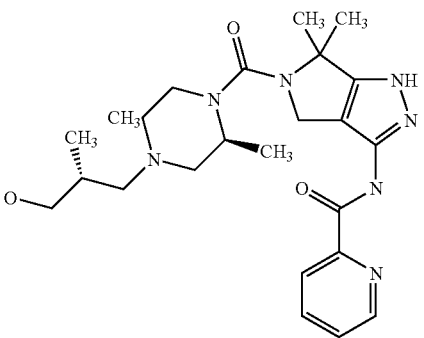 N-[5-({(2S,5R)-4-[(2R)-3-hydroxy-2-methylpropyl]-2,5-dimethylpiperazin-1-yl}carbonyl)-6,6-dimethyl-1,4,5,6-tetrahydropyrrolo[3,4-c]pyrazol-3-yl]pyridine-2-carboxamide. | 49.6 | $^1$H NMR (400 MHz, MeOD) δ ppm 0.76 (d, J = 6.8 HZ, 3H), 1.00-1.02 (m, 6H), 1.60 (m, 3H), 1.69 (s, 3H), 1.88-1.97 (m, 2H), 2.02-2.07 (m, 1H), 2.44-2.49 (m, 2H), 2.69-2.72 (m, 1H), 2.97-3.00 (m, 1H), 3.08-3.10 (m, 2H), 3.40-3.48 (m, 2H), 4.72-4.78 (m, 2H), 7.50-7.53 (m, 1H), 7.91-7.95 (m, 1H), 8.10-8.12 (m, 1H), 8.59-8.60 (m, 1H). |
| A160 | 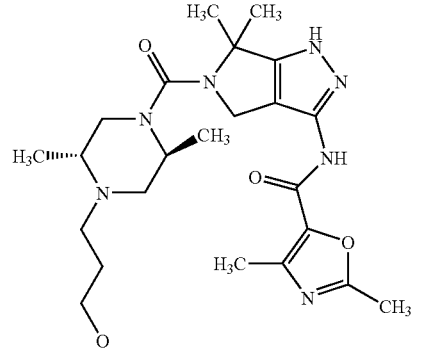 N-(5-{[(2S,5R)-4-(3-hydroxypropyl)-2,5-dimethylpiperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide | 24.9 | 1H NMR (400 MHz, MeOD) δ ppm 1.07-1.16 (m, 6 H) 1.70 (s, 3 H) 1.72-1.80 (m, 5 H) 2.47 (s, 3 H) 2.54 (s, 3 H) 2.60 (d, J = 6.55 Hz, 2 H) 2.89-3.00 (m, 2 H) 3.13-3.37 (m, 2 H) 3.48-3.52 (m, 1 H) 3.64 (t, J = 6.17 Hz, 2 H) 4.59-4.62 (m, 2 H) |
| A161 | 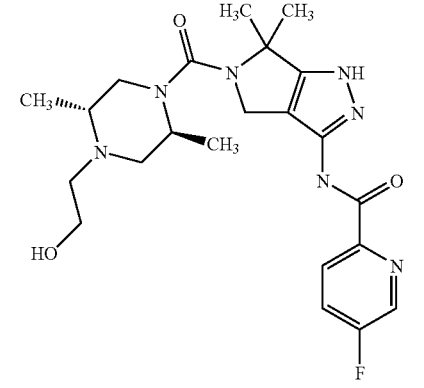 5-fluoro-N-(5-((2R,5S)-1-(2-hydroxyethyl)-2,5-dimethylpiperazine-4-carbonyl)-6,6-dimethyl-1,4,5,6-tetrahydropyrrolo[3,4-c]pyrazol-3-yl)picolinamide | 38.8 | 1H NMR (400 MHz, MeOD) δ ppm 1.04-1.15 (m, 6 H) 1.70 (s, 3 H) 1.79 (s, 3 H) 2.20-2.30 (1 H) 2.41-2.53 (m, 1 H) 2.54-2.75 (m, 2 H) 2.87-3.05 (m, 1 H) 3.10-3.28 (m, 3 H) 3.64-3.76 (m, 2 H) 4.74-4.85 (m, 2 H) 7.75-7.92 (m, 1H) 8.27-8.29 (m, 1 H) 8.61 (d, J = 2.77 Hz, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| A162 | 5-fluoro-N-(5-{[(2S,5R)-4-(3-hydroxypropyl)-2,5-dimethylpiperazin-1-yl]carbonyl}-6,6-dimethyl-1,4,5,6-tetrahydropyrrolo[3,4-c]pyrazol-3-yl)pyridine-2-carboxamide | 21.7 | 1H NMR (400 MHz, MeOD) δ ppm 1.11-1.13 (m, 6 H) 1.65-1.83 (m, 8 H) 2.11-2.24 (m, 1 H) 2.43-2.52 (m, 1 H) 2.56-2.69 (m, 2 H) 2.90-3.00 (m, 1 H) 3.10-3.30 (m, 3 H) 3.63 (t, J = 6.04 Hz, 2 H) 4.81 (s, 2 H) 7.74-7.89 (m, 1 H) 8.25-8.30 (m, 1 H) 8.57-8.63 (m, 1 H) |
| A163 | 5-fluoro-N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyridine-2-carbaxamide | 24.5 | 1H NMR (400 MHz, MeOD) δ ppm 1.06-1.13 (m, 6 H) 1.68-1.84 (m, 8 H) 2.10-2.19 (m, 1 H) 2.37-2.48 (m, 1 H) 2.54-2.65 (m, 2 H) 2.75-2.93 (m, 2H) 3.11-3.26 (m, 2 H) 3.34 (s, 3H) 3.40-3.50 (m, 2 H) 4.73-4.85 (m, 2 H) 7.74-7.91 (m, 1 H) 8.25-8.33 (m, 1 H) 8.60-8.62 (m, 1 H) |
| A164 | 5-fluoro-N-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyridine-2-carboxamide | 56.9 | 1H NMR (400 MHz, MeOD) δ ppm 1.07-1.13 (m, 6 H) 1.71 (s, 3 H) 1.80 (s, 3 H) 2.19-2.27 (m, 1 H) 2.48-2.67 (m, 3 H) 2.95-3.05 (m, 2 H) 3.13-3.25 (m, 2 H) 3.37 (s, 3H) 3.53-3.61 (m, 2 H) 4.75-4.86 (m, 2 H) 7.76-7.89 (m, 1 H) 8.27-8.32 (m, 1 H) 8.60-8.64 (m, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| B1 | Pyridine-2-carboxylic acid [5-(1-cyclobutyl-4-fluoro-piperidine-4-carbonyl)-6,6-dimethyl-1,4,5,6-tetrahydro-pyrrolo[3,4-c]pyrazol-3-yl]-amide | 75.3 | 1H NMR (400 MHz, DMSO-d6, ppm) δ 1.68 (s, 6H), 1.53-3.03 (br m, 12 H), 2.57-3.10 (br s, 3H), 4.96 (s, 2H), 7.67-7.71 (m, 1H), 8.08 (dd, J = 7.56, 7.80 Hz, 1H), 8.16 (d, J = 7.80 Hz, 1H), 8.74 (d, J = 4.28 Hz, 1H), 10.42 (s, 0.5 H), 11.33 (s, 0.5H), 12.06 (s, 0.5H), 12.59 (s, 0.5H). |
| B2 | Pyridine-2-carboxylic acid {5-[4-fluoro-1-(tetrahydro-pyran-4-yl)-piperidine-4-carbonyl]-6,6-dimethyl-1,4,5,6-tetrahydro-pyrrolo[3,4-c]pyrazol-3-yl}-amide | 89.8 | 1H NMR (400 MHz, DMSO-d6, ppm) δ 1.41-1.51 (m, 2H), 1.65-1.71 (m, 2H), 1.68 (s, 6H), 1.93-2.02 (m, 3H), 2.07-2.14 (m, 2H), 2.42-2.54 (m, 2H), 2.83-2.86 (m, 2H), 3.27 (dd, J = 10.56, 10.56 Hz, 2H), 3.88 (dd, J = 3.27, 11.04 Hz, 2H), 4.96 (d, J = 4.28 Hz, 2H), 7.70 (ddd, J = 1.26, 4.80, 7.56 Hz, 1H), 8.08 (ddd, J = 1.76, 7.56, 7.56 Hz, 1H), 8.16 (d, J = 7.56 Hz, 1H), 8.73 (d, J = 4.03 Hz, 1H) (one pyrazole N—H and one amide N—H are missing due to deuterium exchange); 19F NMR (376 Hz, DMSO-d6, ppm) δ −16 |
| B3 | 3,4-dichloro-N-{5-[(4-fluoro-1-methylpiperidin-4-yl)carbonyl]-66-dimethyl-1456-tetrahydropyrrolo[34-c]pyrazol-3-yl}benzamide | 67.4 | 1H NMR (400 MHz, MeOD) d ppm 8.12-8.17 (m, 1 H) 7.86-7.92 (m,, 1 H) 7.69-7.77 (m, 1 H) 5.07 (d, J = 4.80 Hz, 2 H) 4.61-4.66 (m, 2 H) 3.55-3.66 (m, 2 H) 2.98 (s, 3 H) 2.34-2.59 (m, 2 H) 1.80-1.84 (m, 5 H) 1.78 (s, 3 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| B4 | 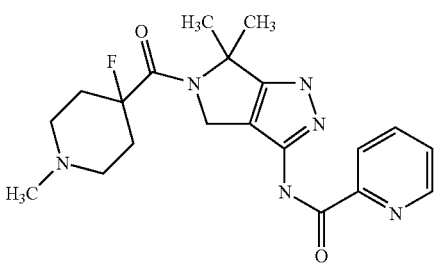<br>N-{5-[(4-fluoro-1-methylpiperidin-4-yl)carbonyl]-6,6-dimethyl-1,4,5,6-tetrahydropyrrolo[3,4-c]pyrazol-3-yl}pyridine-2-carboxamide | NT | 1H NMR (300 MHz, DMSO-d6) d ppm 1.68 (s, 6 H) 1.91-2.08 (m, 1 H) 1.91-2.08 (m, 2 H) 2.10-2.17 (m, 3 H) 2.20 (s, 3 H) 2.62-2.68 (m, 1 H) 2.68-2.75 (m, 1 H) 4.89-5.00 (m, 2 H) 7.66-7.72 (m, 1 H) 8.04-8.11 (m, 1 H) 8.04-8.11 (m, 1 H) 8.14-8.19 (m, 1 H) 8.70-8.75 (m, 1 H) 10.85 (br. s., 1 H) |
| C1 | Chiral<br>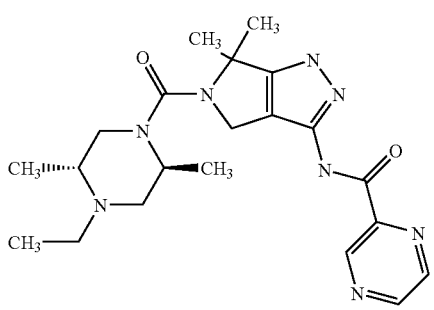<br>N-(5-{[(2S,5R)-4-ethyl-2,5-dimethylpiperazin-1-yl]carbonyl}-6,6-dimethyl-1,4,5,6-tetrahydropyrrolo[3,4-c]pyrazol-3-yl)pyrazine-2-carboxamide | 28.6 | 1H NMR (400 MHz, DMSO-d6) ppm 0.95-1.00 (11 H, m), 1.59 (3 H, s), 1.68 (3 H, s), 1.88 (3 H, s), 1.99 (1 H, dd, J = 11.08, 9.32 Hz), 2.27-2.37 (2 H, m), 2.37-2.44 (2 H, m), 2.66-2.78 (2 H, m), 3.01-3.10 (2 H, m), 4.65 (2 H, d, J = 3.53 Hz), 8.80-8.83 (1 H, m), 8.94 (1 H, d, J = 2.27 Hz), 9.31 (1 H, d, J = 1.26 Hz). |
| C2 | 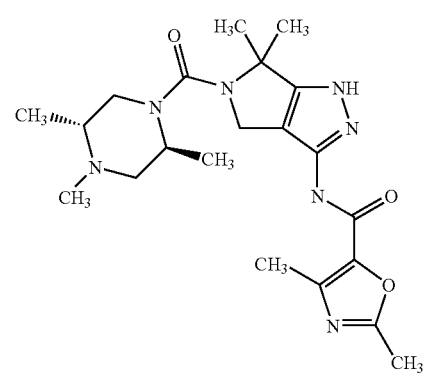<br>N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-2,4-dimethyl-1,3-oxazole-5-carboxamide | 50.3 | 1H NMR (400 MHz, CHLOROFORM-d) δ ppm 1.08-1.20 (m, 6 H), 1.75 (s, 3 H) 1.84 (s, 3 H) 2.10-2.20 (m, 1 H) 2.30-2.40 (m, 4 H) 2.55 (s, 3 H) 2.56 (s, 3H) 2.64-2.74 (m, 1 H) 2.78-2.86 (m,, 1 H) 3.00-3.10 (m, 1 H) 3.25-3.35 (m, 1H) 4.68 (d, J = 9.60 Hz, 1 H) 4.83 (d, J = 9.60 Hz, 1H) 8.55 (s, 1H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| C3 | 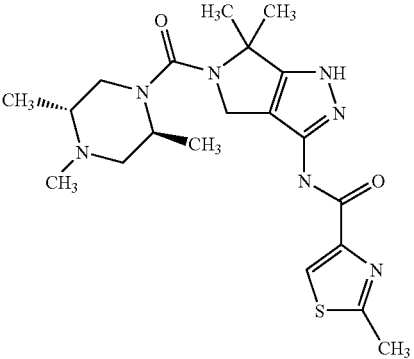 N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-2-methyl-1,3-thiazole-4-carboxamide | 35.1 | 1H NMR (400 MHz, CHLOROFORM-d) δ ppm 1.00-1.11 (m, 6 H) 1.67 (s, 3 H), 1.74 (s, 3 H) 2.10-2.25 (m, 2 H) 2.31 (s, 3 H) 2.65-2.72 (m, 1 H) 2.70 (s, 3H) 2.75-2.80 (m, 1 H) 2.92-3.00 (m, 1 H) 3.20-3.35 (m, 1 H) 4.62 (d, J = 12.80 Hz, 1 H) 4.72 (d, J = 12.80 Hz, 1 H) 8.03 (s, 1 H) 9.58 (brs, 1 H) |
| C4 | 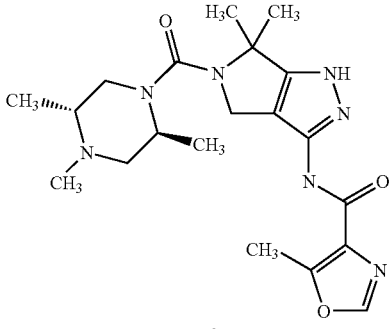 N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-5-methyl-1,3-oxazole-4-carboxamide | 45.1 | 1H NMR (400 MHz, CHLOROFORM-d) δ ppm 0.98-1.11 (m, 6 H) 1.65 (s, 3 H)1.74 (s, 3 H) 1.94-2.02 (m, 1 H) 2.10-2.30 (m, 1H) 2.22 (s, 3H) 2.50-2.60 (m, 1 H) 2.62-2.73 (m, 4 H) 2.80-2.95 (m, 1 H) 3.12-3.20 (m, 1 H) 4.53 (d, J = 13.60 Hz, 1 H) 4.67 (d, J = 13.60 Hz, 1 H) 7.72 (s, 1 H) 9.35 (brs, 1 H). |
| C5 | 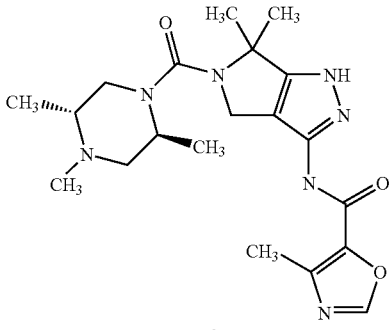 N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-4-methyl-1,3-oxazole-5-carboxamide | 46.5 | 1H NMR (400 MHz, CHLOROFORM-d) δ ppm 0.98-1.02 (m, 6 H) 1.66 (s, 3 H) 1.74 (s, 3 H) 2.00-2.06 (m, 1 H) 2.18-2.23 (m, 1 H) 2.23 (s, 3H) 2.52-2.60 (m, 4 H) 2.69-2.73 (m, 1 H) 2.91-2.95 (m, 1 H) 3.17-3.23 (m, 1 H) 4.60 (d, J = 13.60 Hz, 1 H) 4.74 (d, J = 13.60 Hz, 1 H) 7.80 (s, 1 H) 8.64 (brs, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| C6 | N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-2-ethyl-4-methyl-1,3-oxazole-5-carboxamide | 25.7 | 1H NMR (400 MHz, CHLOROFORM-d) δ ppm 0.98-1.03 (m, 6 H) 1.32 (t, J =7.6 Hz, 3 H) 1.65 (s, 3 H) 1.74 (s, 3H) 1.99-2.07 (m, 1 H) 2.15-2.24 (m, 4 H) 2.47 (s, 3 H) 2.54-2.62 (m, 1 H) 2.69-2.80 (m, 3H) 2.91-2.95 (m, 1 H) 3.12-3.25 (m, 1H) 4.56-4.73 (m, 2 H) 8.30 (s, 1 H) |
| C7 | N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-5-ethyl-1,3-oxazole-4-carboxamide | 66.4 | 1H NMR (400 MHz, CHLOROFORM-d) δ ppm 0.98-1.02 (m, 6 H) 1.26 (t, J = 7.6 Hz, 3 H) 1.65 (s, 3 H) 1.73 (s, 3 H) 1.95-2.05 (m, 1 H) 2.12-2.23 (m, 4 H) 2.53-2.58 (m, 1 H) 2.69-2.73 (m, 1 H) 2.89-2.93 (m, 1 H) 3.09-3.23 (m, 3 H) 4.51 (d, J = 13.60 Hz, 1 H) 4.65 (d, J = 13.60 Hz, 1 H) 7.73 (s, 1 H) 9.25 (brs, 1 H) |
| C8 | 2-cyclopropyl-N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-1,3-oxazole-4-carboxamide | 25 | 1H NMR (400 MHz, CHLOROFORM-d) δ ppm 1.03-1.19 (m, 10 H) 1.66-1.74 (m, 6 H) 1.99-2.06 (s, 1 H) 2.20-2.60 (m, 5 H) 2.70-2.90 (m, 2 H) 2.95-3.05 (m, 1 H), 3.30-3.42 (m, 1H) 4.60 (d, J = 13.60 Hz, 1 H) 4.73 (d, J = 13.60 Hz, 1 H) 8.10 (s, 1 H) 9.90 (brs, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| E1 | 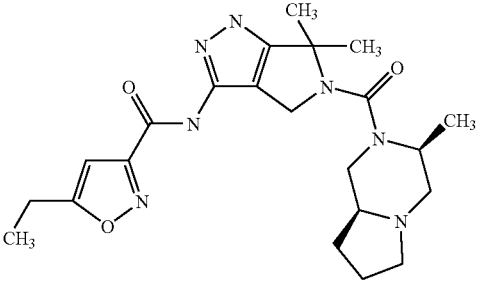<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-ethylisoxazole-3-carboxamide | 61.6 | 1H NMR (500 MHz, D2O) d ppm 1.03 (s, 2 H) 1.20 (t, J = 7.42 Hz, 7 H) 1.54-1.63 (m, 10 H) 1.84 (s, 2 H) 2.00 (s, 2 H) 2.79 (d, J = 7.42 Hz, 3 H) 3.05 (s, 1 H) 4.50 (s, 3 H) 6.66 (s, 1 H) 11.05 (s, 1 H). |
| E2 | 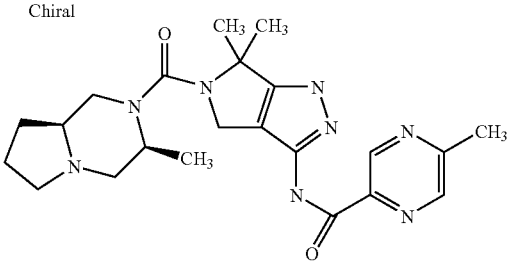<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-methylpyrazine-2-carboxamide | 72.9 | 1H NMR (500 MHz, D2O) d ppm 1.09 (s, 2 H) 1.54-1.63 (m, 11 H) 1.81 (s, 2 H) 1.97 (s, 1 H) 3.41 (s, 9 H) 4.54 (s, 1 H) 4.61 (s, 1 H) 8.63 (s, 1 H) 9.07 (s, 1 H). |
| E3 | 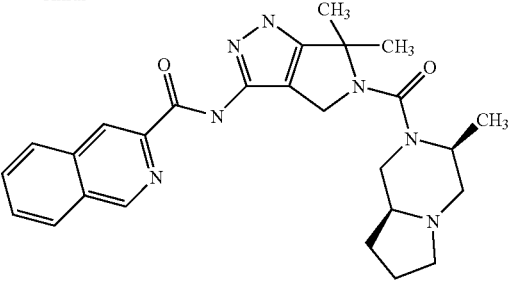<br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)isoquinoline-3-carboxamide | 5.51 | 1H NMR (400 MHz, DMSO-d6) d ppm 1.24 (d, J = 6.57 Hz, 3 H) 1.25-1.37 (m, 1 H) 1.60 (s, 3 H) 1.64 (s, 3 H) 1.66-1.78 (m, 2 H) 1.79-1.88 (m, 1 H) 1.97 (q, J = 8.76 Hz, 1 H) 2.23 (dd, J = 10.36, 3.54 Hz, 1 H) 2.72-2.83 (m, 2 H) 2.88-2.96 (m, 1 H) 3.36 (dd, J = 12.51, 2.40 Hz, 2 H) 3.79-3.91 (m, 1 H) 4.54-4.73 (m, 2 H) 7.76 (t, J = 7.45 Hz, 1 H) 7.86-7.95 (m, 1 H) 8.12 (d, J = 7.83 Hz, 1 H) 8.20-8.27 (m, 2 H) 8.63 (d, J = 8.59 Hz, 1 H) 10.90 (s, 1 H) 12.17 (s, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| E4 | Chiral 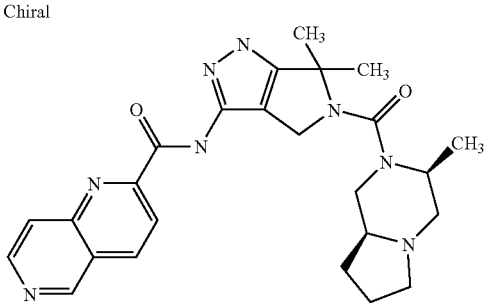<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,6-naphthyridine-2-carboxamide | 6.17 | 1H NMR (400 MHz, DMSO-d6) d ppm 1.24 (d, J = 6.82 Hz, 3 H) 1.26-1.36 (m, 1 H) 1.60 (s, 3 H) 1.64 (s, 3 H) 1.66-1.78 (m, 2 H) 1.79-1.87 (m, 1 H) 1.97 (q, J = 8.67 Hz, 1 H) 2.22 (dd, J = 10.48, 3.41 Hz, 1 H) 2.71-2.85 (m, 2 H) 2.86-3.00 (m, 1 H) 3.35-3.40 (m, 2 H) 3.80-3.90 (m, 1 H) 4.52-4.77 (m, 2 H) 8.10 (d, J = 6.06 Hz, 1 H) 8.38 (d, J = 8.34 Hz, 1 H) 8.80-8.93 (m, 2 H) 9.56 (s, 1 H). |
| E5 | Chiral 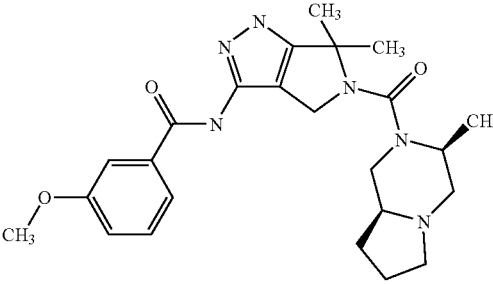<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3-ethoxybenzamide | 37.5 | 1H NMR (500 MHz, D2O) d ppm 1.09 (s, 2 H) 1.30 (t, J = 6.73 Hz, 4 H) 1.56 (s, 4 H) 1.62 (s, 5 H) 1.81 (s, 2 H) 1.97 (s, 2 H) 3.40 (s, 5 H) 4.05 (q, J = 6.78 Hz, 3 H) 4.54 (s, 2 H) 7.07 (s, 1 H) 7.35 (s, 1 H) 7.46 (s, 3 H) 10.82 (s, 1 H). |
| E8 | Chiral 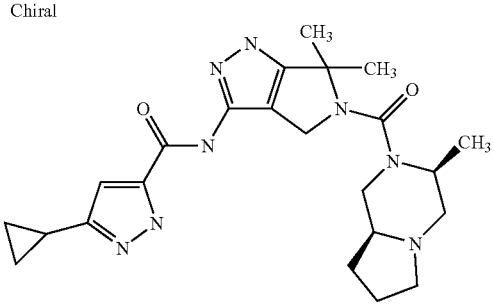<br><br>3-cyolopropyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1H-pyrazole-5-carboxamide | 6.81 | $^1$H NMR (500 MHz, D$_2$O) d ppm 0.67 (s, 2 H) 0.92 (s, 3 H) 1.04 (s, 2 H) 1.21 (s, 2 H) 1.55 (d, J = 12.91 Hz, 9 H) 1.89 (s, 2 H) 2.01 (s, 1 H) 2.28 (s, 1 H) 2.72 (s, 1 H) 2.85 (s, 2 H) 3.05 (s, 1 H) 3.42 (s, 4 H) 4.51 (s, 2 H) 6.24-6.52 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| E7 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoxaline-2-carboxamide | 12.5 | 1H NMR (400 MHz, DMSO-d6) d ppm 1.23 (d, J = 5.81 Hz, 3 H) 1.26-1.41 (m, 1 H) 1.61 (s, 3 H) 1.65 (s, 3 H) 1.67-1.84 (m, J = 26.06 Hz, 4 H) 1.93-2.11 (m, 1 H) 2.15-2.33 (m, 1 H) 2.75-2.87 (m, 2 H) 2.90-3.01 (m, 1 H) 3.24-3.40 (m, 2 H) 3.80-3.96 (m, 1 H) 4.53-4.75 (m, 2 H) 7.98-8.05 (m, 1 H) 8.18-8.25 (m, 1 H) 8.26-8.33 (m, 1 H) 9.54 (s, 1 H) 11.65-12.21 (m, 1 H) 12.54 (s, 1 H). |
| E8 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1-methyl-1H-pyrazole-5-carboxamide | 118 | 1H NMR (500 MHz, D2O) d ppm 1.06 (s, 2 H) 1.19 (s, 2 H) 1.56 (s, 4 H) 1.58-1.65 (m, 5 H) 1.83 (s, 1 H) 1.99 (s, 1 H) 3.42 (s, 8 H) 4.02 (s, 3 H) 4.51 (s, 2 H) 7.05 (s, 1 H) 7.45 (s, 1 H) 10.87 (s, 1 H). |
| E9 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2-methylthiazole-4-carboxamide | 31.3 | 1H NMR (500 MHz, D2O) d ppm 1.06 (s, 2 H) 1.20 (s, 2 H) 1.54-1.63 (m, 11 H) 1.82 (s, 2 H) 2.00 (s, 2 H) 2.67-2.73 (m, 5 H) 3.12 (s, 1 H) 4.52 (s, 1 H) 4.58 (s, 1 H) 8.24 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| E10 | Chiral<br><br>3-tert-butyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1-methyl-1H-pyrazole-5-carboxamide | 10.6 | 1H NMR (500 MHz, D2O) d ppm 1.05 (s, 1 H) 1.20 (s, 12 H) 1.55 (s, 4 H) 1.57-1.65 (m, 4 H) 1.84 (s, 2 H) 1.99 (s, 1 H) 3.41 (s, 7 H) 3.95 (s, 3 H) 4.50 (s, 2 H) 6.95 (s, 1 H) 10.74 (s, 1 H). |
| E11 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,4-dimethyloxazole-5-carboxamide | 28.9 | 1H NMR (500 MHz, D2O) d ppm 1.09 (s, 2 H) 1.21 (s, 2 H) 1.53-1.62 (m, 12 H) 1.82 (s, 2 H) 2.00 (s, 2 H) 2.30 (s, 6 H) 4.47 (s, 3 H) 10.57 (s, 1 H). |
| E12 | Chiral<br><br>5-cyclopropyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)isoxazole-3-carboxamide | 58.6 | 1H NMR (500 MHz, D2O) d ppm 0.89 (d, J = 4.94 Hz, 2 H) 0.91 (s, 1 H) 1.07 (d, J = 5.22 Hz, 5 H) 1.22 (s, 2 H) 1.55 (s, 5 H) 1.61 (s, 6 H) 1.83 (s, 2 H) 1.99 (s, 2 H) 2.17 (s, 2 H) 4.49 (s, 3 H) 6.59 (s, 1 H) 11.01 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| E13 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,3,6-trifluorobenzamide | 135 | 1H NMR (500 MHz, D2O) d ppm 1.01 (s, 2 H) 1.20 (d, J = 14.28 Hz, 3 H) 1.28 (s, 1 H) 1.57 (s, 10 H) 1.86 (s, 1 H) 2.05 (s, 1 H) 2.71 (s, 1 H) 4.56 (s, 2 H) 7.21 (s, 1 H) 7.59 (s, 1 H) 11.38 (s, 1 H) 12.50 (s, 1 H). |
| E14 | Chiral<br><br>N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-3-ethylisoxazole-5-carboxamide | 157 | 1H NMR (400 MHz, CDCl3-d) d ppm 1.29-1.40 (m, 3 H), 1.33 (t, J = 7.5 Hz, 3H), 1.63-2.14 (m, 11 H), 2.26-2.46 (m, 1 H), 2.72-3.06 (m, 6 H), 3.48-3.63 (m, 1 H), 3.90-4.05 (m, 1 H), 4.53-4.84 (m, 2 H), 6.92 (s, 1 H), 10.05 (brs, 1H) 10.54 (brs, 1 H). |
| F1 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide | 22.4 | $^1$H NMR (300 MHz, DMSO-$d_6$) δ ppm 0.95 (d, J = 5.27 Hz, 3 H), 1.00 (d, J = 5.84 Hz, 3 H), 1.06-1.20 (m, 2 H), 1.29 (t, J = 7.54 Hz, 3 H), 1.48-1.73 (m, 10 H), 1.92-2.00 (m, 2 H), 2.37 (s, 3 H), 2.39-2.46 (m, 2 H), 2.72-2.89 (m, 3 H), 3.01-3.18 (m, 2 H), 3.20-3.30 (m, 2 H), 3.82 (d, J = 9.04 Hz, 2 H), 4.53 (s, 2 H), 10.66 (s, 1 H), 12.16 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F2 | N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)-2,6-dimethylpyrimidine-4-carboxamide | 78.4 | 1H NMR (500 MHz, DMSO-d6) δ 0.87-1.07 (m, 6 H) 1.51-1.61 (m, 4 H) 1.61-1.76 (m, 6 H) 1.91 (s, 3 H) 2.00-2.12 (m, 2 H) 3.00-3.16 (m, 4 H) 3.20-3.30 (m, 2 H) 4.54-4.77 (m, 2 H) 7.82 (s, 1 H). |
| F3 | N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyrazine-2-carboxamide | 625 | 1H NMR (500 MHz, DMSO-d6) δ 0.96-1.09 (m, 3 H) 1.09-1.22 (m, 4 H) 1.52-1.63 (m, 4 H) 1.63-1.70 (m, 4 H) 1.72-1.80 (m, 1 H) 1.79-1.88 (m, 1 H) 2.89-3.11 (m, 5 H) 3.11-3.29 (m, 4 H) 4.68 (br. s., 2 H) 8.71-8.87 (m, 1 H) 8.87-8.99 (m, 1 H) 9.20-9.33 (m, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F4 | 3-ethyl-N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)-1-methyl-1H-pyrazole-5-carboxamide | 37.3 | 1H NMR (500 MHz, DMSO-d6) δ 0.90-0.96 (m, 3 H) 0.96-1.05 (m, 3 H) 1.10-1.22 (m, 3 H) 1.52-1.58 (m, 3 H) 1.58-1.64 (m, 3 H) 1.64-1.68 (m, 3 H) 2.97-3.06 (m, 2 H) 3.05-3.15 (m, 3 H) 3.14-3.25 (m, 4 H) 3.90-4.05 (m, 4 H) 4.47-4.65 (m, 2 H) 6.87-6.99 (m, 1 H). |
| F5 | N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide | 71.8 | 1H NMR (500 MHz, DMSO-d6) δ 0.93-1.03 (m, 3 H) 1.04-1.10 (m, 3 H) 1.10-1.18 (m, 1 H) 1.51-1.62 (m, 4 H) 1.62-1.68 (m, 3 H) 1.69-1.82 (m, 2 H) 2.35 (br. s., 3 H) 2.82-2.97 (m, 3 H) 2.95-3.10 (m, 2 H) 3.10-3.20 (m, 2 H) 3.23 (s, 2 H) 4.50-4.63 (m, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F6 | 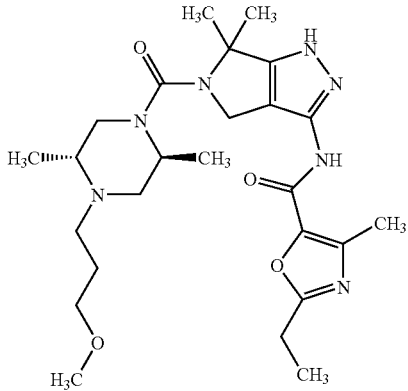<br>2-ethyl-N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)-4-methyl-1,3-oxazole-5-carboxamide | 83.6 | 1H NMR (500 MHz, DMSO-d6) δ 0.88-1.06 (m, 6 H) 1.23-1.34 (m, 3 H) 1.57 (br. s., 3 H) 1.58-1.64 (m, 3 H) 1.65 (br. s., 3 H) 1.92 -2.03 (m, 2 H) 2.15-2.27 (m, 3 H) 2.31-2.38 (m, 4 H) 2.73-2.85 (m, 3 H) 2.97-3.05 (m, 2 H) 3.05-3.13 (m, 2 H) 3.21 (s, 2 H) 4.45-4.61 (m, 2 H). |
| F7 | 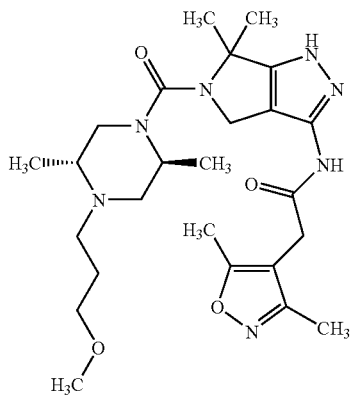<br>2-(3,5-dimethylisoxazol-4-yl)-N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)acetamide | 67.1 | 1H NMR (500 MHz, DMSO-d6) δ 0.94-1.02 (m, 3 H) 1.02-1.11 (m, 3 H) 1.56 (br. s., 3 H) 1.64 (br. s., 3 H) 1.67-1.81 (m, 2 H) 1.91 (s, 3 H) 2.08-2.12 (m, 2 H) 2.13 (s, 3 H) 2.26-2.29 (m, 2 H) 2.31 (s, 3 H) 2.94 (none, 4 H) 3.08-3.19 (m, 2 H) 3.19-3.25 (m, 1 H) 4.41-4.59 (m, 2 H) 10.64 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F8 | 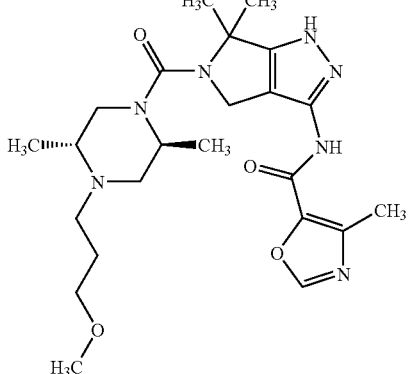 N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)-4-methyl-1,3-oxazole-5-carboxamide | 95.6 | 1H NMR (500 MHz, DMSO-d6) δ 0.96-1.06 (m, 3 H) 1.53-1.62 (m, 3 H) 1.62-1.70 (m, 4 H) 1.70-1.86 (m, 4 H) 1.91 (s, 3 H) 3.03-3.26 (m, 7 H) 3.70-3.92 (m, 2 H) 4.49-4.68 (m, 2 H) 8.45 (br. s., 1 H). |
| F9 | 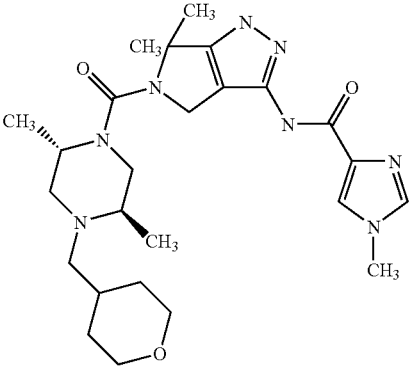 N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-methyl-1H-imidazole-4-carboxamide | 62.4 | $^1$H NMR (500 MHz, DMSO-$d_6$) δ ppm 0.99-1.10 (m, 6 H), 1.50-1.70 (m, 10 H), 3.74 (s, 3 H), 3.82-3.93 (m, 2 H), 4.60-4.74 (m, 2 H), 7.76-7.78 (m, 1 H), 7.78-7.80 (m, 1 H) |
| F10 | 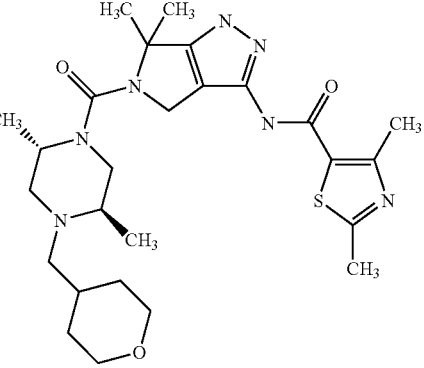 N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-thiazole-5-carboxamide | 22.6 | $^1$H NMR (500 MHz, DMSO-$d_6$) δ ppm 0.99-1.06 (m, 3 H), 1.06-1.27 (m, 5 H), 1.44-1.77 (m, 10 H), 2.64 (s, 3 H), 3.80-3.89 (m, 2 H), 4.52-4.62 (m, 2 H), 10.58-10.65 (m, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F11 | 5-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)isoxazole-3-carboxamide | 29.8 | $^1$H NMR (500 MHz, DMSO-d$_6$) δ ppm 0.95 (d, J = 6.11 Hz, 5 H), 1.00 (d, J = 5.84 Hz, 3 H), 1.06-1.17 (m, 3 H), 1.48-1.71 (m, 10 H), 1.92-1.98 (m, 2 H), 2.17-2.27 (m, 2 H), 2.77-2.85 (m, 1 H), 3.77-3.86 (m, 3 H), 4.56 (s, 2 H), 6.66 (s, 1 H) |
| F12 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1,3-dimethyl-1H-pyrazole-5-carboxamide | 33.0 | $^1$H NMR (500 MHz, DMSO-d$_6$) δ ppm 1.00-1.07 (m, 6 H), 1.08-1.22 (m, 2 H), 1.47-1.73 (m, 10 H), 2.18 (s, 3 H), 3.78-3.90 (m, 3 H), 4.00 (s, 3 H), 4.51-4.64 (m, 2 H), 6.85 (d, J = 1.30 Hz, 1 H), 10.69-10.80 (m, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F13 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methylisoxazole-3-carboxamide | 41.1 | $^1$H NMR (500 MHz, DMSO-d$_6$) δ ppm 0.97 (d, J = 3.85 Hz, 3 H), 1.01 (d, J = 6.04 Hz, 3 H), 1.04-1.20 (m, 2 H), 1.48-1.73 (m, 10 H), 1.93-2.02 (m, 2 H), 2.68 (s, 3 H), 3.76-3.87 (m, 3 H), 4.57 (s, 2 H), 6.70 (s, 1 H) |
| F14 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-ethyl-3-methyl-1H-pyrazole-5-carboxamide | 20.0 | $^1$H NMR (500 MHz, DMSO-d$_6$) δ ppm 0.92-0.97 (m, 3 H), 1.03 (d, J = 0.48 Hz, 3 H), 1.05-1.17 (m, 2 H), 1.26-1.34 (m, 3 H), 1.46-1.72 (m, 10 H), 1.92-2.00 (m, 2 H), 2.68 (s, 3 H), 2.74-2.88 (m, 1 H), 3.75-3.88 (m, 2 H), 4.38-4.48 (m, 2 H), 4.51-4.57 (m, 2 H), 6.81-6.86 (m, 1 H) |
| F15 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethyl-1,3-oxazole-4-carboxamide | 52.1 | $^1$H NMR (500 MHz, DMSO-d$_6$) δ ppm 0.84-1.06 (m, 6 H), 1.17-1.28 (m, 3 H), 1.46-1.77 (m, 10 H), 3.69-3.94 (m, 2 H), 4.48-4.69 (m, 2 H), 8.33-8.51 (m, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F16 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-methyl-1H-pyrazole-3-carboxamide | 25.8 | $^1$H NMR (500 MHz, DMSO-d$_6$) δ ppm 0.98-1.10 (m, 3 H), 1.13-1.36 (m, 5 H), 1.49-1.78 (m, 10 H), 3.79-3.91 (m, 3 H), 3.95 (s, 3 H), 4.55-4.80 (m, 2 H), 6.71-6.87 (m, J = 2.98, 1.59, 0.70, 0.70 Hz, 1 H), 7.74-7.93 (m, 1 H) |
| F17 | 3-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-pyrazole-5-carboxamide | 19.4 | $^1$H NMR (500 MHz, DMSO-d$_6$) δ ppm 0.69-0.74 (m, 2 H), 0.92-0.98 (m, 5 H), 0.99-1.02 (m, 3 H), 1.04-1.20 (m, 2 H), 1.46-1.74 (m, 10 H), 1.91-1.99 (m, 2 H), 2.82 (d, J = 14.15 Hz, 1 H), 3.78-3.90 (m, 2 H), 4.57 (s, 2 H) |
| F18 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-ethylisoxazole-5-carboxamide | 32.1 | $^1$H NMR (500 MHz, DMSO-d$_6$) δ ppm 0.92-0.97 (m, 3 H), 0.99-1.03 (m, 3 H), 1.04-1.18 (m, 2 H), 1.24 (t, J = 7.49 Hz, 3 H), 1.51-1.73 (m, 10 H), 1.92-1.98 (m, 2 H), 2.69-2.76 (m, 2 H), 2.78-2.85 (m, 1 H), 3.71-3.92 (m, 3 H), 4.47-4.63 (m, 1 H), 7.24 (s, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F19 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide | 26.5 | $^1$H NMR (500 MHz, DMSO-d$_6$) δ ppm 0.94-0.99 (m, 3 H), 1.00-1.03 (m, 3 H), 1.05-1.18 (m, 2 H), 1.23-1.30 (m, 3 H), 1.50-1.75 (m, 10 H), 1.93-2.08 (m, 2 H), 2.80-2.88 (m, 3 H), 3.78-3.88 (m, 2 H), 4.49-4.65 (m, 2 H), 6.65-6.79 (m, 1 H) |
| F20 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide | 19.7 | $^1$H NMR (500 MHz, DMSO-d$_6$) δ ppm 0.97-1.08 (m, 3 H), 1.13-1.28 (m, 3 H), 1.52-1.73 (m, 10 H), 2.32-2.39 (m, 3 H), 3.77-3.92 (m, 3 H), 4.53-4.65 (m, 2 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F21 | 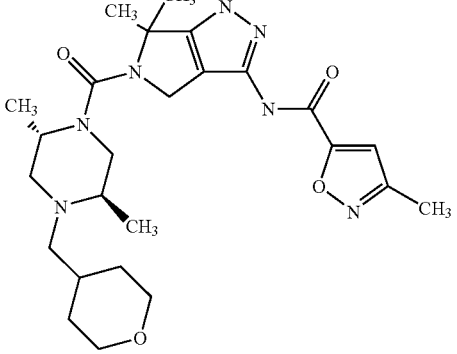 N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-methylisoxazole-5-carboxamide | 38.1 | $^1$H NMR (500 MHz, DMSO-d$_6$) δ ppm 0.97-1.10 (m, 3 H), 1.10-1.28 (m, 5 H), 1.50-1.77 (m, 10 H), 2.26-2.37 (m, 3 H), 3.81-3.90 (m, 2 H), 4.55-4.68 (m, 2 H), 7.14-7.19 (m, 1 H) |
| F22 | 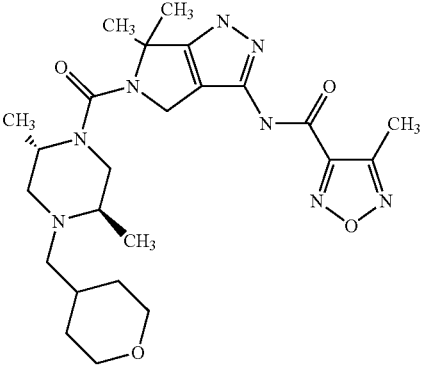 N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-methyl-1,2,5-oxadiazole-3-carboxamide | 47.3 | $^1$H NMR (500 MHz, DMSO-d$_6$) δ ppm 0.92-0.99 (m, 3 H), 1.00-1.03 (m, 3 H), 1.06-1.20 (m, 2 H), 1.48-1.75 (m, 10 H), 1.91-2.08 (m, 2 H), 3.77-3.88 (m, 3 H), 4.53-4.63 (m, 2 H) |
| F23 | 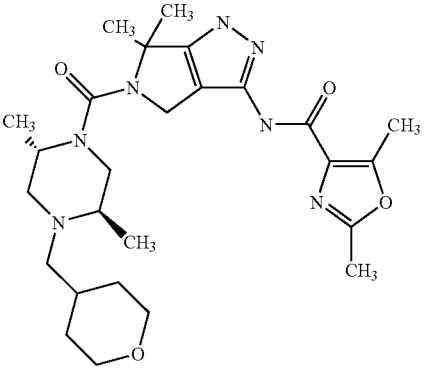 N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,5-dimethyl-1,3-oxazole-4-carboxamide | 31.3 | $^1$H NMR (500 MHz, DMSO-d$_6$) δ ppm 0.90-1.01 (m, 3 H), 1.00-1.06 (m, 3 H), 1.07-1.20 (m, 2 H), 1.23-1.28 (m, 1 H), 1.48-1.74 (m, 10 H), 3.77-3.88 (m, 3 H), 4.50-4.63 (m, 2 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F24 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-propylisoxazole-3-carboxamide | 59.4 | $^1$H NMR (500 MHz, DMSO-d$_6$) δ ppm 0.91-0.98 (m, 6 H), 0.98-1.02 (m, 3 H), 1.04-1.18 (m, 2 H), 1.46-1.60 (m, 5 H), 1.60-1.73 (m, 7 H), 1.92-1.99 (m, 2 H), 2.77-2.85 (m, 2 H), 3.76-3.86 (m, 2 H), 4.50-4.61 (m, 2 H), 6.70-6.76 (m, 1 H) |
| F25 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-thiazole-4-carboxamide | 33.3 | $^1$H NMR (500 MHz, DMSO-d$_6$) δ ppm 0.93-0.97 (m, 3 H), 0.98-1.03 (m, 3 H), 1.05-1.18 (m, 2 H), 1.36 (t, J = 7.62 Hz, 3 H), 1.49-1.73 (m, 10 H), 1.92-1.99 (m, 2 H), 2.79-2.86 (m, 1 H), 3.02-3.11 (m, 1 H), 3.75-3.88 (m, 3 H), 4.04-4.15 (m, 2 H), 4.55-4.69 (m, 2 H), 8.36 (d, J = 1.37 Hz, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F26 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-fluoropyridine-2-carboxamide. | 12.8 | $^1$H NMR (300 MHz, DMSO-$d_6$) δ ppm 0.95 (d, J = 5.46 Hz, 3 H), 1.00 (d, J = 6.03 Hz, 3 H), 1.05-1.26 (m, 2 H), 1.47-1.78 (m, 10 H), 1.91-2.00 (m, 2 H), 2.32-2.47 (m, 2 H), 2.82 (d, J = 9.04 Hz, 1 H), 3.00-3.19 (m, 2 H), 3.20-3.30 (m, 2 H), 3.74-3.91 (m, 2 H), 4.63 (s, 2 H), 7.92-8.05 (m, 1 H), 8.17-8.32 (m, 1 H), 8.73 (d, J = 2.45 Hz, 1 H), 10.79 (br. s., 1 H), 12.22 (br. s., 1 H) |
| F27 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-methylpyridine-2-carboxamide. | 21.7 | $^1$H NMR (300 MHz, DMSO-$d_6$) δ ppm 0.97 (d, J = 4.71 Hz, 3 H), 1.01 (d, J = 6.03 Hz, 3 H), 1.06-1.25 (m, 2 H), 1.45-1.77 (m, 10 H), 1.92-2.05 (m, 2 H), 2.34-2.47 (m, 5 H), 2.80-2.91 (m, 1 H), 3.05-3.20 (m, 2 H), 3.21-3.30 (m, 2 H), 3.82 (d, J = 9.23 Hz, 2 H), 4.65 (s, 2 H), 7.52 (d, J = 4.14 Hz, 1 H), 8.02 (s, 1 H), 8.57 (d, J = 4.90 Hz, 1 H) |
| F28 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-6-methoxypyridine-2-carboxamide | 46.7 | $^1$H NMR (300 MHz, DMSO-$d_6$) δ ppm 0.95 (d, J = 5.46 Hz, 3 H), 1.01 (d, J = 6.03 Hz, 3 H), 1.05-1.24 (m, 2 H), 1.47-1.75 (m, 10 H), 1.91-1.99 (m, 2 H), 2.32-2.47 (m, 2 H), 2.75-2.90 (m, 1 H), 3.03-3.18 (m, 2 H), 3.22-3.30 (m, 2 H), 3.82 (d, J = 10.55 Hz, 2 H), 4.03 (s, 3 H), 4.63 (s, 2 H), 7.10 (d, J = 8.29 Hz, 1 H), 7.74 (d, J = 7.16 Hz, 1 H), 7.94 (t, J = 7.82 Hz, 1 H), 10.41 (br. s., 1 H), 12.56 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F29 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methoxypyridine-2-carboxamide. | <10 | $^1$H NMR (300 MHz, DMSO-$d_6$) δ ppm 0.96 (d, J = 4.33 Hz, 3 H), 1.01 (d, J = 6.03 Hz, 3 H), 1.06-1.23 (m, 2 H), 1.45-1.75 (m, 10 H), 1.91-2.01 (m, 2 H), 2.38-2.48 (m, 2 H), 2.77-2.94 (m, 1 H), 3.04-3.19 (m, 2 H), 3.21-3.31 (m, 2 H), 3.76-3.87 (m, 2 H), 3.93 (s, 3 H), 4.64 (s, 2 H), 7.54-7.68 (m, 1 H), 8.13 (d, J= 8.85 Hz, 1 H), 8.39 (d, J = 2.64 Hz, 1 H). |
| F30 | 5-chloro-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide | 11.9 | $^1$H NMR (300 MHz, DMSO-$d_6$) δ ppm 0.95 (d, J = 5.65 Hz, 3 H), 1.01 (d, J = 6.03 Hz, 3 H), 1.06-1.28 (m, 2 H), 1.46-1.76 (m, 10 H), 1.89-2.01 (m, 2 H), 2.29-2.47 (m, 2 H), 2.76-2.89 (m, 1 H), 3.02-3.19 (m, 2 H), 3.20-3.30 (m, 2 H), 3.75-3.90 (m, 2 H), 4.63 (s, 2 H), 8.11-8.28 (m, 2 H), 8.79 (d, J = 1.88 Hz, 1 H) |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F31 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-6-methylpyridine-2-carboxamide | 15.0 | $^1$H NMR (300 MHz, DMSO-d$_6$) δ ppm 0.95 (d, J = 5.46 Hz, 3 H), 1.00 (d, J = 5.84 Hz, 3 H), 1.05-1.25 (m, 2 H), 1.48-1.81 (m, 10 H), 1.91-2.02 (m, 2 H), 2.32-2.48 (m, 2 H), 2.61 (s, 3 H), 2.75-2.90 (m, 1 H), 3.03-3.19 (m, 2 H), 3.20-3.31 (m, 2 H), 3.66-3.97 (m, 2 H), 4.66 (s, 2 H), 7.40-7.71 (m, 1 H), 7.80-8.16 (m, 2 H) |
| F32 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide | 12.8 | $^1$H NMR (300 MHz, DMSO-d$_6$) δ ppm 0.96 (d, J = 4.33 Hz, 3 H), 1.00 (d, J = 6.03 Hz, 3 H), 1.05-1.24 (m, 2 H), 1.48-1.79 (m, 10 H), 1.92-2.03 (m, 2 H), 2.35-2.47 (m, 2 H), 2.75 (s, 3 H), 2.78-2.90 (m, 1 H), 3.02-3.17 (m, 2 H), 3.20-3.30 (m, 2 H), 3.75-3.88 (m, 2 H), 4.60 (s, 2 H), 8.35 (s, 1 H |
| F33 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methylpyridine-2-carboxamide | 26.4 | $^1$H NMR (300 MHz, DMSO-d$_6$) δ ppm 0.96 (d, J = 5.27 Hz, 3 H), 1.01 (d, J = 5.84 Hz, 3 H), 1.04-1.19 (m, 2 H), 1.49-1.79 (m, 10 H), 1.91-2.00 (m, 2 H), 2.42 (s, 3 H), 2.44-2.47 (m, 2 H), 2.75-2.88 (m, 1 H), 3.01-3.19 (m, 2 H), 3.20-3.29 (m, 2 H), 3.77-3.89 (m, 2 H), 4.64 (s, 2 H), 7.83-7.94 (m, 1 H), 8.06 (d, J = 7.72 Hz, 1 H), 8.57 (d, J = 1.32 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F34 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-ethyl-1-methyl-1H-pyrazole-5-carboxamide | <10 | $^1$H NMR (300 MHz, DMSO-d$_6$) δppm 0.95 (d, J = 4.52 Hz, 3 H), 1.01 (d, J = 6.03 Hz, 3 H), 1.04-1.12 (m, 2 H), 1.18 (t, J = 7.54 Hz, 3 H), 1.47-1.76 (m, 10 H), 1.91-2.01 (m, 2 H), 2.35-2.47 (m, 2 H), 2.53-2.61 (m, 2 H), 2.73-2.90 (m, 1 H), 3.00-3.17 (m, 2 H), 3.18-3.30 (m, 2 H), 3.82 (d, J = 9.23 Hz, 2 H), 4.00 (s, 3 H), 4.55 (s, 2 H), 6.92 (s, 1 H), 10.80 (s, 1 H), 12.47 (br. s., 1 H). |
| F35 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-methyl-1H-imidazole-5-carboxamide. | 47.9 | $^1$H NMR (300 MHz, MeOH) δ ppm 1.04 (d, J= 6.03 Hz, 3 H), 1.11 J = 6.03 Hz, H), 1.15-1.34 (m, 2 H), 1.57-1.86 (m, 10 H), 1.97-2.11 (m, 2 H), 2.47-2.70 (m, 3 H), 2.86-2.96 (m, 1 H), 3.11-3.22 (m, 1 H), 3.35-3.50 (m, 2 H), 3.88-3.96 (m, 2 H), 3.98 (s, 3 H), 4.68 (s, 2 H), 7.77 (s, 1 H), 7.82 (s, 1 H). |
| F36 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-methyl-1H-imidazole-4-carboxamide | 62.4 | $^1$H NMR (300 MHz, DMSO-d$_6$) δ ppm 0.95 (d, J= 5.46 Hz, 3 H), 1.00 (d, J = 6.03 Hz, 3 H), 1.06-1.28 (m, 2 H), 1.45-1.80 (m, 10 H), 1.93-1.98 (m, 2 H), 2.31-2.47 (m, 2 H), 2.76-2.88 (m, 1 H), 3.01-3.19 (m, 4 H), 3.72 (s, 3 H), 3.77-3.88 (m, 2 H), 4.57 (s, 2 H), 7.76 (s, 1 H), 7.85 (s, 1 H), 10.08 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F37 | 1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide | 14.1 | $^1$H NMR (300 MHz, DMSO-d6) δ ppm 0.95 (d, J = 5.46 Hz, 3 H) 1.00 (d, J = 5.84 Hz, 3 H) 1.04-1.29 (m, 2 H) 1.50-1.69 (m, 10 H) 1.72-2.02 (m, 6 H) 2.29-2.46 (m, 4 H) 2.75-2.89 (m, 1 H) 2.98-3.20 (m, 4 H) 3.82 (d, J = 10.93 Hz, 2 H) 4.58 (s, 2 H) 4.66-4.92 (m, 1 H) 7.91 (s, 1 H) 8.09 (s, 1 H). |
| F38 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide | 23.8 | $^1$H NMR (300 MHz, DMSO-d$_6$) δ ppm 0.95 (d, J = 5.65 Hz, 3 H), 0.99 (d, J = 6.22 Hz, 3 H), 1.03-1.27 (m, 2 H), 1.42 (s, 3 H), 1.45 (s, 3 H), 1.50-1.77 (m, 10 H), 1.87-1.99 (m, 2 H), 2.33-2.46 (m, 2 H), 2.77-2.88 (m, 1 H), 3.02-3.29 (m, 4 H), 3.76-3.87 (m, 2 H), 4.43-4.54 (m, 1 H), 4.58 (s, 2 H), 7.90 (s, 1 H), 8.03 (d, J = 1.13 Hz, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F39 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrola[3,4-c]pyrazol-3-yl)-2-ethyl-1,3-axazole-4-carboxamide | 14.9 | $^1$H NMR (300 MHz, DMSO-$d_6$) δ ppm 1.01 (d, J = 5.09 Hz, 6 H), 1.07-1.19 (m, 2 H), 1.28 (t, J = 7.54 Hz, 3 H), 1.45-1.81 (m, 10 H), 1.83-2.06 (m, 2 H), 2.28-2.46 (m, 2 H), 2.79-2.88 (m, 3 H), 2.90-3.22 (m, 4 H), 3.83 (d, J = 9.23 Hz, 2 H), 4.60 (s, 2 H), 8.69 (s, 1 H) |
| F40 | 2-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1,3-oxazole-4-carboxamide | 15.7 | $^1$H NMR (300 MHz, DMSO-$d_6$) δ ppm 0.93-1.06 (m, 6 H), 1.04-1.17 (m, 4 H), 1.16-1.28 (m, J = 6.40, 1.88 Hz, 2 H), 1.46-1.77 (m, 10 H), 1.82-2.03 (m, 2 H), 2.11-2.24 (m, 1 H), 2.32-2.46 (m, 1 H), 2.63-2.99 (m, 2 H), 3.03-3.25 (m, 4 H), 3.83 (d, J = 9.61 Hz, 2 H), 4.59 (s, 2 H), 8.62 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
| --- | --- | --- | --- |
| F41 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydrapyrrolo[3,4-c]pyrazol-3-yl)-5-methyl-1,3-oxazole-4-carboxamide | 117 | $^1$H NMR (300 MHz, DMSO-$d_6$) δ ppm 0.97 (d, J = 2.07 Hz, 4 H), 1.01 (d, J = 6.03 Hz, 3 H), 1.07-1.22 (m, 2 H), 1.45-1.61 (m, 5 H), 1.61-1.76 (m, 5 H), 1.91 (s, 1 H), 1.95 (d, J = 3.77 Hz, 1 H), 2.53-2.57 (m, 1 H), 2.62 (s, 2 H), 2.69 (s, 2 H), 2.83 (d, J = 5.46 Hz, 1 H), 3.07 (s, 1 H), 3.12 (d, J = 11.49 Hz, 2 H), 3.24 (d, J = 5.46 Hz, 1 H), 3.26-3.30 (m, 2 H), 3.82 (d, J = 9.04 Hz, 2 H), 4.56 (s, 1 H), 8.44 (s, 1 H). |
| F42 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)benzamide | 30.1 | $^1$H NMR (300 MHz, DMSO-$d_6$) δ ppm 1.02 (d, J = 5.09 Hz, 6 H), 1.17 (s, 3 H), 1.60 (s, 6 H), 1.68 (s, 5 H), 1.91 (s, 2 H), 2.39 (s, 2 H), 2.78 (d, J = 4.52 Hz, 1 H), 3.15 (s, 1 H), 3.26 (s, 2 H), 3.81 (s, 3 H), 4.61 (s, 2 H), 7.47-7.62 (m, 3 H), 7.98 (d, J = 7.35 Hz, 2 H), 10.92 (s, 1 H) |
| F43 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-ethyl-1H-pyrazole-3-carboxamide | 26.9 | $^1$H NMR (300 MHz, DMSO-$d_6$) δ ppm 0.95 (d, J = 5.65 Hz, 3 H), 1.00 (d, J = 6.03 Hz, 3 H), 1.04-1.24 (m, 2 H), 1.43 (t, J = 7.25 Hz, 3 H), 1.48-1.76 (m, 10 H), 1.85-2.01 (m, 2 H), 2.37-2.46 (m, J = 10.36 Hz, 2 H), 2.82 (dd, J = 10.93, 2.45 Hz, 1 H), 2.99-3.18 (m, 2 H), 3.18-3.28 (m, 2 H), 3.82 (d, J = 9.23 Hz, 2 H), 4.24 (q, J = 6.97 Hz, 2 H), 4.58 (s, 2 H), 6.82 (s, 1 H), 7.90 (s, 1 H), 10.29 (br. s., 1 H), 12.13 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F44 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-methylbenzamide | <10 | $^1$H NMR (300 MHz, DMSO-$d_6$) δ ppm 0.96 (d, J = 3.20 Hz, 3 H), 1.01 (d, J = 6.03 Hz, 3 H), 1.06-1.25 (m, 2 H), 1.48-1.80 (m, 4 H), 1.59 (s, 3 H), 1.68 (s, 3 H), 1.92-2.02 (m, 2 H), 2.38 (s, 3 H), 2.40-2.47 (m, 2 H), 2.75-2.90 (m, 1 H), 3.01-3.19 (m, 2 H), 3.19-3.28 (m, 2 H), 3.82 (d, J = 9.42 Hz, 2 H), 4.58 (s, 2 H), 7.31-7.45 (.m, 2 H), 7.72-7.86 (m, 2 H), 10.82 (s, 1 H), 12.28 (br. s., 1 H |
| F45 | N-(5-{[(2S,SR)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methylbenzamide | 67.1 | $^1$H NMR (300 MHz, DMSO-$d_6$) δ ppm 0.95 (d, J= 5.84 Hz, 3 H), 1.01 (d, J = 6.03 Hz, 3 H), 1.05-1.22 (m, 2 H), 1.46-1.79 (m, 4 H), 1.58 (s, 3 H), 1.67 (s, 3 H), 1.86-1.96 (m, 2 H), 2.38 (s, 3 H), 2.41-2.47 (m, 2 H), 2.76-2.85 (m, 1 H), 3.01-3.19 (m, 2 H), 3.21-3.28 (m, 2 H), 3.82 (d, J = 8.48 Hz, 2 H), 4.56 (s, 2 H), 7.28 (d, J = 7.54 Hz, 2 H), 7.32-7.48 (m, 2 H), 10.76 (br. s., 1 H), 12.27 (br. s., 1 H). |
| F46 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-fluorobenzamide | 11.2 | $^1$H NMR (300 MHz, DMSO-$d_6$) δ ppm 0.95 (d, J = 5.65 Hz, 3 H), 1.00 (d, J = 6.03 Hz, 3 H), 1.06-1.22 (m, 2 H), 1.47-1.84 (m, 4 H), 1.58 (s, 3 H), 1.68 (s, 3 H), 1.91-2.01 (m, 2 H), 2.30-2.48 (m, 2 H), 2.76-2.87 (m, 1 H), 3.01-3.19 (m, 2 H), 3.19-3.29 (m, 2 H), 3.72-3.91 (m, 2 H), 4.58 (s, 2 H), 7.18-7.48 (m, 2 H), 7.89-8.30 (m, 2 H), 10.98 (s, 1 H), 12.43, (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F47 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydrapyrrola[3,4-c]pyrazol-3-yl)-3-fluorobenzamide | <10 | $^1$H NMR (300 MHz, DMSO-$d_6$) δ ppm 0.95 (d, J = 5.84 Hz, 3 H), 1.00 (d, J = 6.03 Hz, 3 H), 1.05-1.22 (m, 2 H), 1.47-1.80 (m, 4 H), 1.59 (s, 3 H), 1.68 (s, 3 H), 1.91-1.99 (m, 2 H), 2.35-2.47 (m, 2 H), 2.76-2.86 (m, 1 H), 3.01-3.18 (m, 2 H), 3.20-3.28 (m, 2 H), 3.74-3.89 (m, 2 H), 4.59 (s, 2 H), 7.38-7.49 (m, 1 H), 7.50-7.62 (m, 1 H), 7.73-7.91 (m, 2 H), 11.05 (s, 1 H), 12.23 (br. s., 1 H). |
| F48 | 4-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)benzamide. | 24.3 | $^1$H NMR (300 MHz, DMSO-$d_6$) δ ppm 0.95 (d, J = 5.65 Hz, 3 H), 1.00 (d, J = 6.03 Hz, 3 H), 1.05-1.23 (m, 2 H), 1.47-1.76 (m, 4 H), 1.59 (s, 3 H), 1.68 (s, 3 H), 1.90-1.99 (m, 2 H), 2.33-2.50 (m, 2 H), 2.74-2.90 (m, 1 H), 3.01-3.18 (m, 2 H), 3.18-3.28 (m, 2 H), 3.82 (d, J = 10.36 Hz, 2 H), 4.59 (s, 2 H), 7.93-8.04 (m, 2 H), 8.07-8.18 (m, 2 H), 11.22 (s, 1 H), 12.42 (br. s., 1 H). |
| F49 | 3-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)benzamide | 25.6 | $^1$H NMR (300 MHz, DMSO-$d_6$) δ ppm 0.95 (d, J = 5.65 Hz, 3 H), 1.00 (d, J = 6.03 Hz, 3 H), 1.05-1.26 (m, 2 H), 1.44-1.80 (m, 4 H), 1.59 (s, 3 H), 1.68 (s, 3 H), 1.91-2.00 (m, 2 H), 2.34-2.48 (m, 2 H), 2.75-2.88 (m, 1 H), 3.02-3.18 (m, 2 H), 3.20-3.27 (m, 2 H), 3.82 (d, J = 9.80 Hz, 2 H), 4.60 (s, 2 H), 7.67-7.79 (m, 1 H), 8.05 (d, J = 7.72 Hz, 1 H), 8.28 (d, J = 7.91 Hz, 1 H), 8.42 (s, 1 H), 11.19 (s, 1 H), 12.50 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F50 | N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)pyrimidine-2-carboxamide | 96.1 | $^1$H NMR (300 MHz, DMSO-$d_6$) δ ppm 0.90-1.02 (m, 6 H), 1.59 (s, 3 H), 1.68 (s, 3 H), 1.82-1.94 (m, 1 H), 2.01-2.13 (m, 1 H), 2.16 (s, 3 H), 2.27-2.40 (m, 1 H), 2.70 (dd, J = 11.11, 2.45 Hz, 1 H), 2.91-3.09 (m, 2 H), 4.48-4.81 (m, 2 H), 7.75 (t, J = 4.80 Hz, 1 H), 9.03 (d, J = 4.71 Hz, 2 H), 10.84 (br. s., 1 H), 12.46 (br. s., 1 H). |
| F51 | N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-ethylpyridine-2-carboxamide | <10 | 1H NMR (300 MHz, DMSO-$d_6$) δ 0.99-1.14 (m, 3 H) 1.15-1.28 (m, 3 H) 1.28-1.40 (m, 3 H) 1.50-1.73 (m, 6 H) 1.73-1.83 (m, 1 H) 1.84-2.06 (m, 2 H) 2.67-2.88 (m, 3 H) 2.88-3.03 (m, 1 H) 3.24-3.36 (m, 2 H) 3.56-3.72 (m, 3 H) 3.72-3.89 (m, 4 H) 3.90-4.09 (m, 4 H) 4.63-4.80 (m, 1 H) 7.92 (d, J = 8.10 Hz, 1 H) 8.05 (d, J = 7.54 Hz, 1 H) 8.60 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F52 | N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide | <10 | 1H NMR (300 MHz, DMSO-d$_6$) δ 1.00-1.14 (m, 8 H) 1.14-1.31 (m, 3 H) 1.14-1.31 (m, 2 H) 1.51-1.63 (m, 6 H) 1.63-1.81 (m, 8 H) 3.69-3.84 (m, 6 H) 3.85-4.04 (m, 4 H) 4.56-4.74 (m, 2 H) 7.46 (d, J = 8.85 Hz, 1 H) 7.96 (d, J = 8.48 Hz, 1 H) 8.37 (d, J = 2.45 Hz, 1 H). |
| F53 | N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyrimidme-4-carboxamide | 24.0 | 1H NMR (300 MHz, DMSO-d$_6$) δ 0.99-1.15 (m, 3 H) 1.23-1.41 (m, 3 H) 1.62 (br. s., 3 H) 1.69 (br. s., 4 H) 1.72-1.81 (m, 2 H) 1.81-1.90 (m, 2 H) 1.91-2.00 (m, 1 H) 2.69-2.86 (m, 2 H) 2.86-3.05 (m, 2 H) 3.40-3.52 (m, 4 H) 3.68-3.87 (m, 1 H) 3.89-4.03 (m, 2 H) 4.63-4.74 (m, 2 H) 8.03-8.13 (m, 1 H) 9.06-9.19 (m, 1 H) 9.42 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F54 | N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methylpyridine-2-carboxamide | 12.2 | 1H NMR (300 MHz, DMSO-$d_6$) δ 0.94-1.12 (m, 6 H) 1.51 (br. s., 3 H) 1.55-1.63 (m, 5 H) 1.67 (br. s., 4 H) 2.11-2.22 (m, 1 H) 2.43 (s, 3 H) 2.69-2.83 (m, 3 H) 2.83-2.94 (m, 1 H) 3.05-3.22 (m, 3 H) 3.05-3.22 (m, 1 H) 3.82-3.95 (m, 2 H) 4.56-4.70 (m, 2 H) 7.88 (d, J = 7.54 Hz, 1 H) 8.02-8.09 (m, 1 H) 8.58 (s, 1 H). |
| F55 | N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methoxypyridine-2-carboxamide | <10 | 1H NMR (300 MHz, DMSO-$d_6$) δ 0.94-1.08 (m, 6 H) 1.40-1.53 (m, 2 H) 1.54-1.62 (m, 4 H) 1.62-1.74 (m, 4 H) 2.00-2.12 (m, 4 H) 2.12-2.22 (m, 1 H) 2.69-2.81 (m, 2 H) 2.81-2.91 (m, 1 H) 3.06-3.22 (m, 3 H) 3.84-3.99 (m, 5 H) 4.60-4.71 (m, 2 H) 7.62 (d, J = 8.29 Hz, 1 H) 8.14 (d, J = 8.48 Hz, 1 H) 8.39 (s, 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
| --- | --- | --- | --- |
| F56 | 5-chloro-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide | <10 | 1H NMR (300 MHz, DMSO-$d_6$) δ 0.91-1.18 (m, 6 H) 1.19-1.41 (m, 2 H) 1.43-1.63 (m, 6 H) 1.63-1.84 (m, 7 H) 2.01-2.18 (m, 1 H) 2.18-2.35 (m, 1 H) 2.68-2.79 (m, 1 H) 2.79-2.99 (m, 2 H) 3.53-3.68 (m, 1 H) 3.79-4.02 (m, 2 H) 4.53-4.77 (m, 2 H) 8.05-8.25 (m, 2 H) 8.79 (br. s., 1 H). |
| F57 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyrazine-2-carboxamide | 52.7 | 1H NMR (300 MHz, DMSO-$d_6$) δ 0.89-0.99 (m, 3 H) 0.99-1.06 (m, 4 H) 1.46-1.63 (m, 6H) 1.63-1.67 (m, 6 H) 1.88-2.02 (m, 2 H) 2.34-2.46 (m, 3 H) 2.76-2.90 (m, 1 H) 3.14-3.19 (m, 3 H) 3.76-3.88 (m, 3 H) 4.59-4.71 (m, 2 H) 8.72-8.85 (m, 1 H) 8.86-9.01 (m, 1 H) 9.21-9.35 (m, 1 H). |
| F58 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyrimidine-2-carboxamide | 133 | 1H NMR (300 MHz, DMSO-$d_6$) δ 0.91-0.98 (m, 4 H) 1.01 (d, J = 5.84 Hz, 3 H) 1.42-1.55 (m, 3 H) 1.55-1.62 (m, 4 H) 1.62-1.81 (m, 6 H) 1.85-2.00 (m, 3 H) 2.77-2.89 (m, 1 H) 2.95-3.19 (m, 4 H) 3.75-3.89 (m, 3 H) 4.52-4.71 (m, 2 H) 7.68-7.81 (m, 1 H) 8.90-9.08 (m, 2 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| F59 | 2-(3,5-dimethylisoxazol-4-yl)-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)acetamide | 20 | 1H NMR (300 MHz, DMSO-$d_6$) δ 1.01 (d, J = 6.03 Hz, 3 H) 1.09-1.18 (m, 1 H) 1.18-1.27 (m, 2 H) 1.28-1.40 (m, 4 H) 1.47-1.53 (m, 3 H) 1.59 (s, 3 H) 1.65 (s, 3 H) 1.86-2.00 (m, 1 H) 2.02-2.11 (m, 1 H) 2.12 (s, 3 H) 2.31 (s, 3 H) 2.73-2.91 (m, 3 H) 2.91-3.07 (m, 2 H) 3.77-3.89 (m, 3 H) 4.46-4.60 (m, 2 H) 6.35-6.66 (m, 1 H) 9.95-10.18 (m, 1 H) 10.62-10.78 (m, 1 H). |
| F60 | N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyl)pyridine-2-carboxamide | 4.17 | 1H NMR (300 MHz, CHLOROFORM-d) δ 0.94-1.23 (m, 6 H) 1.23-1.46 (m, 4 H) 1.71-1.85 (m, 9 H) 1.84-2.02 (m, 1 H) 3.09-3.25 (m, 1 H) 3.28-3.41 (m, 1 H) 3.41-3.51 (m, 2 H) 3.88-4.02 (m, 4 H) 4.64-4.87 (m, 2 H) 8.11 -8.30 (m, 1 H) 8.33-8.53 (m, 1 H) 8.90 (s, 1 H) 10.29 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| G1 | 5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazal-3-yl)pyridine-2-carboxamide | <10 | 1H NMR (300 MHz, DMSO-d$_6$) δ 0.87-1.13 (m, 6 H) 1.26-1.40 (m, 1 H) 1.40-1.54 (m, 2 H) 1.54-1.63 (m, 3 H) 1.63-1.77 (m, 4 H) 2.06-2.27 (m, 2 H) 2.68-2.94 (m, 3 H) 3.04-3.20 (m, 4 H) 3.79-3.95 (m, 2 H) 4.52-4.76 (m, 2 H) 8.29 (d, J = 8.10 Hz, 1 H) 8.59 (d, J = 9.61 Hz, 1 H) 9.19 (br. s., 1 H). |
| G2 | 5-cyano-N-(6,6-dimethyl-5-{[(2S,5R)-2,4,5-trimethylpiperazin-1-yl]carbonyl}-1,4,5,6-tetrahydropyrrolo[3,4-c]pyrazol-3-yl)pyridine-2-carboxamide | 28.7 | 1H NMR (300 MHz, DMSO-d$_6$) δ 0.97-1.12 (m, 3 H) 1.19-1.33 (m, 3 H) 1.61 (s, 3 H) 1.69 (s, 3 H) 2.66-2.81 (m, 6 H) 2.81-2.96 (m, 2H) 3.12-3.19 (m, 1 H) 4.65-4.78 (m, 2 H) 6.54 (s, 1 H) 8.25 (d, J = 8.10 Hz, 1 H) 8.59 (dd, J = 8.19, 1.98 Hz, 1 H) 9.20 (d, J = 1.32 Hz, 1 H) 11.05 (br. s., 1 H). |

TABLE 1-continued

The following Table 1 depicts Ki, structure, nomenclature, and NMR data of the embodiments of the Invention. Unless otherwise specifically exemplified, compounds in Table 1 were synthesized starting from commercially available materials or by known methods using routine modifications of the above described examples. While the invention has been illustrated by reference to specific embodiments, those skilled in the art will recognize that additional variations and modifications may be made through routine experimentation and practice of the invention. Thus, the invention is intended not to be limited by the foregoing description, but to be defined by the appended claims and their equivalents. The foregoing detailed description and examples have been given for clarity of understanding only.

| Ex. No. | Structure | PKCb Ki (nM) | 1H NMR |
|---|---|---|---|
| G3 | 5-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide | <10 | 1H NMR (300 MHz, DMSO-$d_6$) δ 0.91-1.09 (m, 8 H) 1.09-1.25 (m, 2 H) 1.49-1.62 (m, 4 H) 1.62-1.81 (m, 6 H) 1.86-2.02 (m, 3 H) 2.34-2.47 (m, 2 H) 2.76-2.91 (m, 1 H) 3.00-3.21 (m, 3 H) 3.77-3.95 (m, 2 H) 4.58-4.75 (m, 2 H) 8.29 (d, J = 7.91 Hz, 1 H) 8.59 (d, J = 6.03 Hz, 1 H) 9.20 (br. s., 1 H). |
| H1 | N-[5-({(2S,5R)-4-[(4-hydroxytetrahydro-2H-pyran-4-yl)methyl]-2,5-dimethylpiperazin-1-yl}carbonyl)-6,6-dimethyl-1,4,5,6-tetrahydropyrrolo[3,4-c]pyrazol-3-yl]pyridine-2-carboxamide | NA | H NMR (300 MHz, DMSO-$d_6$) δ ppm 0.97 (d, J = 5.27 Hz, 3 H), 1.04 (d, J = 6.03 Hz, 3 H), 1.25-1.47 (m, 2 H), 1.52-1.75 (m, 8 H), 2.07-2.26 (m, 2 H), 2.36-2.47 (m, 1 H), 2.53-2.62 (m, 2 H), 2.99-3.12 (m, 1 H), 3.16 (d, J = 8.48 Hz, 1 H), 3.23-3.31 (m, 1 H), 3.52-3.69 (m, 4 H), 4.10 (s, 1 H), 4.53-4.74 (m, 2 H), 7.64-7.76 (m, 1 H), 8.09 (t, J = 6.97 Hz, 1 H), 8.13-8.22 (m, 1 H), 8.74 (d, J = 3.77 Hz, 1 H). |

NA = Not available.
NT = Not tested.

We claim:
1. A compound or pharmaceutically acceptable salt of Formula (I),

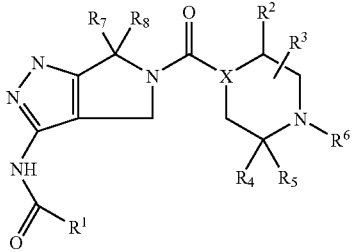

wherein:
X is C or N;
$R^1$ is selected from an aryl or

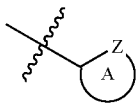

wherein ring A is a 5 to 6 membered heterocyclyl containing Z, wherein Z is an O, S or N heteroatom which is adjacent to the point of attachment, and wherein $R^1$ is optionally further substituted with 0 to 3 $R^9$ groups and wherein two of the $R^9$ groups may optionally cyclize to form an aryl or a 5-6 membered heterocyclyl ring containing N or S fused to the aryl or heterocyclyl to which it is attached;

$R^2$ is H or $C_1$-$C_6$ alkyl optionally further substituted with 0 to 3 $R^9$ groups;

when X is N, $R^3$ may be attached to any carbon on the ring and is selected from H, $C_1$-$C_6$ alkyl, halide, or perfluoroalkyl;

when X is C, $R^3$ is a fluoro and is attached to X;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2$$R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2$$R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2$$R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$, or $R^4$ and $R^5$ may together cyclize to form a 3-to-5-membered spiro-cycloalkyl; wherein any of the said $C_3$-$C_{12}$ cycloalkyl, aryl, heterocyclyl, or heteroaryl are independently optionally further substituted by 0 to 3 $R_9$ groups;

$R^6$ is selected from $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2$$R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2$$R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2$$R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; or $R^6$ may together with $R^4$ cyclize to form a 4-to 7-membered heterocyclyl ring fused to the piperazine or piperadine to which they are attached; and wherein any of the said alkyl, alkenyl, alkynyl, cycloalkyl, aryl, heterocyclyl, and heteroaryl may independently be further substituted with 0 to 3 $R^9$ groups;

each $R^7$ and $R^8$ is independently $C_1$-$C_2$ alkyl, or $R^7$ and $R^8$ together cyclize to form a cyclopropyl or cyclobutyl;

each $R^9$ is independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2$$R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2$$R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2$$R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^d$, $R^e$, $C_3$-$C_{12}$ cycloalkyl, aryl or 3-15 membered heterocyclyl are independently optionally further substituted by 1-3 groups selected from -halide, $C_1$-$C_6$ alkyl, $C_1$-$C_6$ perfluoroalkyl, $C_1$-$C_6$alkoxyl, $C_1$-$C_6$alkylamino, CN or oxo;

each $R^a$, $R^b$ and $R^c$ is independently selected from H, $C_1$-$C_6$perfluoroalkyl, $C_1$-$C_8$ alkyl, $C_2$-$C_8$ alkenyl, —($C_1$-$C_3$ alkylene)$_m$—($C_3$-$C_8$ cycloalkyl), —($C_1$-$C_3$ alkylene)$_m$-($C_3$-$C_8$ cycloalkenyl), $C_2$-$C_8$ alkynyl, —($C_1$-$C_3$ alkylene)$_m$-aryl, or —($C_1$-$C_3$ alkylene)$_m$-(3-8 member heterocyclyl), and each $R^a$, $R^b$ and $R^c$ is independently optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may optionally form a -(3-8 membered heterocyclyl), and said 3-8 membered heterocyclyl is optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently —($C_1$-$C_3$ alkylene)-, —($C_2$-$C_5$ alkenylene)-, or —($C_2$-$C_5$ alkynylene)-;

each m is independently 0 or 1; and with the proviso that if X=N, then $R^2$, $R^3$, $R^4$ and $R^5$ are not all H.

2. The compound or pharmaceutically acceptable salt according to claim 1, wherein $R^7$ and $R^8$ are both methyl.

3. The compound or pharmaceutically acceptable salt according to claim 1, wherein X is N.

4. The compound or pharmaceutically acceptable salt according to claim 1, wherein $R^1$ is a pyridine or a piperazine.

5. The compound or pharmaceutically acceptable salt according to claim 1, wherein $R^1$ is a 5-membered heterocyclyl.

6. The compound or pharmaceutically acceptable salt according to claim 1, wherein $R^1$ is selected from the group consisting of oxazole, isoxazole, thiazole or imidazole.

7. The compound or pharmaceutically acceptable salt according to claim 1, wherein $R^2$ or $R^4$ is methyl.

8. The compound or pharmaceutically acceptable salt according to claim 1, wherein $R^6$ is —$(R^d)_m$-(3-15 membered heterocyclyl).

9. The compound or pharmaceutically acceptable salt according to claim 1, wherein $R^6$ is —$(R^d)_m$tetrahydropyran.

10. The compound or pharmaceutically acceptable salt according to claim 1, wherein $R^6$ is tetrahydro-2H-pyran-4-ylmethyl.

11. The compound or pharmaceutically acceptable salt according to claim 1, wherein $R^2$ is —$CH_3$ in (S) configuration.

12. The compound or pharmaceutically acceptable salt according to claim 1, wherein $R^6$ is —$(R^d)_m$—$OR^a$.

13. A compound or pharmaceutically acceptable salt selected from the group consisting of:

- N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide;
- N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide;
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;
- 1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide;
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;
- N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide; and
- N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyl)pyridine-2-carboxamide.

14. A pharmaceutical composition comprising an effective amount of a compound according to claim 1, or a pharmaceutically acceptable salt thereof, and a pharmaceutically acceptable carrier.

* * * * *